(12) United States Patent
Mueller et al.

(10) Patent No.: US 11,739,330 B2
(45) Date of Patent: Aug. 29, 2023

(54) SOD1 DUAL EXPRESSION VECTORS AND USES THEREOF

(71) Applicant: University of Massachusetts, Boston, MA (US)

(72) Inventors: Christian Mueller, Concord, MA (US); Robert H. Brown, Needham, MA (US)

(73) Assignee: University of Massachusetts, Boston, MA (US)

( * ) Notice: Subject to any disclaimer, the term of this patent is extended or adjusted under 35 U.S.C. 154(b) by 552 days.

(21) Appl. No.: 16/649,164

(22) PCT Filed: Sep. 21, 2018

(86) PCT No.: PCT/US2018/052173
§ 371 (c)(1),
(2) Date: Mar. 20, 2020

(87) PCT Pub. No.: WO2019/060686
PCT Pub. Date: Mar. 28, 2019

(65) Prior Publication Data
US 2020/0248187 A1    Aug. 6, 2020

Related U.S. Application Data

(60) Provisional application No. 62/561,932, filed on Sep. 22, 2017.

(51) Int. Cl.
| | | |
|---|---|---|
| *C12N 15/113* | (2010.01) | |
| *C12N 15/86* | (2006.01) | |
| *C12N 7/00* | (2006.01) | |
| *A61K 35/76* | (2015.01) | |
| *A61K 48/00* | (2006.01) | |

(52) U.S. Cl.
CPC .......... *C12N 15/1137* (2013.01); *A61K 35/76* (2013.01); *C12N 7/00* (2013.01); *C12N 15/86* (2013.01); *A61K 48/00* (2013.01); *C12N 2750/14043* (2013.01)

(58) Field of Classification Search
None
See application file for complete search history.

(56) References Cited

U.S. PATENT DOCUMENTS

| | | |
|---|---|---|
| 5,478,745 A | 12/1995 | Samulski et al. |
| 5,871,982 A | 2/1999 | Wilson et al. |
| 6,001,650 A | 12/1999 | Colosi |
| 6,156,303 A | 12/2000 | Russell et al. |
| 6,177,403 B1 | 1/2001 | Stedman |
| 6,251,677 B1 | 6/2001 | Wilson et al. |
| 6,485,966 B2 | 11/2002 | Gao et al. |
| 6,544,786 B1 | 4/2003 | Xiao et al. |
| 6,953,690 B1 | 10/2005 | Gao et al. |
| 7,022,519 B2 | 4/2006 | Gao et al. |
| 7,132,530 B2 | 11/2006 | Bennett et al. |
| 7,198,951 B2 | 4/2007 | Gao et al. |
| 7,235,393 B2 | 6/2007 | Gao et al. |
| 7,387,896 B2 | 6/2008 | Turner et al. |
| 7,427,396 B2 | 9/2008 | Arbetman et al. |
| 7,456,015 B2 | 11/2008 | Bohn et al. |
| 7,498,316 B2 | 3/2009 | Xu et al. |
| 7,622,455 B2 | 11/2009 | Bennett et al. |
| 7,678,895 B2 | 3/2010 | Bennett et al. |
| 7,691,995 B2 | 4/2010 | Zamore et al. |
| 7,750,144 B2 | 7/2010 | Zamore et al. |
| 7,772,203 B2 | 8/2010 | Zamore et al. |
| 7,892,793 B2 | 2/2011 | Xu |
| 7,902,163 B2 | 3/2011 | Bennett et al. |
| 7,906,111 B2 | 3/2011 | Wilson et al. |
| 8,008,271 B2 | 8/2011 | Xu et al. |
| 8,202,846 B2 | 6/2012 | Hannon et al. |
| 8,222,221 B2 | 7/2012 | Corey et al. |
| 8,309,533 B2 | 11/2012 | Xu |
| 8,524,446 B2 | 9/2013 | Gao et al. |
| 8,729,036 B2 | 5/2014 | Zamore et al. |
| 8,734,809 B2 | 5/2014 | Gao et al. |
| 8,993,529 B2 | 3/2015 | Bennett et al. |
| 9,102,949 B2 | 8/2015 | Gao et al. |
| 9,121,018 B2 | 9/2015 | Zamore et al. |
| 9,193,753 B2 | 11/2015 | Tuschl et al. |
| 9,217,155 B2 | 12/2015 | Gao et al. |
| 9,226,976 B2 | 1/2016 | Flotte et al. |

(Continued)

FOREIGN PATENT DOCUMENTS

| | | |
|---|---|---|
| JP | 2011-511636 A | 4/2011 |
| JP | 2017-510298 A | 4/2017 |

(Continued)

OTHER PUBLICATIONS

U.S. Appl. No. 16/611,581, filed Nov. 7, 2019, Mueller et al.
Partial European Search Report for Application No. EP 20183218.5, dated Nov. 10, 2020.
Extended European Search Report for Application No. EP 20183218. 5, dated Mar. 31, 2021.
Extended European Search Report for Application No. EP 18797613. 9, dated Dec. 8, 2020.

(Continued)

*Primary Examiner* — Nicole Kinsey White

(74) *Attorney, Agent, or Firm* — Wolf, Greenfield & Sacks, P.C.

(57) ABSTRACT

In some aspects, the disclosure relates to compositions and methods useful for inhibiting SOD1 expression in cells (e.g., cells of a subject). In some embodiments, the disclosure describes isolated nucleic acids engineered to express an inhibitory nucleic acid targeting endogenous SOD1 and an mRNA encoding a hardened SOD1 protein. In some embodiments, compositions and methods described by the disclosure are useful for treating Amyotrophic Lateral Sclerosis (ALS) in a subject.

18 Claims, 9 Drawing Sheets

Specification includes a Sequence Listing.

(56) References Cited

U.S. PATENT DOCUMENTS

| | | |
|---|---|---|
| 9,249,424 B2 | 2/2016 | Wolf et al. |
| 9,272,053 B2 | 3/2016 | Gao et al. |
| 9,284,357 B2 | 3/2016 | Gao et al. |
| 9,546,369 B2 | 1/2017 | Gao et al. |
| 9,596,835 B2 | 3/2017 | Gao et al. |
| 9,611,472 B2 | 4/2017 | Zamore et al. |
| 9,701,984 B2 | 7/2017 | Gao et al. |
| 9,850,487 B2 | 12/2017 | Zamore et al. |
| 9,879,253 B2 | 1/2018 | Zamore et al. |
| 9,885,057 B2 | 2/2018 | Flotte et al. |
| 10,072,251 B2 | 9/2018 | Gao et al. |
| 10,077,452 B2 | 9/2018 | Flotte et al. |
| 10,166,297 B2 | 1/2019 | Gao et al. |
| 10,280,418 B2 | 5/2019 | Mueller et al. |
| 10,300,146 B2 | 5/2019 | Gao et al. |
| 10,370,432 B2 | 8/2019 | Esteves et al. |
| 10,597,656 B2 | 3/2020 | Flotte et al. |
| 10,711,274 B2 | 7/2020 | Mueller et al. |
| 10,781,453 B2 | 9/2020 | Heslin et al. |
| 10,793,861 B2 | 10/2020 | Kaspar et al. |
| 2001/0016355 A1 | 8/2001 | Samulski et al. |
| 2002/0164783 A1 | 11/2002 | Feldhaus |
| 2002/0192823 A1 | 12/2002 | Bartlett |
| 2003/0103939 A1 | 6/2003 | Engelhardt et al. |
| 2003/0110526 A1 | 6/2003 | Brown et al. |
| 2003/0138772 A1 | 7/2003 | Gao et al. |
| 2004/0101514 A1 | 5/2004 | Liu et al. |
| 2004/0219528 A1 | 11/2004 | Morris et al. |
| 2005/0014262 A1 | 1/2005 | Gao et al. |
| 2005/0019915 A1 | 1/2005 | Bennett et al. |
| 2005/0032219 A1 | 2/2005 | Aubourg et al. |
| 2005/0037988 A1 | 2/2005 | Zamore et al. |
| 2005/0137153 A1 | 6/2005 | McSwiggen et al. |
| 2005/0197313 A1 | 9/2005 | Roelvink |
| 2005/0255086 A1 | 11/2005 | Davidson et al. |
| 2005/0255089 A1 | 11/2005 | Chiorini et al. |
| 2005/0255487 A1 | 11/2005 | Khvorova et al. |
| 2005/0261218 A1 | 11/2005 | Esau et al. |
| 2005/0287122 A1 | 12/2005 | Bartlett et al. |
| 2005/0288243 A1 | 12/2005 | Xu et al. |
| 2006/0063174 A1 | 3/2006 | Turner et al. |
| 2006/0093589 A1 | 5/2006 | Warrington et al. |
| 2006/0153826 A1 | 7/2006 | Arnould et al. |
| 2006/0189564 A1 | 8/2006 | Burright et al. |
| 2006/0228800 A1 | 10/2006 | Lin et al. |
| 2006/0229268 A1 | 10/2006 | Benjamin et al. |
| 2006/0292117 A1 | 12/2006 | Loiler et al. |
| 2007/0036760 A1 | 2/2007 | Wilson et al. |
| 2007/0243526 A1 | 10/2007 | Kay et al. |
| 2007/0253936 A1 | 11/2007 | Kay et al. |
| 2007/0292410 A1 | 12/2007 | Cashman et al. |
| 2008/0200420 A1 | 8/2008 | Zamore et al. |
| 2009/0042828 A1* | 2/2009 | Xu ................. C12N 15/111 |
| | | 435/375 |
| 2009/0111766 A1 | 4/2009 | Atkinson et al. |
| 2009/0149409 A1 | 6/2009 | Bohn et al. |
| 2009/0215879 A1 | 8/2009 | DiPrimio et al. |
| 2009/0239240 A1 | 9/2009 | Chu |
| 2010/0186103 A1 | 7/2010 | Gao et al. |
| 2010/0323001 A1 | 12/2010 | Pachuk |
| 2011/0039914 A1 | 2/2011 | Pavco et al. |
| 2011/0171262 A1 | 7/2011 | Bakker et al. |
| 2011/0172293 A1 | 7/2011 | Fish et al. |
| 2011/0212520 A1 | 9/2011 | Davidson et al. |
| 2011/0258716 A1 | 10/2011 | Baltimore et al. |
| 2012/0077870 A1 | 3/2012 | Blanks et al. |
| 2012/0137379 A1 | 5/2012 | Gao et al. |
| 2012/0270930 A1 | 10/2012 | Van Der Maarel et al. |
| 2012/0309050 A1 | 12/2012 | Kumon et al. |
| 2013/0030042 A1 | 1/2013 | Couto |
| 2013/0101558 A1 | 4/2013 | Gao et al. |
| 2013/0109742 A1 | 5/2013 | Hewitt et al. |
| 2013/0142861 A1 | 6/2013 | Tsou et al. |
| 2013/0195801 A1 | 8/2013 | Gao et al. |
| 2013/0281516 A1 | 10/2013 | Gao et al. |
| 2014/0142161 A1 | 5/2014 | Flotte et al. |
| 2014/0142288 A1 | 5/2014 | Davidson et al. |
| 2014/0147418 A1 | 5/2014 | Chiorini et al. |
| 2014/0179770 A1 | 6/2014 | Zhang et al. |
| 2014/0201857 A1 | 7/2014 | Fahrenkrug et al. |
| 2014/0296486 A1 | 10/2014 | Gao et al. |
| 2014/0335054 A1 | 11/2014 | Gao et al. |
| 2015/0065560 A1 | 3/2015 | Bjorklund et al. |
| 2015/0252421 A1 | 9/2015 | Pickering-Brown et al. |
| 2015/0258180 A1 | 9/2015 | Mahuran et al. |
| 2015/0259679 A1 | 9/2015 | Bennett et al. |
| 2016/0017005 A1 | 1/2016 | Asokan et al. |
| 2016/0024496 A1 | 1/2016 | Bennett et al. |
| 2016/0060624 A1 | 3/2016 | Davidson et al. |
| 2016/0076054 A1 | 3/2016 | Auricchio et al. |
| 2016/0135438 A1 | 5/2016 | Gao et al. |
| 2016/0153005 A1 | 6/2016 | Zhang et al. |
| 2016/0185832 A1 | 6/2016 | Drivas et al. |
| 2016/0186211 A1 | 6/2016 | Flotte et al. |
| 2016/0194374 A1 | 7/2016 | Wijnholds et al. |
| 2016/0208257 A1 | 7/2016 | Gao et al. |
| 2016/0251655 A1 | 9/2016 | Freier et al. |
| 2016/0272976 A1 | 9/2016 | Kaspar |
| 2016/0326524 A1 | 11/2016 | Flotte et al. |
| 2017/0029785 A1 | 2/2017 | Zhao et al. |
| 2017/0101645 A1 | 4/2017 | Brown et al. |
| 2017/0114340 A1 | 4/2017 | Mueller et al. |
| 2017/0145439 A1 | 5/2017 | Gao et al. |
| 2017/0152517 A1 | 6/2017 | Barkats et al. |
| 2017/0159071 A9 | 6/2017 | Flotte et al. |
| 2017/0165377 A1 | 6/2017 | Gao et al. |
| 2017/0166927 A1 | 6/2017 | Gao et al. |
| 2017/0191039 A1 | 7/2017 | Gao et al. |
| 2017/0349911 A1 | 12/2017 | Gao et al. |
| 2018/0094267 A1 | 4/2018 | Heslin et al. |
| 2018/0140810 A1 | 5/2018 | Cataltepe et al. |
| 2018/0214576 A1 | 8/2018 | Fitzgerald et al. |
| 2018/0265571 A1 | 9/2018 | Esteves et al. |
| 2018/0265863 A1 | 9/2018 | Esteves et al. |
| 2018/0265865 A2 | 9/2018 | Flotte et al. |
| 2018/0298380 A1 | 10/2018 | Gao et al. |
| 2018/0311290 A1 | 11/2018 | Sena-Esteves et al. |
| 2019/0211327 A1 | 7/2019 | Flotte et al. |
| 2019/0276826 A1 | 9/2019 | Mueller et al. |
| 2019/0282709 A1 | 9/2019 | Gao et al. |
| 2019/0316126 A1 | 10/2019 | Mueller et al. |
| 2020/0032256 A1 | 1/2020 | Mueller et al. |
| 2020/0354716 A1 | 11/2020 | Mueller et al. |
| 2021/2456450 | 8/2021 | Mueller et al. |

FOREIGN PATENT DOCUMENTS

| | | |
|---|---|---|
| JP | 2018-538002 A | 12/2018 |
| WO | WO 2003/006477 A1 | 1/2003 |
| WO | WO 2003/042397 A2 | 5/2003 |
| WO | WO 2005/033321 A2 | 4/2005 |
| WO | WO 2005/062937 A2 | 7/2005 |
| WO | WO 2005/116204 A1 | 12/2005 |
| WO | WO 2006/031267 A2 | 3/2006 |
| WO | WO 2006/066066 A2 | 6/2006 |
| WO | WO 2006/119432 A2 | 11/2006 |
| WO | WO 2007/000668 A2 | 1/2007 |
| WO | WO 2007/027775 A2 | 3/2007 |
| WO | WO 2008/091703 A2 | 7/2008 |
| WO | WO 2008/125846 A2 | 10/2008 |
| WO | WO 2008/147839 A1 | 12/2008 |
| WO | WO 2008/150897 A2 | 12/2008 |
| WO | WO 2009/102427 A2 | 8/2009 |
| WO | WO 2009/109665 A1 | 9/2009 |
| WO | WO 2009/146178 A1 | 12/2009 |
| WO | WO 2010/027446 A2 | 3/2010 |
| WO | WO 2010/034314 A1 | 4/2010 |
| WO | WO 2010/071454 A1 | 6/2010 |
| WO | WO 2010/099383 A2 | 9/2010 |
| WO | WO 2010/129021 A1 | 11/2010 |
| WO | WO 2010/138263 A2 | 12/2010 |
| WO | WO 2011/094198 A1 | 8/2011 |
| WO | WO 2011/133890 A1 | 10/2011 |
| WO | WO 2011/135396 A1 | 11/2011 |

(56) References Cited

FOREIGN PATENT DOCUMENTS

| WO | WO 2013/055865 A1 | 4/2013 | |
|----|----|----|----|
| WO | WO 2013/123503 A1 | 8/2013 | |
| WO | WO 2013/170078 A1 | 11/2013 | |
| WO | WO 2013/190059 A1 | 12/2013 | |
| WO | WO 2014/062691 A2 | 4/2014 | |
| WO | WO 2014/114303 A1 | 7/2014 | |
| WO | WO 2014/160092 A1 | 10/2014 | |
| WO | WO 2014/186746 A1 | 11/2014 | |
| WO | WO 2014/197748 A2 | 12/2014 | |
| WO | WO 2015/031392 A1 | 3/2015 | |
| WO | WO 2015/054676 A2 | 4/2015 | |
| WO | WO 2015/089354 A1 | 6/2015 | |
| WO | WO 2015/121501 A1 | 8/2015 | |
| WO | WO-2015143078 A1 * | 9/2015 | ............ A61P 21/02 |
| WO | WO 2015/164786 A1 | 10/2015 | |
| WO | WO 2015/168666 A2 | 11/2015 | |
| WO | WO 2015/195621 A1 | 12/2015 | |
| WO | WO 2016/065001 A1 | 4/2016 | |
| WO | WO 2016/167780 A1 | 10/2016 | |
| WO | WO 2016/174056 A1 | 11/2016 | |
| WO | WO 2016/186772 A2 | 11/2016 | |
| WO | WO-2016187053 A1 * | 11/2016 | .......... A61K 35/761 |
| WO | WO 2016/210372 A2 | 12/2016 | |
| WO | WO 2017/023724 A1 | 2/2017 | |
| WO | WO 2017/109757 A1 | 6/2017 | |
| WO | WO 2018/064600 A1 | 4/2018 | |

OTHER PUBLICATIONS

Third Party Submission under 37 CFR 1.290 for U.S. Appl. No. 16/611,581, filed May 2021.
Extended European Search Report for application No. EP 18859329.7, dated May 3, 2021.
Ciura et al., Loss of function of C9orf72 causes motor deficits in a zebrafish model of amyotrophic lateral sclerosis. Ann Neurol. Aug. 2013;74(2):180-7. doi: 10.1002/ana.23946.
Donnelly et al., RNA toxicity from the ALS/FTD C9ORF72 expansion is mitigated by antisense intervention. Neuron. Oct. 16, 2013;80(2):415-28. doi: 10.1016/j.neuron.2013.10.015. Erratum in: Neuron. Nov. 20, 2013;80(4):1102. Heusler, Aaron R [corrected to Haeusler, Aaron R].
Fernandes et al., Oligonucleotide-Based Therapy for FTD/ALS Caused by the C9orf72 Repeat Expansion: A Perspective. J Nucleic Acids. 2013;2013:208245(1-11). doi: 10.1155/2013/208245. Epub Nov. 17, 2013.
Lagier-Tourenne et al., Targeted degradation of sense and antisense C9orf72 RNA foci as therapy for ALS and frontotemporal degeneration. Proc Natl Acad Sci U S A. Nov. 19, 2013;110(47):E4530-9. doi: 10.1073/pnas.1318835110. Epub Oct. 29, 2013. Supporting Information, 17 pages.
Ran et al., In vivo genome editing using *Staphylococcus aureus* Cas9. Nature. Apr. 9, 2015;520(7546):186-91. doi: 10.1038/nature14299. Epub Apr. 1, 2015. Supplemental Information, 12 pages.
Sareen et al., Targeting RNA foci in iPSC-derived motor neurons from ALS patients with a C9ORF72 repeat expansion. Sci Transl Med. Oct. 23, 2013;5(208):208ra149. doi: 10.1126/scitranslmed.3007529. Author Manuscript, 26 pages.
Stoica et al., Adeno-associated virus-delivered artificial microRNA extends survival and delays paralysis in an amyotrophic lateral sclerosis mouse model. Ann Neurol. Apr. 2016;79(4):687-700. doi: 10.1002/ana.24618. Epub Mar. 11, 2016. Author Manuscript, 24 pages.
Toro et al., 603. Artificial MicroRNAs Against Spliced Variants of the Gene C9ORF72, the Major Cause for Familial Amyotrophic Lateral Sclerosis. Mol Ther. May 2013;21 (Supplement 1):S230-S231. doi: 10.1016/S1525-0016(16)34938-3.
Yamada et al., RNA interference (RNAi). Clinical Chemistry. Sep. 2005;34(3):216-223.
Extended European Search Report for Application No. EP 15764861.9, dated Dec. 15, 2017.

International Search Report and Written Opinion for Application No. PCT/US2015/021321, dated Jun. 26, 2015.
International Preliminary Report on Patentability for Application No. PCT/US2015/021321, dated Sep. 26, 2016.
International Search Report and Written Opinion for Application No. PCT/US2018/031880, dated Sep. 14, 2018.
International Preliminary Report on Patentability for Application No. PCT/US2018/031880, dated Nov. 21, 2019.
International Search Report and Written Opinion for Application No. PCT/US2018/052173, dated Nov. 30, 2018.
International Preliminary Report on Patentability for Application No. PCT/US2018/052173, dated Apr. 2, 2020.
Aartsma-Rus et al., New insights in gene-derived therapy: the example of Duchenne muscular dystrophy. Ann N Y Acad Sci. Dec. 2010;1214:199-212. doi: 10.1111/j.1749-6632.2010.05836.x. Epub Dec. 1, 2010.
Adachi et al., Drawing a high-resolution functional map of adeno-associated virus capsid by massively parallel sequencing. Nat Commun. 2014;5:3075. doi: 10.1038/ncomms4075.
Ahmed et al., A Single Intravenous rAAV Injection as Late as P20 Achieves Efficacious and Sustained CNS Gene Therapy in Canavan Mice. Mol Ther. Jul. 2, 2013. doi: 10.1038/mt.2013.138. [Epub ahead of print].
Akache et al., The 37/67-kilodalton laminin receptor is a receptor for adeno-associated virus serotypes 8, 2, 3, and 9. J Virol. Oct. 2006;80(19):9831-6.
Alisky et al., Gene therapy for amyotrophic lateral sclerosis and other motor neuron diseases. Hum Gene Ther. Nov. 20, 2000;11(17):2315-29.
Arbuthnot et al., Hepatic delivery of RNA interference activators for therapeutic application. Curr Gene Ther. Apr. 2009;9(2):91-103.
Asokan et al., The AAV vector toolkit: poised at the clinical crossroads. Mol Ther. Apr. 2012;20(4):699-708. doi: 10.1038/mt.2011.287. Epub Jan. 24, 2012.
Azzouz et al., VEGF delivery with retrogradely transported lentivector prolongs survival in a mouse ALS model. Nature. May 27, 2004;429(6990):413-7.
Baek et al., AAV-mediated gene delivery in adult GM1-gangliosidosis mice corrects lysosomal storage in CNS and improves survival. PLoS One. Oct. 18, 2010;5(10):e13468. doi: 10.1371/journal.pone.0013468.
Banci et al., SOD1 and amyotrophic lateral sclerosis: mutations and oligomerization. PLoS One. 2008;3(2):e1677. Published Feb. 27, 2008. doi:10.1371/journal.pone.0001677.
Berns et al., Biology of adeno-associated virus. Curr Top Microbiol Immunol. 1996;218:1-23.
Beutler et al., AAV for pain: steps towards clinical translation. Gene Ther. Apr. 2009;16(4):461-9. Epub Mar. 5, 2009.
Biferi et al., Recombinant AAV9 vectors to silence the mutant SOD1 gene in amyotrophic lateral sclersosis. Human gene therapy. Dec. 2013;24(12):A117.
Bish et al., Adeno-associated virus (AAV) serotype 9 provides global cardiac gene transfer superior to AAV1, AAV6, AAV7, and AAV8 in the mouse and rat. Hum Gene Ther. Dec. 2008;19(12):1359-68. doi: 10.1089/hum.2008.123.
Boillée et al., Onset and progression in inherited ALS determined by motor neurons and microglia. Science. Jun. 2, 2006;312(5778):1389-92.
Borel et al., Recombinant AAV as a platform for translating the therapeutic potential of RNA interference. Mol Ther. Apr. 2014;22(4):692-701. doi:10.1038/mt.2013.285. Epub Dec. 19, 2013.
Bourdenx et al., Systemic gene delivery to the central nervous system using Adeno-associated virus. Front Mol Neurosci. Jun. 2, 2014;7:50. doi: 10.3389/fnmol.2014.00050. eCollection 2014.
Brantly et al., Phase I trial of intramuscular injection of a recombinant adeno-associated virus serotype 2 alpha1-antitrypsin (AAT) vector in AAT-deficient adults. Hum Gene Ther. Dec. 2006;17(12):1177-86.
Brown et al., A microRNA-regulated lentiviral vector mediates stable correction of hemophilia B mice. Blood. Dec. 15, 2007;110(13):4144-52. Epub Aug. 28, 2007.

(56) References Cited

OTHER PUBLICATIONS

Brown et al., Endogenous microRNA can be broadly exploited to regulate transgene expression according to tissue, lineage and differentiation state. Nat Biotechnol. Dec. 2007;25(12): 1457-67. Epub Nov. 16, 2007.
Brown et al., Endogenous microRNA regulation suppresses transgene expression in hematopoietic lineages and enables stable gene transfer. Nat Med. May 2006;12(5):585-91. Epub Apr. 23, 2006.
Buning et al., Receptor targeting of adeno-associated virus vectors. Gene Ther. Jul. 2003;10(14):1142-51.
Bussing et al., let-7 microRNAs in development, stem cells and cancer. Trends Mol Med. Sep. 2008;14(9):400-9. doi: 10.1016/j.molmed.2008.07.001. Epub Jul. 31, 2008.
Calcedo et al., Worldwide epidemiology of neutralizing antibodies to adeno-associated viruses. J Infect Dis. Feb. 1, 2009;199(3):381-90.
Carter et al., Adeno-associated virus gene expression and regulation. CRC Handbook of parvoviruses. 1990:227-54.
Carter, in "Handbook of Parvoviruses", ed., P. Tijsser, CRC Press, pp. 155-168 (1990).
Cearley et al., Expanded repertoire of AAV vector serotypes mediate unique patterns of transduction in mouse brain. Mol Ther. Oct. 2008;16(10):1710-8. doi: 10.1038/mt.2008.166. Epub Aug. 19, 2008.
Cearley et al., Transduction characteristics of adeno-associated virus vectors expressing cap serotypes 7, 8, 9, and Rh10 in the mouse brain. Mol Ther. Mar. 2006;13(3):528-37. Epub Jan. 18, 2006.
Chadderton et al., Improved retinal function in a mouse model of dominant retinitis pigmentosa following AAV-delivered gene therapy. Mol Ther. Apr. 2009;17(4):593-9. Epub Jan. 27, 2009.
Chang et al., miR-122, a mammalian liver-specific microRNA, is processed from her mRNA and may downregulate the high affinity cationic amino acid transporter CAT-1. RNA Biol. Jul. 2004;1(2):106-13. Epub Jul. 1, 2004.
Chen et al., Comparative study of anti-hepatitis B virus RNA interference by double-stranded adeno-associated virus serotypes 7, 8, and 9. Mol Ther. Feb. 2009;17(2):352-9. Epub Dec. 9, 2008.
Chen et al., Efficient transduction of vascular endothelial cells with recombinant adeno-associated virus serotype 1 and 5 vectors. Hum Gene Ther. Feb. 2005;16(2):235-47.
Chen et al., Molecular signatures of disease brain endothelia provide new sites for CNS-directed enzyme therapy. Nat Med. Oct. 2009;15(10):1215-8. doi: 10.1038/nm.2025. Epub Sep. 13, 2009.
Chen et al., Regulation of immune responses and tolerance: the microRNA perspective. Immunol Rev. May 2013;253(1):112-28. doi:10.1111/imr.12060.
Cheng et al., Development of optimized AAV3 serotype vectors: mechanism of high-efficiency transduction of human liver cancer cells. Gene Ther. Apr. 2012;19(4):375-84. doi: 10.1038/gt.2011.105. Epub Jul. 21, 2011.
Choudhury et al., Identification of Novel vectors capable of CNS transduction in adult mice after single round selection using DNA shuffled AAV capsid library. Mol Ther. May 1, 2013;21(1):S1.
Christensen et al., A let-7 microRNA-binding site polymorphism in the KRAS 3' UTR is associated with reduced survival in oral cancers. Carcinogenesis. Jun. 2009;30(6):1003-7. doi: 10.1093/carcin/bgp099. Epub Apr. 20, 2009.
Chung et al., Polycistronic RNA polymerase II expression vectors for RNA interference based on BIC/miR-155. Nucleic Acids Res. Apr. 13, 2006;34(7):e53.
Conlon et al., Ribozyme Approaches towards Down-Regulation of Pi*Z Mutant Human a-1 Anti-Trypsin. Mol. Therapy. 2004;9:S333. Abstract 875.
Conrad et al., Safety of single-dose administration of an adeno-associated virus (AAV)-CFTR vector in the primate lung. Gene Ther. Aug. 1996;3(8):658-68.
Coulouarn et al., Loss of miR-122 expression in liver cancer correlates with suppression of the hepatic phenotype and gain of metastatic properties. Oncogene. Oct. 8, 2009;28(40):3526-36. doi: 10.1038/onc.2009.211. Epub Jul. 20, 2009.

Cruz et al., The promise of gene therapy for the treatment of alpha-1 antitrypsin deficiency. Pharmacogenomics. Sep. 2007;8(9):1191-8.
Csak et al., MicroRNA-122 regulates hypoxia-inducible factor-1 and vimentin in hepatocytes and correlates with fibrosis in diet-induced steatohepatitis. Liver Int. Feb. 2015;35(2):532-41. doi: 10.1111/liv.12633. Epub Jul. 28, 2014.
Czech, MicroRNAs as therapeutic targets. N Engl J Med. Mar. 16, 2006;354(11):1194-5.
Davidoee et al., Sex significantly influences transduction of murine liver by recombinant adeno-associated viral vectors through an androgen-dependent pathway. Blood. Jul. 15, 2003;102(2):480-8. Epub Mar. 13, 2003.
Davidson et al., Recombinant adeno-associated virus type 2, 4, and 5 vectors: transduction of variant cell types and regions in the mammalian central nervous system. Proc Natl Acad Sci U S A. Mar. 28, 2000;97(7):3428-32.
Daya et al., Gene therapy using adeno-associated virus vectors. Clin Microbiol Rev. Oct. 2008;21(4):583-93. doi: 10.1128/CMR.00008-08.
Di Giorgio et al., Non-cell autonomous effect of glia on motor neurons in an embryonic stem cell-based ALS model. Nat Neurosci. May 2007;10(5):608-14. Epub Apr. 15, 2007.
Dominov et al., A novel dysferlin mutant pseudoexon bypassed with antisense oligonucleotides. Ann Clin Transl Neurol. Sep. 2014;1(9):703-20. doi: 10.1002/acn3.96. Epub Sep. 27, 2014.
Donnelly et al., RNA toxicity from the ALS/FTD C9ORF72 expansion is mitigated by antisense intervention. Neuron. Oct. 16, 2013;80(Supplemental Information). 33 pages.
Duque et al., Intravenous administration of self-complementary AAV9 enables transgene delivery to adult motor neurons. Mol Ther. Jul. 2009;17(7):1187-96. doi: 10.1038/mt.2009.71. Epub Apr. 14, 2009.
Eberling et al., Results from a phase I safety trial of hAADC gene therapy for Parkinson disease. Neurology. May 20, 2008;70(21): 1980-3. doi: 10.1212/01.wnl.0000312381.29287.ff. Epub Apr. 9, 2008.
Ebert et al., MicroRNA sponges: competitive inhibitors of small RNAs in mammalian cells. Nat Methods. Sep. 2007;4(9):721-6. Epub Aug. 12, 2007.
Ehlert et al., Cellular toxicity following application of adeno-associated viral vector-mediated RNA interference in the nervous system. BMC Neurosci. Feb. 18, 2010;11:20.
Elmén et al., LNA-mediated microRNA silencing in non-human primates. Nature. Apr. 2008;452(17): 896-900.
Elmén et al.,b Antagonism of microRNA-122 in mice by systemically administered LNA-antimiR leads to up-regulation of a large set of predicted target mRNAs in the liver. Nucleic Acids Res. Mar. 2008;36(4):1153-62. Epub Dec. 23, 2007.
Esau et al., miR-122 regulation of lipid metabolism revealed by in vivo antisense targeting. Cell Metab. Feb. 2006;3(2):87-98.
Fabani et al., miR-122 targeting with LNA/2'-O-methyl oligonucleotide mixmers, peptide nucleic acids (PNA), and PNA-peptide conjugates. RNA. Feb. 2008;14(2):336-46. Epub Dec. 11, 2007.
Fechner et al., Cardiac-targeted RNA interference mediated by an AAV9 vector improves cardiac function in coxsackievirus B3 cardiomyopathy. J Mol Med (Berl). Sep. 2008;86(9):987-97. doi: 10.1007/s00109-008-0363-x. Epub Jun. 12, 2008.
Feigin et al., Modulation of metabolic brain networks after subthalamic gene therapy for Parkinson's disease. Proc Natl Acad Sci U S A. Dec. 4, 2007;104(49):19559-64. Epub Nov. 27, 2007.
Fischer et al., Successful transgene expression with serial doses of aerosolized rAAV2 vectors in rhesus macaques. Mol Ther. Dec. 2003;8(6):918-26.
Fisher et al., Transduction with recombinant adeno-associated virus for gene therapy is limited by leading-strand synthesis. J Virol. Jan. 1996;70(1):520-32.
Flotte et al., Gene therapy for alpha-1 antitrypsin deficiency. Hum Mol Genet. Apr. 15, 2011;20(R1):R87-92. doi: 10.1093/hmg/ddr156. Epub Apr. 16, 2011.
Flotte et al., Phase I trial of intramuscular injection of a recombinant adeno-associated virus alpha 1-antitrypsin (rAAV2-CB-hAAT) gene vector to AAT-deficient adults. Hum Gene Ther. Jan. 2004;15(1):93-128.

(56) References Cited

OTHER PUBLICATIONS

Forman et al., A search for conserved sequences in coding regions reveals that the let-7 microRNA targets Dicer within its coding sequence. Proc Natl Acad Sci U S A. Sep. 30, 2008;105(39):14879-84. doi: 10.1073/pnas.0803230105. Epub Sep. 23, 2008.
Foust et al., Intravascular AAV9 preferentially targets neonatal-neurons and adult-astrocytes. Nature Biotechnology, 27; 59-65 2009.
Foust et al., Rescue of the spinal muscular atrophy phenotype in a mouse model by early postnatal delivery of SMN. Nat Biotechnol. Mar. 2010;28(3):271-4. doi: 10.1038/nbt.1610. Epub Feb. 28, 2010.
Fraldi et al., Functional correction of CNS lesions in an MPS-IIIA mouse model by intracerebral AAV-mediated delivery of sulfamidase and SUMF1 genes. Hum Mol Genet. Nov. 15, 2007;16(22):2693-702. Epub Aug. 27, 2007.
Fu et al., Self-complementary adeno-associated virus serotype 2 vector: global distribution and broad dispersion of AAV-mediated transgene expression in mouse brain. Mol Ther. Dec. 2003;8(6):911-7.
Gadalla et al., Improved survival and reduced phenotypic severity following AAV9/MECP2 gene transfer to neonatal and juvenile male Mecp2 knockout mice. Mol Ther. Jan. 2013;21(1):18-30. doi:10.1038/mt.2012.200. Epub Sep. 25, 2012.
Gao et al., Erythropoietin gene therapy leads to autoimmune anemia in macaques. Blood. May 1, 2004;103(9):3300-2. Epub Dec. 24, 2003.
Gao et al., Inadvertent gene transfer of co-packaged rep and cap sequences during the production of AAV vector and its potential impact on vector performance. Molecular Therapy. May 2008; 16(Suppl. 1):S105-S106. Abstract 279.
Gao et al., Novel adeno-associated viruses from rhesus monkeys as vectors for human gene therapy. Proc Natl Acad Sci U S A. Sep. 3, 2002;99(18):11854-9. Epub Aug. 21, 2002.
Gao et al., RAAV-mediated targeting in adult mice and its potential in generating animal models of tissue-specific somatic transgenics or knock down. Molecular Therapy. May 2008;16(1):S118-S119. Abstract 316.
GENBANK Submission; NCBI, Accession No. AAS99264; Gao et al.; Jun. 24, 2004.
GENBANK Submission; NCBI, Accession No. AY530579.10; 2004.
Gentner et al., Stable knockdown of microRNA in vivo by lentiviral vectors. Nat Methods. Jan. 2009;6(1):63-6. doi: 10.1038/nmeth.1277. Epub Nov. 30, 2008.
Georgiadis et al., AAV-mediated knockdown of peripherin-2 in vivo using miRNA-based hairpins. Gene Ther. Apr. 2010;17(4):486-93. doi: 10.1038/gt.2009.162. Epub Dec. 10, 2009.
Girard et al., miR-122, a paradigm for the role of microRNAs in the liver. J Hepatol. Apr. 2008;48(4):648-56. doi: 10.1016/j.jhep.2008.01.019. Epub Feb. 12, 2008.
Gramantieri et al., Cyclin G1 is a target of miR-122a, a microRNA frequently down-regulated in human hepatocellular carcinoma. Cancer Res. Jul. 1, 2007;67(13):6092-9.
Grimm et al., Fatality in mice due to oversaturation of cellular microRNA/short hairpin RNA pathways. Nature. May 25, 2006;441(7092):537-41.
Grimm, Small silencing RNAs: state-of-the-art. Adv Drug Deliv Rev. Jul. 25, 2009;61(9):672-703. doi: 10.1016/j.addr.2009.05.002. Epub May 7, 2009.
Haraguchi et al., Vectors expressing efficient RNA decoys achieve the long-term suppression of specific microRNA activity in mammalian cells. Nucleic Acids Res. Apr. 2009;37(6):e43. doi: 10.1093/nar/gkp040. Epub Feb. 17, 2009.
Haussecker et al., miR-122 continues to blaze the trail for microRNA therapeutics. Mol Ther. Feb. 2010;18(2):240-2. doi: 10.1038/mt.2009.313.
Hernandez et al., Latent adeno-associated virus infection elicits humoral but not cell-mediated immune responses in a nonhuman primate model. J Virol. Oct. 1999;73(10):8549-58.

Horwich et al., Design and delivery of antisense oligonucleotides to block microRNA function in cultured Drosophila and human cells. Nat Protoc. 2008;3(10):1537-49. doi: 10.1038/nprot.2008.145.
Hsu et al., Essential metabolic, anti-inflammatory, and anti-tumorigenic functions of miR-122 in liver. J Clin Invest. Aug. 2012;122(8):2871-83. doi:10.1172/JCI63539. Epub Jul. 23, 2012.
Hutvágner et al., Sequence-specific inhibition of small RNA function. PLoS Biol. Apr. 2004;2(4):E98. Epub Feb. 24, 2004.
Iida et al., Systemic Delivery of Tyrosine-Mutant AAV Vectors Results in Robust Transduction of Neurons in Adult Mice. BioMed Res Int. 2013;2013.
Jakobsson et al., Lentiviral vectors for use in the central nervous system. Mol Ther. Mar. 2006;13(3):484-93. Epub Jan. 3, 2006.
Johnson et al., RAS is regulated by the let-7 microRNA family. Cell. Mar. 11, 2005;120(5):635-47.
Kaspar et al., Retrograde viral delivery of IGF-1 prolongs survival in a mouse ALS model. Science. Aug. 8, 2003;301(5634):839-42.
Koornneef et al., Apolipoprotein B knockdown by AAV-delivered shRNA lowers plasma cholesterol in mice. Mol Ther. Apr. 2011;19(4):731-40. doi:10.1038/mt.2011.6. Epub Feb. 8, 2011.
Kota et al., AAV8-Mediated Delivery of miR-26a inhibits cancer cell proliferation and induces tumor-specific apoptosis in a liver cancer model. Mol. Therapy. May 2009. 17(1):S300. Abstract 783.
Kota et al., Therapeutic microRNA delivery suppresses tumorigenesis in a murine liver cancer model. Cell. Jun. 12, 2009;137(6):1005-17. doi: 10.1016/j.cell.2009.04.021.
Kotin et al., Organization of adeno-associated virus DNA in latently infected Detroit 6 cells. Virology. Jun. 1989;170(2):460-7.
Kotin et al., Site-specific integration by adeno-associated virus. Proc Natl Acad Sci U S A. Mar. 1990;87(6):2211-5.
Krützfeldt et al., Silencing of microRNAs in vivo with 'antagomirs'. Nature. Dec. 1, 2005;438(7068):685-9. Epub Oct. 30, 2005.
Kutay et al., Downregulation of miR-122 in the rodent and human hepatocellular carcinomas. J Cell Biochem. Oct. 15, 2006;99(3):671-8.
Lanford et al., Therapeutic silencing of microRNA-122 in primates with chronic hepatitis C virus infection. Science. Jan. 8, 2010;327(5962):198-201. Epub Dec. 3, 2009.
Lewis et al., Conserved seed pairing, often flanked by adenosines, indicates that thousands of human genes are microRNA targets. Cell. Jan. 14, 2005;120(1):15-20.
Lewis et al., Prediction of mammalian microRNA targets. Cell. Dec. 26, 2003;115(7):787-98.
Li et al., Efficient and Targeted Transduction of Nonhuman Primate Liver With Systemically Delivered Optimized AAV3B Vectors. Mol Ther. Dec. 2015;23(12):1867-76. doi: 10.1038/mt.2015.174. Epub Sep. 25, 2015.
Li et al., Intronic microRNA: discovery and biological implications. DNA Cell Biol. Apr. 2007;26(4):195-207.
Li et al., Protein trans-splicing as a means for viral vector-mediated in vivo gene therapy. Hum Gene Ther. Sep. 2008;19(9):958-64. doi: 10.1089/hum.2008.009.
Liu et al., Altered microRNA expression following traumatic spinal cord injury. Exp Neurol. Oct. 2009;219(2):424-9. doi: 10.1016/j.expneurol.2009.06.015. Epub Jul. 1, 2009.
Liu et al., Identification of a novel loss-of-function C9orf72 splice site mutation in a patient with amyotrophic lateral sclerosis. Neurobiol Aging. Nov. 2016;47:219.e1-219.e5. doi: 10.1016/j.neurobiolaging.2016.07.027. Epub Aug. 8, 2016.
Lowenstein, Crossing the rubicon. Nat Biotechnol. Jan. 2009;27(1):42-4.
Loya et al., Transgenic microRNA inhibition with spatiotemporal specificity in intact organisms. Nat Methods. Dec. 2009;6(12):897-903. doi: 10.1038/nmeth.1402. Epub Nov. 15, 2009.
Lux et al., Green fluorescent protein-tagged adeno-associated virus particles allow the study of cytosolic and nuclear trafficking. J Virol. Sep. 2005;79(18):11776-87.
Lynn, Meta-regulation: microRNA regulation of glucose and lipid metabolism. Trends Endocrinol Metab. Nov. 2009;20(9):452-9. doi: 10.1016/j.tem.2009.05.007. Epub Sep. 30, 2009.
Ma et al., Therapeutic silencing of miR-10b inhibits metastasis in a mouse mammary tumor model. Nat Biotechnol. Apr. 2010;28(4):341-7. doi: 10.1038/nbt.1618. Epub Mar. 28, 2010.

(56) References Cited

OTHER PUBLICATIONS

Maguire et al., Directed evolution of adeno-associated virus for glioma cell transduction. J Neurooncol. Feb. 2010;96(3):337-47. doi:10.1007/s11060-009-9972-7. Epub Jul. 19, 2009.
Maguire et al., Gene therapy for the nervous system: challenges and new strategies. Neurotherapeutics. Oct. 2014;11(4):817-39. doi: 10.1007/s13311-014-0299-5.
Mandel et al., Recombinant adeno-associated viral vectors as therapeutic agents to treat neurological disorders. Mol Ther. Mar. 2006;13(3):463-83. Epub Jan. 18, 2006.
Manfredsson et al., AAV9: a potential blood-brain barrier buster. Mol Ther. Mar. 2009;17(3):403-5.
Matalon et al., Adeno-associated virus-mediated aspartoacylase gene transfer to the brain of knockout mouse for canavan disease. Mol Ther. May 2003;7(5 Pt 1):580-7.
McBride et al., Artificial miRNAs mitigate shRNA-mediated toxicity in the brain: implications for the therapeutic development of RNAi. Proc Natl Acad Sci U S A. Apr. 15, 2008;105(15):5868-73. Epub Apr. 8, 2008.
McCarty et al., Adeno-associated virus terminal repeat (TR) mutant generates self-complementary vectors to overcome the rate-limiting step to transduction in vivo. Gene Ther. Dec. 2003;10(26):2112-8.
McCarty et al., Integration of adeno-associated virus (AAV) and recombinant AAV vectors. Annu Rev Genet. 2004;38:819-45.
McCarty et al., Self-complementary recombinant adeno-associated virus (scAAV) vectors promote efficient transduction independently of DNA synthesis. Gene Ther. Aug. 2001;8(16):1248-54.
McCarty, Self-complementary AAV vectors; advances and applications. Mol Ther. Oct. 2008;16(10):1648-56. Epub Aug. 5, 2008.
McCurdy et al., Sustained normalization of neurological disease after intracranial gene therapy in a feline model. Sci Transl Med. Apr. 9, 2014;6(231):231ra48. doi: 10.1126/scitranslmed.3007733.
Meijer et al., Controlling brain tumor growth by intraventricular administration of an AAV vector encoding IFN-beta. Cancer Gene Ther. Aug. 2009;16(8):664-71. doi: 10.1038/cgt.2009.8. Epub Feb. 6, 2009.
Meister et al., Sequence-specific inhibition of microRNA- and siRNA-induced RNA silencing. RNA. Mar. 2004;10(3):544-50.
Mietzsch et al., OneBac 2.0: Sf9 Cell Lines for Production of AAV5 Vectors with Enhanced Infectivity and Minimal Encapsidation of Foreign DNA. Hum Gene Ther. Oct. 2015;26(10):688-97. doi:10.1089/hum.2015.050. Epub Aug. 6, 2015.
MiRBase accession No. MI0000472. Last accessed on May 18, 2018 at http://www.mirbase.org/cgi-bin/mirna_entry.pl?acc=MI0000472.
Moffett et al., N-Acetylaspartate in the CNS: from neurodiagnostics to neurobiology. Prog Neurobiol. Feb. 2007;81(2):89-131. Epub Jan. 5, 2007.
Moss et al., Repeated adeno-associated virus serotype 2 aerosol-mediated cystic fibrosis transmembrane regulator gene transfer to the lungs of patients with cystic fibrosis: a multicenter, double-blind, placebo-controlled trial. Chest. Feb. 2004;125(2):509-21.
Mueller et al., Development of Simultaneous Gene Augmentation and Reduction of Mutant Gene Expression with a Single Recombinant AAV for Alpha-1 Antitrypsin Disease. Molecular Therapy May 2009;17(1):S391-S392. Abstract 1030.
Mueller et al., Sustained miRNA-mediated knockdown of mutant AAT with simultaneous augmentation of wild-type AAT has minimal effect on global liver miRNA profiles. Mol Ther. Mar. 2012;20(3):590-600. Epub Jan. 17, 2012.
Mueller et al., Using rAAV Delivered miRNAs to Knockdown Misfolded Human Alpha 1 Antitrypsin in a Transgenic Mouse Model. Molecular Therapy May 2010;18(1):S21. Abstract 51.
O'Reilly et al., RNA interference-mediated suppression and replacement of human rhodopsin in vivo. Am J Hum Genet. Jul. 2007;81(1):127-35. Epub May 23, 2007.
Passini et al., CNS-targeted gene therapy improves survival and motor function in a mouse model of spinal muscular atrophy. J Clin Invest. Apr. 2010;120(4):1253-64. doi: 10.1172/JCI41615. Epub Mar. 15, 2010.
Pertin et al., Efficacy and specificity of recombinant adeno-associated virus serotype 6 mediated gene transfer to drg neurons through different routes of delivery. Poster sessions. Eur J. Pain. 2009;13:S74. Abstract 229.
Pribadi et al., CRISPR-Cas9 targeted deletion of the C9orf72 repeat expansion mutation corrects cellular phenotypes in patient-derived iPS cells. Preprint published May 2, 2016.
Ralph et al., Silencing mutant SOD1 using RNAi protects against neurodegeneration and extends survival in an ALS model. Nat Med. Apr. 2005;11(4):429-33. Epub Mar. 13, 2005.
Raoul et al., Lentiviral-mediated silencing of SOD1 through RNA interference retards disease onset and progression in a mouse model of ALS. Nat Med. Apr. 2005;11(4):423-8. Epub Mar. 13, 2005.
Renton et al., State of play in amyotrophic lateral sclerosis genetics. Nat Neurosci. 2014;17(1):17-23.doi:10.1038/nn.3584.
Sambrook et al., "Molecular Cloning. A Laboratory Manual", 2d ed., Cold Spring Harbor Laboratory, New York (1989).
Schnepp et al., Characterization of adeno-associated virus genomes isolated from human tissues. J Virol. Dec. 2005;79(23):14793-803.
Sen et al., Micromanaging vascular biology: tiny microRNAs play big band. J Vasc Res. 2009;46(6):527-40. doi: 10.1159/000226221. Epub Jun. 30, 2009.
Sin et al., Gene silencing efficiency and INF-? induction effects of splicing miRNA 155-based artificial miRNA with pre-miRNA stem-loop structures. Biochem Genet. Feb. 2012;50(1-2):112-21. doi: 10.1007/s10528-011-9476-y. Epub Nov. 27, 2011.
Snyder et al., Comparison of adeno-associated viral vector serotypes for spinal cord and motor neuron gene delivery. Hum Gene Ther. Sep. 2011;22(9):1129-35. doi: 10.1089/hum.2011.008. Epub Jul. 25, 2011.
Sondhi et al., Enhanced survival of the LINCL mouse following CLN2 gene transfer using the rh.10 rhesus macaque-derived adeno-associated virus vector. Mol Ther. Mar. 2007;15(3):481-91. Epub Dec. 19, 2006.
Stoica et al., Targeting Human SOD1 Using AAV mediated RNAi in a mouse model of amyotrophic lateral sclerosis. Mol ther. Jun. 2013;21(1):S149.
Storek et al., Intrathecal long-term gene expression by self-complementary adeno-associated virus type 1 suitable for chronic pain studies in rats. Mol Pain. Jan. 3, 2006;2:4.
Storkebaum et al., Treatment of motoneuron degeneration by intracerebroventricular delivery of VEGF in a rat model of ALS. Nat Neurosci. Jan. 2005;8(1):85-92. Epub Nov. 28, 2004.
Suckau et al., 851. The Effect of Genome Size and Design of scAAV Vectors on Efficiency of shRNA Expression and Gene Knockdown. May 1, 2007;15(1):S325.
Tanimizu et al., Downregulation of miR122 by grainyhead-like 2 restricts the hepatocytic differentiation potential of adult liver progenitor cells. Development. Dec. 2014;141(23):4448-56. doi:10.1242/dev.H3654. Epub Nov. 18, 2014.
Tenenbaum et al., Recombinant AAV-mediated gene delivery to the central nervous system. J Gene Med. Feb. 2004;6 Suppl 1:S212-22.
Tokumaru et al., let-7 regulates Dicer expression and constitutes a negative feedback loop. Carcinogenesis. Nov. 2008;29(11):2073-7. doi: 10.1093/carcin/bgn187. Epub Aug. 11, 2008.
Tomar et al., Use of adeno-associated viral vector for delivery of small interfering RNA. Oncogene. Aug. 28, 2003;22(36):5712-5.
Towne et al., Systemic AAV6 delivery mediating RNA interference against SOD1: neuromuscular transduction does not alter disease progression in fALS mice. Mol Ther. Jun. 2008;16(6):1018-25. doi:10.1038/mt.2008.73. Epub Apr. 15, 2008.
Truong et al., Development of an intein-mediated split-Cas9 system for gene therapy. Nucleic Acids Res. Jul. 27, 2015;43(13):6450-8. doi: 10.1093/nar/gkv601. Epub Jun. 16, 2015.
Tsai et al., MicroRNA-122, a tumor suppressor microRNA that regulates intrahepatic metastasis of hepatocellular carcinoma. Hepatology. May 2009;49(5):1571-82. doi: 10.1002/hep.22806.
U.S. Appl. No. 15/098,833, filed Apr. 14, 2016, Flotte et al.
U.S. Appl. No. 15/120,294, filed Aug. 19, 2016, Gao et al.
U.S. Appl. No. 15/316,027, filed Dec. 2, 2016, Brown et al.
U.S. Appl. No. 15/367,708, filed Dec. 2, 2016, Gao et al.
U.S. Appl. No. 15/423,702, filed Feb. 3, 2017, Gao et al.
U.S. Appl. No. 15/423,720, filed Feb. 3, 2017, Gao et al.

(56) References Cited

OTHER PUBLICATIONS

U.S. Appl. No. 15/516,582, filed Apr. 3, 2017, Esteves et al.
U.S. Appl. No. 15/516,585, filed Apr. 3, 2017, Esteves et al.
U.S. Appl. No. 15/567,847, filed Oct. 19, 2017, Esteves et al.
U.S. Appl. No. 15/568,650, filed Oct. 23, 2017, Gao et al.
U.S. Appl. No. 15/578,994, filed Dec. 1, 2017, Cataltepe.
U.S. Appl. No. 15/613,646, filed Jun. 5, 2017, Gao et al.
U.S. Appl. No. 15/747,801, filed Jan. 26, 2018, Fitzgerald et al.
UNIPROT Submission; Accession No. A8IGP7; Nov. 13, 2013.
UNIPROT Submission; Accession No. H3GK32; Feb. 6, 2013.
UNIPROT Submission; Accession No. T2BRA8; Nov. 13, 2013.
Vandenberghe et al., Heparin binding directs activation of T cells against adeno-associated virus serotype 2 capsid. Nat Med. Aug. 2006;12(8):967-71. Epub Jul. 16, 2006.
Vandenberghe et al., Tailoring the AAV vector capsid for gene therapy. Gene Ther. Mar. 2009;16(3):311-9. Epub Dec. 4, 2008.
Vandendriessche et al., Efficacy and safety of adeno-associated viral vectors based on serotype 8 and 9 vs. lentiviral vectors for hemophilia B gene therapy. J Thromb Haemost. Jan. 2007;5(1):16-24. Epub Sep. 26, 2006.
Vaucheret et al., The action of ARGONAUTE1 in the miRNA pathway and its regulation by the miRNA pathway are crucial for plant development. Genes Dev. May 15, 2004;18(10):1187-97. Epub May 6, 2004.
Vermeulen et al., Double-stranded regions are essential design components of potent inhibitors of RISC function. RNA. May 2007;13(5):723-30. Epub Mar. 30, 2007.
Vulchanova et al., Differential adeno-associated virus mediated gene transfer to sensory neurons following intrathecal delivery by direct lumbar puncture. Mol Pain. May 28, 2010;6:31. doi: 10.1186/1744-8069-6-31.
Waldman et al., Applications of microRNA in cancer: Exploring the advantages of miRNA. Clin Transl Sci. Jun. 2009;2(3):248-9. doi: 10.1111/j.1752-8062.2009.00110.x.
Wang et al., Neuroprotective effects of glial cell line-derived neurotrophic factor mediated by an adeno-associated virus vector in a transgenic animal model of amyotrophic lateral sclerosis. J Neurosci. Aug. 15, 2002;22(16):6920-8.
Wang et al., Rescue and replication of adeno-associated virus type 2 as well as vector DNA sequences from recombinant plasmids containing deletions in the viral inverted terminal repeats: selective encapsidation of viral genomes in progeny virions. J Virol. Mar. 1996;70(3):1668-77.
Wang et al., Somatically Repairing Compound Heterozygous Recessive Mutations by Chromosomal Cut-and-Paste for in Vivo Gene Therapy. May 2016. 24(1):S289. Abstract 733.
Wang et al., Sustained correction of disease in naive and AAV2-pretreated hemophilia B dogs: AAV2/8-mediated, liver-directed gene therapy. Blood. Apr. 15, 2005;105(8):3079-86. Epub Jan. 6, 2005.
Wang et al., The design of vectors for RNAi delivery system. Curr Pharm Des. 2008;14(13):1327-40.
Wang et al., The potential of adeno-associated viral vectors for gene delivery to muscle tissue. Expert Opin Drug Deliv. Mar. 2014;11(3):345-64. doi: 10.1517/17425247.2014.871258. Epub Jan. 3, 2014.
Wang et al., Therapeutic gene silencing delivered by a chemically modified small interfering RNA against mutant SOD1 slows amyotrophic lateral sclerosis progression. J Biol Chem. Jun. 6, 2008;283(23):15845-52. doi: 10.1074/jbc.M800834200. Epub Mar. 26, 2008.
Wang et al., Widespread spinal cord transduction by intrathecal injection of rAAV delivers efficacious RNAi therapy for amyotrophic lateral sclerosis. Hum Mol Genet. Feb. 1, 2014;23(3):668-81. doi: 10.1093/hmg/ddt454. Epub Sep. 18, 2013.
Watson et al., Intrathecal administration of AAV vectors for the treatment of lysosomal storage in the brains of MPS I mice. Gene Ther. Jun. 2006;13(11):917-25.
Wein et al., Efficient bypass of mutations in dysferlin deficient patient cells by antisense-induced exon skipping. Hum Mutat. Feb. 2010;31(2):136-42. doi: 10.1002/humu.21160.

Weismann et al., Systemic AAV9 gene transfer in adult GM1 gangliosidosis mice reduces lysosomal storage in CNS and extends lifespan. Hum Mol Genet. Aug. 1, 2015;24(15):4353-64. doi: 10.1093/hmg/ddv168. Epub May 10, 2015.
Weismann, Approaches and Considerations Towards a Safe and Effective Adeno-Associated Virus Mediated Therapeutic Intervention for GM 1-Gangliosidosis: A Dissertation. University Massachusetts Medical School. Aug. 5, 2014.
Xia et al., Allele-specific RNAi selectively silences mutant SOD1 and achieves significant therapeutic benefit in vivo. Neurobiol Dis. Sep. 2006;23(3):578-86. Epub Jul. 20, 2006.
Xie et al., 676. DNA Sequences Encoding shRNAs Can Replace Mutant ITR in scAAV Genome for Efficient Replication and Packaging and Transcribe shRNAs by pol III Promoter Activity of wt ITR for Efficient Gene Silencing Mol Therapy. May 2015;23(1):S269.
Xie et al., Characterization of positioning effect of pol III-shRNA transcription unit in scAAV vector genome on the packaging efficiency and functionality of shRNA silencing. Molecular Therapy. May 2010;18(1): S262. Abstract 671.
Xie et al., Isolation of transcriptionally active novel AAV capsid sequences from chimpanzee tissues for vector development. Meeting Abstract: 12th Annual Meeting of the American Society of Gene Therapy. May 1, 2009. Abstract 91.
Xie et al., MicroRNA regulated tissue specific transduction by rAAV vector. Molecular Therapy. May 2009; 17(1): S279. Abstract 732.
Xie et al., MicroRNA-regulated, systemically delivered rAAV9: a step closer to CNS-restricted transgene expression. Mol Ther. Mar. 2011;19(3):526-35. doi: 10.1038/mt.2010.279. Epub Dec. 21, 2010.
Xie et al., rAAV-mediated delivery of micro RNA scavengers leads to efficient and stable knockdown of cognate micro RNAs, upregulation of their natural target genes and phenotypic changes in mice. Molecular Therapy. May 2010;18(1): S140. Abstract362.
Xie et al., Short DNA Hairpins Compromise Recombinant Adeno-Associated Virus Genome Homogeneity. Mol Ther. Jun. 7, 2017;25(6):1363-1374. doi: 10.1016/j.ymthe.2017.03.028. Epub Apr. 24, 2017.
Xu et al., Delivery of MDR1 small interfering RNA by self-complementary recombinant adeno-associated virus vector. Mol Ther. Apr. 2005;11(4):523-30.
Yamanaka et al., Astrocytes as determinants of disease progression in inherited amyotrophic lateral sclerosis. Nat Neurosci. Mar. 2008;11(3):251-3. doi: 10.1038/nn2047. Epub Feb. 3, 2008.
Yang et al., The muscle-specific microRNA miR-1 regulates cardiac arrhythmogenic potential by targeting GJA1 and KCNJ2. Nat Med. Apr. 2007;13(4):486-91. Epub Apr. 1, 2007. Erratum in: Nat Med. Dec. 2011;17(12):1693.
Yu et al., let-7 regulates self renewal and tumorigenicity of breast cancer cells. Cell. Dec. 14, 2007;131(6):1109-23.
Zhang et al., Characterization of 12 AAV vectors for intravascular delivery to target CNS and detarget non-CNS tissues by mirna regulation: implications in treatment of canavan disease. Molecular Therapy. May 2010; 18(1): S174. Abstract 450.
Zhong et al., Chimpanzee-derived novel natural variants of aav9: vector development and interrogation of correlations between capsid structure and vector biology. Molecular Therapy. May 2010;18(1): S24. Abstract 58.
Zincarelli et al., Analysis of AAV serotypes 1-9 mediated gene expression and tropism in mice after systemic injection. Mol Ther. Jun. 2008;16(6):1073-80. doi: 10.1038/mt.2008.76. Epub Apr. 15, 2008.
Zolotukhin et al., Production and purification of serotype 1, 2, and 5 recombinant adeno-associated viral vectors. Methods. Oct. 2002;28(2):158-67.
Zu et al., RAN proteins and RNA foci from antisense transcripts in C9ORF72 ALS and frontotemporal dementia. Proc Natl Acad Sci U S A. 2013;110(51):E4968-E4977. doi:10.1073/pnas.1315438110.
Gaj et al., Genome Engineering Using Adeno-associated Virus: Basic and Clinical Research Applications. Mol Ther. Mar. 2016;24(3):458-64. doi: 10.1038/mt.2015.151. Epub Sep. 16, 2015.
Hinderer et al., Widespread gene transfer in the central nervous system of cynomolgus macaques following delivery of AAV9 into

(56) References Cited

OTHER PUBLICATIONS the cisterna magna. Mol Ther Methods Clin Dev. Dec. 10, 2014;1:14051. doi: 10.1038/mtm.2014.51. PMID: 26052519; PMCID: PMC4448732.

Kubodera et al., In vivo application of an RNAi strategy for the selective suppression of a mutant allele. Hum Gene Ther. Jan. 2011;22(1):27-34. doi: 10.1089/hum.2010.054. PMID: 20649474.

Lebedeva et al., Phosphorothioate Oligodeoxynucleotides as Inhibitors of Gene Expression: Antisense and Non-Antisense Effects. In: Rabbani, L.E. (eds) Applications of Antisense Therapies to Restenosis. Perspectives in Antisense Science. 1999; 3:99-118. https://doi.org/10.1007/978-1-4615-5183-6_6.

Lisowski et al., Adeno-associated virus serotypes for gene therapeutics. Curr Opin Pharmacol. Oct. 2015;24:59-67. doi: 10.1016/j.coph.2015.07.006. Epub Aug. 25, 2015.

\* cited by examiner

```
Wild-type  atggcgacgaaggccgtgtgcgtgctgaagggcgacggcccagtgcagggcatcatcaat  60
Hardened   atggcgacgaaggccgtgtgcgtgctgaagggcgacggcccagtgcagggcatcatcaat  60
           ************************************************************

Wild-type  ttcgagcagaaggaaagtaatggaccagtgaaggtgtggggaagcattaaaggactgact  120
Hardened   ttcgagcagaaggaaagtaatggaccagtgaaggtgtggggaagcattaaaggactgact  120
           ************************************************************

Wild-type  gaaggcctgcatggattccatgttcatgagtttggagataatacagcaggctgtaccagt  180
Hardened   gaaggcctgcacggctttcacgtccacgagtttggagataatacagcaggctgtaccagt  180
           *********** ** ** ** ** ** ********************************

Wild-type  gcaggtcctcactttaatcctctatccagaaaacacggtgggccaaaggatgaagagagg  240
Hardened   gcaggtcctcactttaatcctctatccagaaaacacggtgggccaaaggatgaagagagg  240
           ************************************************************

Wild-type  catgttggagacttgggcaatgtgactgctgacaaagatggtgtggccgatgtgtctatt  300
Hardened   catgttggagacttgggcaatgtgactgctgacaaagatggtgtggccgatgtgtctatt  300
           ************************************************************

Wild-type  gaagattctgtgatctcactctcaggagaccattgcatcattggccgcacactggtggtc  360
Hardened   gaagattctgtgatctcactctcaggagaccattgcatcattggccgcacactggtggtc  360
           ************************************************************

Wild-type  catgaaaaagcagatgacttgggcaaaggtggaaatgaagaaagtacaaagacaggaaac  420
Hardened   catgaaaaagcagatgacttgggcaaaggtggaaatgaagaaagtacaaagacaggaaac  420
           ************************************************************

Wild-type  gctggagtcgtttggcttgtggtgtaattgggatcgcccaataa  465
Hardened   gctggagtcgtttggcttgtggtgtaattgggatcgcccaataa  465
           *******************************************
```

FIG. 9

SEQUENCE LISTING

```
<160> NUMBER OF SEQ ID NOS: 17

<210> SEQ ID NO 1
<211> LENGTH: 465
<212> TYPE: DNA
<213> ORGANISM: Homo sapiens

<400> SEQUENCE: 1
atggcgacga aggccgtgtg cgtgctgaag ggcgacggcc cagtgcaggg catcatcaat      60
ttcgagcaga aggaaagtaa tggaccagtg aaggtgtggg gaagcattaa aggactgact     120
gaaggcctgc atggattcca tgttcatgag tttggagata atacagcagg ctgtaccagt     180
gcaggtcctc actttaatcc tctatccaga aacacggtg  ggccaaagga tgaagagagg      240
catgttggag acttgggcaa tgtgactgct gacaaagatg gtgtggccga tgtgtctatt     300
gaagattctg tgatctcact ctcaggagac cattgcatca ttggccgcac actggtggtc     360
catgaaaaag cagatgactt gggcaaaggt ggaaatgaag aaagtacaaa gacaggaaac     420
gctggaagtc gtttggcttg tggtgtaatt gggatcgccc aataa                     465
```

```
<210> SEQ ID NO 2
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 2
ctgcatggat tccatgttca t                                              21

<210> SEQ ID NO 3
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 3
gacgtaccta aggtacaagt a                                              21

<210> SEQ ID NO 4
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 4
ctgcatggat tccatgttca t                                              21

<210> SEQ ID NO 5
<211> LENGTH: 64
<212> TYPE: DNA
<213> ORGANISM: Artificial Sequence
<220> FEATURE:
<223> OTHER INFORMATION: Synthetic Polynucleotide

<400> SEQUENCE: 5
tgctgatgaa catggaatcc atgcaggttt tggccactga ctgacctgca tggtccatgt     60
tcat                                                                 64

<210> SEQ ID NO 6
<211> LENGTH: 64
<212> TYPE: DNA
<213> ORGANISM: Artificial Sequence
<220> FEATURE:
<223> OTHER INFORMATION: Synthetic Polynucleotide

<400> SEQUENCE: 6
atgaacatgg accatgcagg tcagtcagtg gccaaaacct gcatggattc catgttcatc     60
agca                                                                 64

<210> SEQ ID NO 7
<211> LENGTH: 465
<212> TYPE: DNA
<213> ORGANISM: Artificial Sequence
<220> FEATURE:
<223> OTHER INFORMATION: Synthetic Polynucleotide

<400> SEQUENCE: 7
atggcgacga aggccgtgtg cgtgctgaag ggcgacggcc cagtgcaggg catcatcaat     60
ttcgagcaga aggaaagtaa tggaccagtg aaggtgtggg gaagcattaa aggactgact     120
gaaggcctgc acggctttca cgtccacgag tttggagata tacagcagg ctgtaccagt     180
```

| | |
|---|---|
| gcaggtcctc actttaatcc tctatccaga aaacacggtg ggccaaagga tgaagagagg | 240 |
| catgttggag acttgggcaa tgtgactgct gacaaagatg gtgtggccga tgtgtctatt | 300 |
| gaagattctg tgatctcact ctcaggagac cattgcatca ttggccgcac actggtggtc | 360 |
| catgaaaaag cagatgactt gggcaaaggt ggaaatgaag aaagtacaaa gacaggaaac | 420 |
| gctggaagtc gtttggcttg tggtgtaatt gggatcgccc aataa | 465 |

<210> SEQ ID NO 8
<211> LENGTH: 5055
<212> TYPE: DNA
<213> ORGANISM: Artificial Sequence
<220> FEATURE:
<223> OTHER INFORMATION: Synthetic Polynucleotide

<400> SEQUENCE: 8

| | |
|---|---|
| ctctggtcgt tacataactt acggtaaatg gcccgcctgg ctgaccgccc aacgaccccc | 60 |
| gcccattgac gtcaataatg acgtatgttc ccatagtaac gccaataggg actttccatt | 120 |
| gacgtcaatg ggtggagtat ttacggtaaa ctgcccactt ggcagtacat caagtgtatc | 180 |
| atatgccaag tacgccccct attgacgtca atgacggtaa atggcccgcc tggcattatg | 240 |
| cccagtacat gaccttatgg gactttccta cttggcagta catctactcg aggccacgtt | 300 |
| ctgcttcact ctccccatct cccccccctc cccacccccca atttgtatt tatttatttt | 360 |
| ttaattattt tgtgcagcga tggggggcggg ggggggggg ggcgcgcgc caggcggggc | 420 |
| ggggcgggc gaggggcggg gcggggcgag gcggagaggt gcggcggcag ccaatcagag | 480 |
| cggcgcgctc cgaaagtttc cttttatggc gaggcggcgg cggcggcggc cctataaaaa | 540 |
| gcgaagcgcg cggcgggcgg gagcgggatc agccaccgcg gtggcggcct agagtcgacg | 600 |
| aggaactgaa aaaccagaaa gttaactggt aagtttagtc ttttgtctt ttatttcagg | 660 |
| tcccggatcc ggtggtggtg caaatcaaag aactgctcct cagtggatgt tgcctttact | 720 |
| tctaggcctg tacggaagtg ttacttctgc tctaaaagct gcggaattgt acccgcggcc | 780 |
| gcgtttaaac cctgcaggtc tagaaagctt atcgataccg tcgactagag ctcgctgatc | 840 |
| agcctcgact gtgccttcta gttgccagcc atctgttgtt tgcccctccc cgtgccttc | 900 |
| cttgaccctg gaaggtgcca ctcccactgt cctttcctaa taaaatgagg aaattgcatc | 960 |
| gcattgtctg agtaggtgtc attctattct ggggggtggg gtgggggcagg acagcaaggg | 1020 |
| ggaggattgg gaagacaata gcagggtaca agtaaagcgg ccctagcgtt tccggcgacg | 1080 |
| gtgctagact cgaggacggg gtgaactacg cctgaggatc cgatctttt ccctctgcca | 1140 |
| aaaattatgg ggacatcatg aagccccttg agcatctgac ttctggctaa taaaggaaat | 1200 |
| ttattttcat tgcaatagtg tgttggaatt ttttgtgtct ctcactcgga agcaattcgt | 1260 |
| tgatctgaat tcgaccacc cataatacc attaccctgg tagataagta gcatggcggg | 1320 |
| ttaatcatta actacaagga accccctagtg atggagttgg ccactccctc tctgcgcgct | 1380 |
| cgctcgctca ctgaggccgg gcgaccaaag gtcgcccgac gcccgggctt tgcccgggcg | 1440 |
| gcctcagtga gcgagcgagc gcgcagcctt aattaaccta attcactggc cgtcgtttta | 1500 |
| caacgtcgtg actgggaaaa ccctggcgtt acccaactta atcgccttgc agcacatccc | 1560 |
| cctttcgcca gctggcgtaa tagcgaagag gcccgcaccg atcgcccttc ccaacagttg | 1620 |
| cgcagcctga atggcgaatg ggacgcgccc tgtagcggcg cattaagcgc ggcgggtgtg | 1680 |
| gtggttacgc gcagcgtgac cgctacactt gccagcgccc tagcgcccgc tcctttcgct | 1740 |
| ttcttccctt cctttctcgc cacgttcgcc ggctttcccc gtcaagctct aaatcggggg | 1800 |

```
ctcccttag  ggttccgatt  tagtgcttta  cggcacctcg  accccaaaaa  acttgattag   1860
ggtgatggtt  cacgtagtgg  gccatcgccc  tgatagacgg  tttttcgccc  tttgacgttg   1920
gagtccacgt  tctttaatag  tggactcttg  ttccaaactg  gaacaacact  caaccctatc   1980
tcggtctatt  cttttgattt  ataagggatt  ttgccgattt  cggcctattg  gttaaaaaat   2040
gagctgattt  aacaaaaatt  taacgcgaat  tttaacaaaa  tattaacgct  tacaatttag   2100
gtggcacttt  tcggggaaat  gtgcgcggaa  ccctatttg  tttattttc  taaatacatt   2160 caaatatgta  tccgctcatg  agacaataac  cctgataaat  gcttcaataa  tattgaaaaa   2220
ggaagagtat  gagtattcaa  catttccgtg  tcgcccttat  tcccttttt  gcggcatttt   2280 gccttcctgt  ttttgctcac  ccagaaacgc  tggtgaaagt  aaaagatgct  gaagatcagt   2340
tgggtgcacg  agtgggttac  atcgaactgg  atctcaacag  cggtaagatc  cttgagagtt   2400
ttcgccccga  agaacgtttt  ccaatgatga  gcacttttaa  agttctgcta  tgtggcgcgg   2460
tattatcccg  tattgacgcc  gggcaagagc  aactcggtcg  ccgcatacac  tattctcaga   2520
atgacttggt  tgagtactca  ccagtcacag  aaaagcatct  tacggatggc  atgacagtaa   2580
gagaattatg  cagtgctgcc  ataaccatga  gtgataacac  tgcggccaac  ttacttctga   2640
caacgatcgg  aggaccgaag  gagctaaccg  cttttttgca  caacatgggg  gatcatgtaa   2700
ctcgccttga  tcgttgggaa  ccggagctga  atgaagccat  accaaacgac  gagcgtgaca   2760
ccacgatgcc  tgtagcaatg  gcaacaacgt  tgcgcaaact  attaactggc  gaactactta   2820
ctctagcttc  ccggcaacaa  ttaatagact  ggatggaggc  ggataaagtt  gcaggaccac   2880
ttctgcgctc  ggcccttccg  gctggctggt  ttattgctga  taaatctgga  gccggtgagc   2940
gtgggtctcg  cggtatcatt  gcagcactgg  ggccagatgg  taagccctcc  cgtatcgtag   3000
ttatctacac  gacggggagt  caggcaacta  tggatgaacg  aaatagacag  atcgctgaga   3060
taggtgcctc  actgattaag  cattggtaac  tgtcagacca  agtttactca  tatatacttt   3120
agattgattt  aaaacttcat  ttttaattta  aaaggatcta  ggtgaagatc  cttttttgata   3180 atctcatgac  caaaatccct  taacgtgagt  tttcgttcca  ctgagcgtca  gaccccgtag   3240
aaaagatcaa  aggatcttct  tgagatcctt  tttttctgcg  cgtaatctgc  tgcttgcaaa   3300
caaaaaaacc  accgctacca  gcggtggttt  gtttgccgga  tcaagagcta  ccaactcttt   3360
ttccgaaggt  aactggcttc  agcagagcgc  agataccaaa  tactgttctt  ctagtgtagc   3420
cgtagttagg  ccaccacttc  aagaactctg  tagcaccgcc  tacatacctc  gctctgctaa   3480
tcctgttacc  agtggctgct  gccagtggcg  ataagtcgtg  tcttaccggg  ttggactcaa   3540
gacgatagtt  accggataag  gcgcagcggt  cgggctgaac  ggggggttcg  tgcacacagc   3600
ccagcttgga  gcgaacgacc  tacaccgaac  tgagatacct  acagcgtgag  ctatgagaaa   3660
gcgccacgct  tcccgaaggg  agaaaggcgg  acaggtatcc  ggtaagcggc  agggtcggaa   3720
caggagagcg  cacgagggag  cttccagggg  gaaacgcctg  gtatctttat  agtcctgtcg   3780
ggtttcgcca  cctctgactt  gagcgtcgat  ttttgtgatg  ctcgtcaggg  ggcggagcc   3840 tatggaaaaa  cgccagcaac  gcggcctttt  tacggttcct  ggccttttgc  tggccttttg   3900
ctcacatgtt  ctttcctgcg  ttatcccctg  attctgtgga  taaccgtatt  accgcctttg   3960
agtgagctga  taccgctcgc  cgcagccgaa  cgaccgagcg  cagcgagtca  gtgagcgagg   4020
aagcggaaga  gcgcccaata  cgcaaaccgc  ctctccccgc  gcgttggccg  attcattaat   4080
gcagctgatt  ctaacgagga  aagcacgtta  tacgtgctcg  tcaaagcaac  catagtacgc   4140
```

| | |
|---|---|
| gccctgtagc ggcgcattaa gcgcggcggg tgtggtggtt acgcgcagcg tgaccgctac | 4200 |
| acttgccagc gccctagcgc ccgctccttt cgctttcttc ccttcctttc tcgccacgtt | 4260 |
| cgccggcttt ccccgtcaag ctctaaatcg ggggctccct ttagggttcc gatttagtgc | 4320 |
| tttacggcac ctcgacccca aaaaacttga ttagggtgat ggttcacgta gtgggccatc | 4380 |
| gccctgatag acggtttttc gccctttgac gttggagtcc acgttcttta atagtggact | 4440 |
| cttgttccaa actggaacaa cactcaaccc tatctcggtc tattcttttg atttataagg | 4500 |
| gatttttgccg atttcggcct attggttaaa aaatgagctg atttaacaaa aatttaacgc | 4560 |
| gaattttaac aaaatattaa cgcttacaat ttaaatattt gcttatacaa tcttcctgtt | 4620 |
| tttgggcctt ttctgattat caaccggggt acatatgatt gacatgctag ttttacgatt | 4680 |
| accgttcatc gccctgcgcg ctcgctcgct cactgaggcc gcccgggcaa agcccgggcg | 4740 |
| tcgggcgacc tttggtcgcc cggcctcagt gagcgagcga gcgcgcagag agggagtgga | 4800 |
| attctaaatt catatttgca tgtcgctatg tgttctggga aatcaccata aacgtgaaat | 4860 |
| gtctttggat ttgggaatct tataagttct gtatgagacc actcgcctgg aggcttgctg | 4920 |
| aaggctgtat gctgatgaac atggaatcca tgcaggtttt ggccactgac tgacctgcat | 4980 |
| ggtccatgtt catcaggaca caaggcctgt tactagcact cacatggaac aaatggcccct | 5040 |
| tttttctagt ggtac | 5055 |

<210> SEQ ID NO 9
<211> LENGTH: 3048
<212> TYPE: DNA
<213> ORGANISM: Artificial Sequence
<220> FEATURE:
<223> OTHER INFORMATION: Synthetic Polynucleotide

<400> SEQUENCE: 9

| | |
|---|---|
| tcaatattgg ccattagcca tattattcat tggttatata gcataaatca atattggcta | 60 |
| ttggccattg catacgttgt atctatatca taatatgtac atttatattg gctcatgtcc | 120 |
| aatatgaccg ccatgttggc attgattatt gactagttat taatagtaat caattacggg | 180 |
| gtcattagtt catagcccat atatggagtt ccgcgttaca taacttacgg taaatggccc | 240 |
| gcctggctga ccgcccaacg acccccgccc attgacgtca ataatgacgt atgttcccat | 300 |
| agtaacgcca atagggactt tccattgacg tcaatgggtg gagtatttac ggtaaactgc | 360 |
| ccacttggca gtacatcaag tgtatcatat gccaagtccg cccccctattg acgtcaatga | 420 |
| cggtaaatgg cccgcctggc attatgccca gtacatgacc ttacgggact ttcctacttg | 480 |
| gcagtacatc tacgtattag tcatcgctat taccatggtc gaggtgagcc ccacgttctg | 540 |
| cttcactctc cccatctccc cccctcccc accccaatt ttgtatttat ttatttttta | 600 |
| attattttgt gcagcgatgg gggcggggggg gggggggggg cgcgcgccag gcggggcggg | 660 |
| gcggggcgag gggcggggcg gggcgaggcg gagaggtgcg gcgcagcca atcagagcgg | 720 |
| cgcgctccga aagtttcctt ttatggcgag gcggcggcgg cggcggccct ataaaaagcg | 780 |
| aagcgcgcgg cgggcgggag tcgctgcgac gctgccttcg ccccgtgccc cgctccgccg | 840 |
| ccgcctcgcg ccgcccgccc cggctctgac tgaccgcgtt actcccacag gtgagcgggc | 900 |
| gggacggccc ttctcctccg ggctgtaatt agcgcttggt ttaatgacgg cttgtttctt | 960 |
| ttctgtggct gcgtgaaagc cttgagggc tccgggaggg cccttttgtgc ggggggggagc | 1020 |
| ggctcggggg gtgcgtgcgt gtgtgtgtgc gtggggagcg ccgcgtgcgg cccgcgctgc | 1080 |
| ccggcggctg tgagcgctgc gggcgcggcg cggggctttg tgcgctccgc agtgtgcgcg | 1140 |

```
aggggagcgc ggccgggggc ggtgcccgc ggtgcggggg gggctgcgag gggaacaaag    1200
gctgcgtgcg gggtgtgtgc gtggggggt gagcagggg tgtgggcgcg cggtcgggc    1260 tgtaaccccc ccctgcaccc ccctccccga gttgctgagc acggcccggc ttcgggtgcg    1320
gggctccgta cggggcgtgg cgcggggctc gccgtgccgg gcgggggtg gcggcaggtg    1380 ggggtgccgg gcggggcggg gccgcctcgg gccggggagg gctcggggga ggggcgcggc    1440
ggcccccgga gcgccggcgg ctgtcgaggc gcggcgagcc gcagccattg ccttttatgg    1500
taatcgtgcg agagggcgca gggacttcct ttgtcccaaa tctgtgcgga gccgaaatct    1560
gggaggcgcc gccgcacccc ctctagcggg cgcggggcga agcggtgcgg cgccggcagg    1620
aaggaaatgg gcggggaggg ccttcgtgcg tcgccgcgcc gccgtcccct tctccctctc    1680
cagcctcggg gctgtccgcg gggggacggc tgccttcggg ggggacgggg cagggcgggg    1740
ttcggcttct ggcgtgtgac cggcggctct agccggcgac cggtatgcat cctggaggct    1800
tgctgaaggc tgtatgctga tgaacatgga atccatgcag gtttttggcca ctgactgacc    1860 tgcatggtcc atgttcatca ggacacaagg cctgttacta gcactcacat ggaacaaatg    1920
gcccctagct cgcgatgcat ctagagcctc tgctaaccat gttcatgcct tcttcttttt    1980
cctacagctc ctgggcaacg tgctggttat tgtgctgtct catcattttg gcaaagaatt    2040
cctcgaagat ctagggaatt cgatatcaag cttgggatt ttcaggcacc accactgacc    2100
tgggacagtg ttaacgacac gatccaatgg cgacgaaggc cgtgtgcgtg ctgaagggcg    2160
acggcccagt gcagggcatc atcaatttcg agcagaagga aagtaatgga ccagtgaagg    2220
tgtggggaag cattaaagga ctgactgaag gcctgcacgg ctttcacgtc cacgagtttg    2280
gagataatac agcaggctgt accagtgcag gtcctcactt taatcctcta tccagaaaac    2340
acggtgggcc aaaggatgaa gagaggcatg ttggagactt gggcaatgtg actgctgaca    2400
aagatggtgt ggccgatgtg tctattgaag attctgtgat ctcactctca ggagaccatt    2460
gcatcattgg ccgcacactg gtggtccatg aaaaagcaga tgacttgggc aaaggtggaa    2520
atgaagaaag tacaaagaca ggaaacgctg gaagtcgttt ggcttgtggt gtaattggga    2580
tcgcccaata acattccct tggatgtagt ctgaggcccc ttaactcatc tgttatcctg    2640
ctagctgtag aaatgtatcc tgataaacat taaacactgt aatcttaaaa gtgtaattgt    2700 gtgactttt cagagttgct ttaaagtacc tgtagtgaga aactgattta tgatcacttg    2760
gaagatttgt atagttttat aaaactcagt taaaatgtct gtttcaaggc cgcttcgagc    2820
agacatgata agatacattg atgagtttgg acaaaccaca actagaatgc agtgaaaaaa    2880
atgctttatt tgtgaaattt gtgatgctat tgctttattt gtaaccatta taagctgcaa    2940
taaacaagtt aacaacaaca attgcattca ttttatgttt caggttcagg gggagatgtg    3000
ggaggttttt taaagcaagt aaaacctcta caaatgtggt aaaatcga                3048
```

<210> SEQ ID NO 10
<211> LENGTH: 1956
<212> TYPE: DNA
<213> ORGANISM: Artificial Sequence
<220> FEATURE:
<223> OTHER INFORMATION: Synthetic Polynucleotide

<400> SEQUENCE: 10

```
aattctaaat tcatatttgc atgtcgctat gtgttctggg aaatcaccat aaacgtgaaa      60
tgtctttgga tttgggaatc ttataagttc tgtatgagac cactcgcctg gaggcttgct     120
```

```
gaaggctgta tgctgatgaa catggaatcc atgcaggttt tggccactga ctgacctgca    180
tggtccatgt tcatcaggac acaaggcctg ttactagcac tcacatggaa caaatggccc    240 tttttctag tggtacgtcg ttacataact tacggtaaat ggcccgcctg gctgaccgcc    300
caacgacccc cgcccattga cgtcaataat gacgtatgtt cccatagtaa cgccaatagg    360
gactttccat tgacgtcaat gggtggagta tttacggtaa actgcccact tggcagtaca    420
tcaagtgtat catatgccaa gtacgccccc tattgacgtc aatgacggta aatggcccgc    480
ctggcattat gcccagtaca tgaccttatg gactttcct acttggcagt acatctactc    540
gaggccacgt tctgcttcac tctccccatc tccccccct cccacccc aattttgtat    600 ttatttattt tttaattatt ttgtgcagcg atggggcgg ggggggggg gggcgcgcg    660 ccaggcgggg cggggcgggg cgaggggcgg ggcgggcga ggcggagagg tgcgcggca    720 gccaatcaga gcggcgcgct ccgaaagttt cctttatgg cgaggcggcg gcggcggcgg    780
ccctataaaa agcgaagcgc gcggcgggcg ggagcgggat cagccaccgc ggtggcggcc    840
tagagtcgac gaggaactga aaaccagaa agttaactgg taagtttagt ctttttgtct    900
tttatttcag gtcccggatc cggtggtggt gcaaatcaaa gaactgctcc tcagtggatg    960
ttgcctttac ttctaggcct gtacggaagt gttacttctg ctctaaaagc tgcggaattg   1020
tacccgcggc cgatccaatg gcgacgaagg ccgtgtgcgt gctgaagggc gacggcccag   1080
tgcagggcat catcaatttc gagcagaagg aaagtaatgg accagtgaag gtgtggggaa   1140
gcattaaagg actgactgaa ggcctgcacg gctttcacgt ccacgagttt ggagataata   1200
cagcaggctg taccagtgca ggtcctcact ttaatcctct atccagaaaa cacggtgggc   1260
caaaggatga agagaggcat gttggagact tgggcaatgt gactgctgac aaagatggtg   1320
tggccgatgt gtctattgaa gattctgtga tctcactctc aggagaccat tgcatcattg   1380
gccgcacact ggtggtccat gaaaaagcag atgacttggg caaaggtgga atgaagaaa   1440 gtacaaagac aggaaacgct ggaagtcgtt tggcttgtgg tgtaattggg atcgcccaat   1500
aaacattccc ttggatgtag tctgaggccc cttaactcat ctgttatcct gctagctgta   1560
gaaatgtatc ctgataaaca ttaaacactg taatcttaaa agtgtaattg tgtgactttt   1620
tcagagttgc tttaaagtac ctgtagtgag aaactgattt atgatcactt ggaagatttg   1680
tatagtttta taaactcag ttaaaatgtc tgtttcaaca gacatgataa gatacattga   1740
tgagtttgga caaaccacaa ctagaatgca gtgaaaaaaa tgctttattt gtgaaatttg   1800
tgatgctatt gctttatttg taaccattat aagctgcaat aaacaagtta acaacaacaa   1860
ttgcattcat tttatgtttc aggttcaggg ggagatgtgg gaggttttt aaagcaagta   1920 aaacctctac aaatgtggta aaatcgataa ggatct                            1956
```

<210> SEQ ID NO 11
<211> LENGTH: 3048
<212> TYPE: DNA
<213> ORGANISM: Artificial Sequence
<220> FEATURE:
<223> OTHER INFORMATION: Synthetic Polynucleotide

<400> SEQUENCE: 11

```
tcaatattgg ccattagcca tattattcat tggttatata gcataaatca atattggcta     60
ttggccattg catacgttgt atctatatca taatatgtac atttatattg gctcatgtcc    120
aatatgaccg ccatgttggc attgattatt gactagttat taatagtaat caattacggg    180
gtcattagtt catagcccat atatggagtt ccgcgttaca taacttacgg taaatggccc    240
```

```
gcctggctga ccgcccaacg acccccgccc attgacgtca ataatgacgt atgttcccat    300
agtaacgcca atagggactt tccattgacg tcaatgggtg gagtatttac ggtaaactgc    360
ccacttggca gtacatcaag tgtatcatat gccaagtccg cccccctattg acgtcaatga   420 cggtaaatgg cccgcctggc attatgccca gtacatgacc ttacgggact ttcctacttg    480
gcagtacatc tacgtattag tcatcgctat taccatggtc gaggtgagcc ccacgttctg    540
cttcactctc cccatctccc cccctcccc acccccaatt ttgtatttat ttattttta    600 attattttgt gcagcgatgg gggcggggg gggggggggg cgcgcgccag gcgggcggg    660 gcggggcgag gggcggggcg gggcgaggcg gagaggtgcg gcggcagcca atcagagcgg    720
cgcgctccga aagtttcctt ttatggcgag gcggcggcgg cggcggccct ataaaaagcg    780
aagcgcgcgg cgggcgggag tcgctgcgac gctgccttcg ccccgtgccc cgctccgccg    840
ccgcctcgcg ccgcccgccc cggctctgac tgaccgcgtt actcccacag gtgagcgggc    900
gggacggccc ttctcctccg ggctgtaatt agcgcttggt ttaatgacgg cttgtttctt    960
ttctgtggct gcgtgaaagc cttgagggggc tccgggaggg ccctttgtgc gggggggagc   1020
ggctcggggg gtgcgtgcgt gtgtgtgtgc gtggggagcg ccgcgtgcgg cccgcgctgc   1080
ccggcggctg tgagcgctgc gggcgcggcg cggggctttg tgcgctccgc agtgtgcgcg   1140
aggggagcgc ggccggggggc ggtgcccccgc ggtgcggggg gggctgcgag gggaacaaag  1200
gctgcgtgcg gggtgtgtgc gtggggggggt gagcaggggg tgtgggcgcg gcggtcgggc  1260
tgtaaccccc ccctgcaccc ccctccccga gttgctgagc acggcccggc ttcgggtgcg   1320
gggctccgta cggggcgtgg cgcggggctc gccgtgccgg gcggggggtg gcggcaggtg   1380
ggggtgccgg gcggggcggg gccgcctcgg gccggggagg gctcggggga ggggcgcggc   1440
ggcccccgga gcgccggcgg ctgtcgaggc gcggcgagcc gcagccattg ccttttatgg   1500
taatcgtgcg agagggcgca gggacttcct ttgtcccaaa tctgtgcgga gccgaaatct   1560
gggaggcgcc gccgcacccc ctctagcggg cgcggggcga agcggtgcgg cgccggcagg   1620
aaggaaatgg gcggggaggg ccttcgtgcg tcgccgcgcc gccgtcccct tctccctctc   1680
cagcctcggg gctgtccgcg gggggacggc tgccttcggg ggggacgggg cagggcgggg   1740
ttcggcttct ggcgtgtgac cggcggctct agccggcgac cggtatgcat cctggaggct   1800
tgctgaaggc tgtatgctga tgaacatgga atccatgcag gttttggcca ctgactgacc   1860
tgcatggtcc atgttcatca ggacacaagg cctgttacta gcactcacat ggaacaaatg   1920
gcccctagct cgcgatgcat ctagagcctc tgctaaccat gttcatgcct tcttcttttt   1980
cctacagctc ctgggcaacg tgctggttat tgtgctgtct catcattttg gcaaagaatt   2040
cctcgaagat ctagggaatt cgatatcaag cttgggatt tcaggcacc accactgacc    2100 tgggacagtg ttaacgacac gatccaatgg cgacgaaggc cgtgtgcgtg ctgaagggcg    2160
acggcccagt gcaggcatc atcaatttcg agcagaagga aagtaatgga ccagtgaagg     2220
tgtggggaag cattaaagga ctgactgaag gcctgcacgg ctttcacgtc cacgagtttg    2280
gagataatac agcaggctgt accagtgcag gtcctcactt taatcctcta tccagaaaac    2340
acggtgggcc aaaggatgaa gagaggcatg ttggagactt gggcaatgtg actgctgaca    2400
aagatggtgt ggccgatgtg tctattgaag attctgtgat ctcactctca ggagaccatt    2460
gcatcattgg ccgcacactg gtggtccatg aaaaagcaga tgacttgggc aaaggtggaa    2520
atgaagaaag tacaaagaca ggaaacgctg gaagtcgttt ggcttgtggt gtaattggga    2580
```

```
tcgcccaata acattccct tggatgtagt ctgaggcccc ttaactcatc tgttatcctg    2640
ctagctgtag aaatgtatcc tgataaacat taaacactgt aatcttaaaa gtgtaattgt    2700 gtgactttt cagagttgct ttaaagtacc tgtagtgaga aactgattta tgatcacttg    2760
gaagatttgt atagttttat aaaactcagt taaaatgtct gtttcaaggc cgcttcgagc    2820
agacatgata agatacattg atgagtttgg acaaaccaca actagaatgc agtgaaaaaa    2880 atgcttatt tgtgaaattt gtgatgctat tgctttattt gtaaccatta taagctgcaa    2940
taaacaagtt aacaacaaca attgcattca ttttatgttt caggttcagg gggagatgtg    3000
ggaggttttt taaagcaagt aaaacctcta caaatgtggt aaaatcga              3048
```

<210> SEQ ID NO 12
<211> LENGTH: 2194
<212> TYPE: DNA
<213> ORGANISM: Artificial Sequence
<220> FEATURE:
<223> OTHER INFORMATION: Synthetic Polynucleotide

<400> SEQUENCE: 12

```
ccctgcgcgc tcgctcgctc actgaggccg cccgggcaaa gcccgggcgt cgggcgacct      60
ttggtcgccc ggcctcagtg agcgagcgag cgcgcagaga gggagtggaa attctaaatt     120
catatttgca tgtcgctatg tgttctggga atcaccata aacgtgaaat gtctttggat      180
ttgggaatct tataagttct gtatgagacc actcgcctgg aggcttgctg aaggctgtat     240
gctgatgaac atggaatcca tgcaggtttt ggccactgac tgacctgcat ggtccatgtt     300
catcaggaca caaggcctgt tactagcact cacatggaac aaatggccct ttttctagt      360 ggtacgtcgt tacataactt acggtaaatg gcccgcctgg ctgaccgccc aacgacccc     420 gcccattgac gtcaataatg acgtatgttc ccatagtaac gccaataggg actttccatt     480
gacgtcaatg ggtggagtat ttacggtaaa ctgcccactt ggcagtacat caagtgtatc     540
atatgccaag tacgccccct attgacgtca atgacggtaa atggcccgcc tggcattatg     600
cccagtacat gaccttatgg gactttccta cttggcagta catctactcg aggccacgtt     660
ctgcttcact ctccccatct cccccccctc cccacccca atttttgtatt tatttatttt     720 ttaattattt tgtgcagcga tggggcggg gggggggggg gggcgcgcgc caggcgggc      780 ggggcgggc gaggggcggg gcgggcgag gcggagaggt gcggcggcag ccaatcagag      840
cggcgcgctc cgaaagtttc cttttatggc gaggcggcgg cggcggcggc cctataaaa      900 gcgaagcgcg cggcgggcgg gagcgggatc agccaccgcg gtggcggcct agagtcgacg     960
aggaactgaa aaaccagaaa gttaactggt aagtttagtc ttttgtctt tattcagg     1020 tcccggatcc ggtggtggtg caaatcaaag aactgctcct cagtggatgt tgcctttact    1080
tctaggcctg tacggaagtg ttacttctgc tctaaaagct gcggaattgt acccgcggcc    1140
gatccaatgg cgacgaaggc cgtgtgcgtc tgaagggcg acggcccagt gcagggcatc    1200
atcaatttcg agcagaagga aagtaatgga ccagtgaagg tgtggggaag cattaaagga    1260
ctgactgaag gcctgcacgg ctttcacgtc cacgagtttg agataataca gcaggctgt    1320 accagtgcag gtcctcactt taatcctcta tccagaaaac acgtggggcc aaaggatgaa    1380
gagaggcatg ttggagactt gggcaatgtg actgctgaca aagatggtgt ggccgatgtg    1440
tctattgaag attctgtgat ctcactctca ggagaccatt gcatcattgg ccgcacactg    1500
gtggtccatg aaaagcaga tgacttggc aaaggtggaa atgaagaaag tacaaagaca    1560
ggaaacgctg gaagtcgttt ggcttgtggt gtaattggga tcgcccaata acattccct    1620
```

```
tggatgtagt ctgaggcccc ttaactcatc tgttatcctg ctagctgtag aaatgtatcc    1680
tgataaacat taaacactgt aatcttaaaa gtgtaattgt gtgactttttt cagagttgct    1740 ttaaagtacc tgtagtgaga aactgattta tgatcacttg gaagatttgt atagttttat    1800
aaaactcagt taaaatgtct gtttcaacag acatgataag atacattgat gagtttggac    1860
aaaccacaac tagaatgcag tgaaaaaaat gctttatttg tgaaatttgt gatgctattg    1920
ctttatttgt aaccattata agctgcaata aacaagttaa caacaacaat tgcattcatt    1980
ttatgtttca ggttcagggg gagatgtggg aggttttta aagcaagtaa aacctctaca    2040
aatgtggtaa aatcgataag aaggaacccc tagtgatgga gttggccact ccctctctgc    2100
gcgctcgctc gctcactgag gccgggcgac caaaggtcgc ccgacgcccg ggctttgccc    2160
gggcggcctc agtgagcgag cgagcgcgca gcct                                2194

<210> SEQ ID NO 13
<211> LENGTH: 1979
<212> TYPE: DNA
<213> ORGANISM: Artificial Sequence
<220> FEATURE:
<223> OTHER INFORMATION: Synthetic Polynucleotide

<400> SEQUENCE: 13
ccctgcgcgc tcgctcgctc actgaggccg cccgggcaaa gcccgggcgt cgggcgacct      60
ttggtcgccc ggcctcagtg agcgagcgag cgcgcagaga gggagtggaa attctaaatt     120
catatttgca tgtcgctatg tgttctggga aatcaccata aacgtgaaat gtctttggat     180
ttgggaatct tataagttct gtatgagacc actcgcctgg aggcttgctg aaggctgtat     240
gctgatgaac atggaatcca tgcaggtttt ggccactgac tgacctgcat ggtccatgtt     300
catcaggaca caaggcctgt tactagcact cacatggaac aaatggccct ttttctagt      360 ggtacgtcgt tacataactt acggtaaatg gcccgcctgg ctgaccgccc aacgaccccc     420
gcccattgac gtcaataatg acgtatgttc ccatagtaac gccaataggg actttccatt     480
gacgtcaatg ggtggagtat ttacggtaaa ctgcccactt ggcagtacat caagtgtatc     540
atatgccaag tacgccccct attgacgtca atgacgtaa atggcccgcc tggcattatg     600
cccagtacat gaccttatgg gactttccta cttggcagta catctactcg aggccacgtt     660
ctgcttcact ctccccatct ccccccccctc ccacccccca ttttgtatt tatttatttt      720 ttaattattt tgtgcagcga tggggggcggg gggggggggg gggcgcgcgc caggcggggc     780
ggggcggggc gaggggcggg gcggggcgag gcggagaggt gcggcggcag ccaatcagag     840
cggcgcgctc cgaaagtttc cttttatggc gaggcggcgg cggcggcggc cctataaaaa     900
gcgaagcgcg cggcgggcgg gagcgggatc agccaccgcg gtggcggcct agagtcgacg     960
aggaactgaa aaaccagaaa gttaactggt aagtttagtc ttttttgtctt ttatttcagg    1020 tcccggatcc ggtggtggtg caaatcaaag aactgctcct cagtggatgt tgcctttact    1080
tctaggcctg tacggaagtg ttacttctgc tctaaaagct gcggaattgt acccgcggcc    1140
gatccaatgg cgacgaaggc cgtgtgcgtg ctgaagggcg acggcccagt gcagggcatc    1200
atcaatttcg agcagaagga agtaatggac cagtgaaggt gtggggaag cattaaagga    1260 ctgactgaag gcctgcacgg ctttcacgtc cacgagtttg agataatac agcaggctgt    1320 accagtgcag gtcctcactt taatcctcta tccagaaaac acggtgggcc aaaggatgaa    1380
gagaggcatg ttggagactt gggcaatgtg actgctgaca aagatggtgt ggccgatgtg    1440
```

```
tctattgaag attctgtgat ctcactctca ggagaccatt gcatcattgg ccgcacactg   1500
gtggtccatg aaaaagcaga tgacttgggc aaaggtggaa atgaagaaag tacaaagaca   1560
ggaaacgctg gaagtcgttt ggcttgtggt gtaattggga tcgcccaata acagacatg    1620 ataagataca ttgatgagtt tggacaaacc acaactagaa tgcagtgaaa aaatgctttt   1680
atttgtgaaa tttgtgatgc tattgcttta tttgtaacca ttataagctg caataaacaa   1740
gttaacaaca acaattgcat tcattttatg tttcaggttc aggggagat gtgggaggtt    1800 ttttaaagca agtaaaacct ctacaaatgt ggtaaaatcg ataagaagga acccctagtg   1860
atggagttgg ccactccctc tctgcgcgct cgctcgctca ctgaggccgg gcgaccaaag   1920
gtcgcccgac gcccgggctt tgcccgggcg gcctcagtga gcgagcgagc gcgcagcct    1979
```

<210> SEQ ID NO 14
<211> LENGTH: 3372
<212> TYPE: DNA
<213> ORGANISM: Artificial Sequence
<220> FEATURE:
<223> OTHER INFORMATION: Synthetic Polynucleotide

<400> SEQUENCE: 14

```
gggggggggg ggggggggttg gccactccct ctctgcgcgc tcgctcgctc actgaggccg     60
ggcgaccaaa ggtcgcccga cgcccgggct ttgcccgggc ggcctcagtg agcgagcgag    120
cgcgcagaga gggagtggcc aactccatca ctaggggttc ctagatctca atattggcca    180
ttagccatat tattcattgg ttatatagca taaatcaata ttggctattg ccattgcat     240 acgttgtatc tatatcataa tatgtacatt tatattggct catgtccaat atgaccgcca    300
tgttggcatt gattattgac tagttattaa tagtaatcaa ttacggggtc attagttcat    360
agcccatata tggagttccg cgttacataa cttacggtaa atggcccgcc tggctgaccg    420
cccaacgacc cccgcccatt gacgtcaata atgacgtatg ttcccatagt aacgccaata    480
gggactttcc attgacgtca atgggtggag tatttacggt aaactgccca cttggcagta    540
catcaagtgt atcatatgcc aagtccgccc cctattgacg tcaatgacgg taaatggccc    600
gcctggcatt atgcccagta catgacctta cgggactttc ctacttggca gtacatctac    660
gtattagtca tcgctattac catggtcgag gtgagcccca cgttctgctt cactctcccc    720 atctccccc cctccccacc cccaattttg tatttattta ttttttaatt attttgtgca     780
gcgatggggg cggggggggg gggggggcgc gcgccaggcg gggcggggcg gggcgagggg    840
cggggcgggg cgaggcggag aggtgcggcg gcagccaatc agagcggcgc gctccgaaag    900 tttccttta tggcgaggcg gcggcggcgg cggccctata aaaagcgaag cgcgcggcgg    960
gcgggagtcg ctgcgacgct gccttcgccc cgtgccccgc tccgccgccg cctcgcgccg   1020
cccgccccgg ctctgactga ccgcgttact cccacaggtg agcgggcggg acggcccttc   1080
tcctccgggc tgtaattagc gcttggttta atgacggctt gtttcttttc tgtggctgcg   1140
tgaaagcctt gaggggctcc gggagggccc tttgtgcggg gggagcggc tcggggggtg    1200 cgtgcgtgtg tgtgtgcgtg gggagcgccg cgtgcggccc gcgctgcccg gcggctgtga   1260
gcgctgcggg cgcggcgcgg ggctttgtgc gctccgcagt gtgcgcgagg ggagcgcggc    1320 cggggcggt gcccgcggt gcggggggg ctgcgagggg aacaaaggct gcgtgcgggg     1380
tgtgtgcgtg gggggtgag caggggtgt gggcgcggcg gtcgggctgt aacccccccc     1440
tgcacccccc tccccgagtt gctgagcacg gcccggcttc gggtgcgggg ctccgtacgg    1500
ggcgtggcgc ggggctcgcc gtgccgggcg gggggtggcc gcaggtgggg gtgccgggcg    1560
```

```
gggcggggcc gcctcgggcc ggggagggct cggggagggg gcgcggcggc ccccggagcg    1620
ccggcggctg tcgaggcgcg gcgagccgca gccattgcct tttatggtaa tcgtgcgaga    1680
gggcgcaggg acttcctttg tcccaaatct gtgcggagcc gaaatctggg aggcgccgcc    1740
gcaccccctc tagcgggcgc ggggcgaagc ggtgcggcgc cggcaggaag gaaatgggcg    1800
gggagggcct tcgtgcgtcg ccgcgccgcc gtccccttct ccctctccag cctcggggct    1860
gtccgcgggg gacggctgc cttcgggggg gacggggcag ggcggggttc ggcttctggc     1920
gtgtgaccgg cggctctagc cggcgaccgg tatgcatcct ggaggcttgc tgaaggctgt    1980
atgctgatga acatggaatc catgcaggtt ttggccactg actgacctgc atggtccatg    2040
ttcatcagga cacaaggcct gttactagca ctcacatgga acaaatggcc cctagctcgc    2100
gatgcatcta gagcctctgc taaccatgtt catgccttct tcttttttcct acagctcctg   2160 ggcaacgtgc tggttattgt gctgtctcat cattttggca agaattcct cgaagatcta     2220 gggaattcga tatcaagctt ggggattttc aggcaccacc actgacctgg gacagtgtta    2280
acgacacgat ccaatggcga cgaaggccgt gtgcgtgctg aagggcgacg gcccagtgca    2340
gggcatcatc aatttcgagc agaaggaaag taatggacca gtgaaggtgt ggggaagcat    2400
taaaggactg actgaaggcc tgcacggctt tcacgtccac gagtttggag ataatacagc    2460
aggctgtacc agtgcaggtc ctcactttaa tcctctatcc agaaaacacg gtgggccaaa    2520
ggatgaagag aggcatgttg gagacttggg caatgtgact gctgacaaag atggtgtggc    2580
cgatgtgtct attgaagatt ctgtgatctc actctcagga gaccattgca tcattggccg    2640
cacactggtg gtccatgaaa aagcagatga cttgggcaaa ggtggaaatg aagaaagtac    2700
aaagacagga aacgctggaa gtcgtttggc ttgtggtgta attgggatcg cccaataaac    2760
attcccttgg atgtagtctg aggcccctta actcatctgt tatcctgcta gctgtagaaa    2820
tgtatcctga taaacattaa acactgtaat cttaaaagtg taattgtgtg acttttttcag  2880 agttgcttta aagtacctgt agtgagaaac tgatttatga tcacttggaa gatttgtata    2940
gttttataaa actcagttaa aatgtctgtt tcaaggccgc ttcgagcaga catgataaga    3000
tacattgatg agtttggaca aaccacaact agaatgcagt gaaaaaaatg ctttatttgt    3060
gaaatttgtg atgctattgc tttatttgta accattataa gctgcaataa acaagttaac    3120
aacaacaatt gcattcattt tatgtttcag gttcagggggg agatgtggga ggttttttaa   3180
agcaagtaaa acctctacaa atgtggtaaa atcgacgata aggatctagg aacccctagt    3240
gatggagttg gccactccct ctctgcgcgc tcgctcgctc actgaggccg cccgggcaaa    3300
gcccgggcgt cgggcgacct ttggtcgccc ggcctcagtg agcgagcgag cgcgcagaga    3360
gggagtggcc aa                                                         3372
```

<210> SEQ ID NO 15
<211> LENGTH: 3148
<212> TYPE: DNA
<213> ORGANISM: Artificial Sequence
<220> FEATURE:
<223> OTHER INFORMATION: Synthetic Polynucleotide

<400> SEQUENCE: 15

```
gggggggggg gggggggttg gccactccct ctctgcgcgc tcgctcgctc actgaggccg      60
ggcgaccaaa ggtcgcccga cgcccgggct tgcccgggc ggcctcagtg agcgagcgag     120
cgcgcagaga gggagtggcc aactccatca ctaggggttc ctagatctca atattggcca    180
```

```
ttagccatat tattcattgg ttatatagca taaatcaata ttggctattg gccattgcat    240
acgttgtatc tatatcataa tatgtacatt tatattggct catgtccaat atgaccgcca    300
tgttggcatt gattattgac tagttattaa tagtaatcaa ttacggggtc attagttcat    360
agcccatata tggagttccg cgttacataa cttacggtaa atggcccgcc tggctgaccg    420
cccaacgacc cccgcccatt gacgtcaata atgacgtatg ttcccatagt aacgccaata    480
gggactttcc attgacgtca atgggtggag tatttacggt aaactgccca cttggcagta    540
catcaagtgt atcatatgcc aagtccgccc cctattgacg tcaatgacgg taaatggccc    600
gcctggcatt atgcccagta catgacctta cgggactttc ctacttggca gtacatctac    660
gtattagtca tcgctattac catggtcgag gtgagcccca cgttctgctt cactctcccc    720 atctccccc  cctccccacc cccaattttg tatttattta tttttttaatt attttgtgca    780 gcgatggggg cggggggggg ggggggcgc  gcgccaggcg gggcggggcg gggcgagggg    840
cggggcgggg cgaggcggag aggtgcggcg gcagccaatc agagcggcgc gctccgaaag    900
tttcctttta tggcgaggcg gcggcggcgg cggccctata aaaagcgaag cgcgcggcgg    960
gcgggagtcg ctgcgacgct gccttcgccc cgtgccccgc tccgccgccg cctcgcgccg    1020
cccgccccgg ctctgactga ccgcgttact cccacaggtg agcgggcggg acggcccttc    1080
tcctccgggc tgtaattagc gcttggttta atgacggctt gtttcttttc tgtggctgcg    1140
tgaaagcctt gaggggctcc ggagggccc  tttgtgcggg gggagcggc  tcggggggtg    1200 cgtgcgtgtg tgtgtgcgtg gggagcgccg cgtgcggccc gcgctgcccg gcggctgtga    1260
gcgctgcggg cgcggcgcgg ggctttgtgc gctccgcagt gtgcgcgagg ggagcgcggc    1320
cgggggcggt gccccgcggt gcgggggggg ctgcgagggg aacaaaggct gcgtgcgggg    1380
tgtgtgcgtg gggggtgag  cagggggtgt gggcgcggcg gtcgggctgt aaccccccc     1440 tgcaccccc  tccccgagtt gctgagcacg gcccggcttc gggtgcgggg ctccgtacgg    1500
ggcgtggcgc ggggctcgcc gtgccggcg  ggggtgcg   gcaggtgggg gtgccgggcg    1560
gggcggggcc gcctcgggcc ggggagggct cggggga gg gcgcggcggc cccggagcg     1620 ccggcggctg tcgaggcgcg gcgagccgca gccattgcct tttatggtaa tcgtgcgaga    1680
gggcgcaggg acttcctttg tcccaaatct gtgcggagcc gaaatctggg aggcgccgcc    1740
gcaccccctc tagcgggcgc ggggcgaagc ggtgcggcgc cggcaggaag gaaatgggcg    1800
gggagggcct tcgtgcgtcg ccgcgccgcc gtcccttct  ccctctccag cctcggggct    1860
gtccgcgggg gacggctgc  cttcgggggg gacggggcag ggcggggttc ggcttctggc    1920
gtgtgaccgg cggctctagc cggcgaccgg tatgcatcct ggaggcttgc tgaaggctgt    1980
atgctgatga acatggaatc catgcaggtt ttggccactg actgacctgc atggtccatg    2040
ttcatcagga cacaaggcct gttactagca ctcacatgga acaaatggcc cctagctcgc    2100
gatgcatcta gagcctctgc taaccatgtt catgccttct tctttttcct acagctcctg    2160
ggcaacgtgc tggttattgt gctgtctcat cattttggca aagaattcct cgaagatcta    2220
gggaattcga tatcaagctt ggggattttc aggcaccacc actgacctgg acagtgtta    2280 acgacacgat ccaatggcga cgaaggccgt gtgcgtgctg aagggcgacg gcccagtgca    2340
gggcatcatc aatttcgagc agaaggaaag taatggacca gtgaaggtgt ggggaagcat    2400
taaaggactg actgaaggcc tgcacggctt tcacgtccac gagtttggag ataatacagc    2460
aggctgtacc agtgcaggtc ctcactttaa tcctctatcc agaaaacacg gtgggccaaa    2520
ggatgaagag aggcatgttg gagacttggg caatgtgact gctgacaaag atggtgtggc    2580
```

| | |
|---|---|
| cgatgtgtct attgaagatt ctgtgatctc actctcagga gaccattgca tcattggccg | 2640 |
| cacactggtg gtccatgaaa aagcagatga cttgggcaag ggtggaaatg aagaaagtac | 2700 |
| aaagacagga aacgctggaa gtcgtttggc ttgtggtgta attgggatcg cccaataaag | 2760 |
| agcagacatg ataagataca ttgatgagtt tggacaaacc acaactagaa tgcagtgaaa | 2820 |
| aaaatgcttt atttgtgaaa tttgtgatgc tattgctta tttgtaacca ttataagctg | 2880 |
| caataaacaa gttaacaaca acaattgcat tcattttatg tttcaggttc aggggagat | 2940 |
| gtgggaggtt ttttaaagca agtaaaacct ctacaaatgt ggtaaaatcg acgataagga | 3000 |
| tctaggaacc cctagtgatg gagttggcca ctccctctct gcgcgctcgc tcgctcactg | 3060 |
| aggccgcccg ggcaaagccc gggcgtcggg cgacctttgg tcgcccggcc tcagtgagcg | 3120 |
| agcgagcgcg cagagaggga gtggccaa | 3148 |

<210> SEQ ID NO 16
<211> LENGTH: 2173
<212> TYPE: DNA
<213> ORGANISM: Homo sapiens

<400> SEQUENCE: 16

| | |
|---|---|
| gtgagctgag attgcaccac tgcactccag cctggtgaca gagtgagact ccatatcaaa | 60 |
| ataaatacat aaataaataa aaacagtgat tcttaactgg gagtgatttg gcaacgtctg | 120 |
| gaattatttt tggttatccc agcctggcag ggagggacag ggtattactg gcatctagtg | 180 |
| agtaggggct agggattcta ctgaacatcc tacagtgtac aggacagcct ccacagcaaa | 240 |
| gaactgtctg gcccaaaatg tccatagtgc ccacattcga tgccctgcat taggaagata | 300 |
| taaatactct aaatatcac agagttaaat tccttacccc tgttctagca gagatgatat | 360 |
| tcttgcgggg ggagcatctt cttggcttca acacattctt ttctccatgg gagatgatgc | 420 |
| cagaagaggg acagaacagg gcccagtaaa gcatggggcc tggggccagg gaccccctg | 480 |
| ttcaggtgtg acgaccatcc tacgaaggca ccacccaggc atcattagac cgtctcaaaa | 540 |
| gaagagtaat tcactgtccc aaagcagctc tctcgtgtct gtgggcggat cccttggcaa | 600 |
| gtttacaatg aactgaaatc tgccgaactt cctggaaccc aaagaaactt tagccttggg | 660 |
| caaaggccct ttggccagca tttgcactgt ttatgcaacc gtttagaata tacgaattat | 720 |
| ctggagacta ctaccaaata caacaggcaa aactgcaaat atgtatactt cctagaggat | 780 |
| gataaaaaaa tgtgaattgt atttctctga taggaggatgc attagagtct gagggtctaa | 840 |
| atagcgtaaa taataaataa gtaaataaat cgatagtagt gtactccaaa cgaggctgga | 900 |
| atagcttcta ttgttgtttc acactggact tcaattaagt ctcagtattt tgccatactc | 960 |
| aatattaagt actaggctgg acgtggtggc tcatgtctgt aatcccagca ctttgggagg | 1020 |
| ccgaggtggg tagatggctg gcttgagctc aggagtttga accagcctg ggcaacatgg | 1080 |
| taaaacccca tctgtaccca aaatacaaaa atcagccagg tgtggtggca catgcctgtg | 1140 |
| gtcccaggta cttgggaggc tgaggcagga ggatggcttg aacccaggag gtggaggctg | 1200 |
| cagtgagcta tgatggcgcc actgcactcc agcctgggtg acagagcgag accctgtctc | 1260 |
| aaaaatcaaa caaacaaccc cctcgccccg gacaaaagta gtttgcacta ttttctcatt | 1320 |
| tcacaatatg ttttgaaat atttcccttg aaaggtaagt catatttatc attcctgttg | 1380 |
| tatggaggca tcataaatta tttcaccatt ctaccctcct tgagtgttgt ggcctttagg | 1440 |
| ccagacaaaa acgcaggtga tgcctagaag ccaactagtt gccgtttggt tatctgtagg | 1500 |

-continued

```
gttgtggcct tgccaaacag gaaaaatata aaaagaatac cgaattctgc caaccaaata   1560
agaaactcta tactaaggac taagaaaatt gcaggggaag aaaaggtaag tcccgggatt   1620
gaggtgtagc gactttctat accctcagaa aactaaaaaa caagacaaaa aaatgaaaac   1680
tacaaaagca tccatcttgg ggcgtcccaa ttgctgagta acaaatgaga cgctgtggcc   1740
aaactcagtc ataactaatg acatttctag acaaagtgac ttcagatttt caaagcgtac   1800
cctgtttaca tcattttgcc aatttcgcgt actgcaaccg gcgggccacg ccccgtgaa    1860 aagaaggttg ttttctccac atttcggggt tctggacgtt tcccggctgc ggggcggggg   1920
gagtctccgg cgcacgcggc cccttggccc cgcccccagt cattcccggc cactcgcgac   1980
ccgaggctgc cgcaggggc gggctgagcg cgtgcgaggc gattggtttg gggccagagt    2040
gggcgaggcg cggaggtctg gcctataaag tagtcgcgga gacggggtgc tggtttgcgt   2100
cgtagtctcc tgcagcgtct gggtttccg ttgcagtcct cggaaccagg acctcggcgt    2160
ggcctagcga gtt                                                     2173
```

<210> SEQ ID NO 17
<211> LENGTH: 154
<212> TYPE: PRT
<213> ORGANISM: Homo sapiens

<400> SEQUENCE: 17

```
Met Ala Thr Lys Ala Val Cys Val Leu Lys Gly Asp Gly Pro Val Gln
1               5                   10                  15

Gly Ile Ile Asn Phe Glu Gln Lys Glu Ser Asn Gly Pro Val Lys Val
            20                  25                  30

Trp Gly Ser Ile Lys Gly Leu Thr Glu Gly Leu His Gly Phe His Val
        35                  40                  45

His Glu Phe Gly Asp Asn Thr Ala Gly Cys Thr Ser Ala Gly Pro His
    50                  55                  60

Phe Asn Pro Leu Ser Arg Lys His Gly Gly Pro Lys Asp Glu Glu Arg
65                  70                  75                  80

His Val Gly Asp Leu Gly Asn Val Thr Ala Asp Lys Asp Gly Val Ala
                85                  90                  95

Asp Val Ser Ile Glu Asp Ser Val Ile Ser Leu Ser Gly Asp His Cys
            100                 105                 110

Ile Ile Gly Arg Thr Leu Val Val His Glu Lys Ala Asp Asp Leu Gly
        115                 120                 125

Lys Gly Gly Asn Glu Glu Ser Thr Lys Thr Gly Asn Ala Gly Ser Arg
    130                 135                 140

Leu Ala Cys Gly Val Ile Gly Ile Ala Gln
145                 150
```

SOD1 DUAL EXPRESSION VECTORS AND USES THEREOF

RELATED APPLICATIONS

This application is a national stage filing under 35 U.S.C. § 371 of international PCT application PCT/US2018/052173, filed Sep. 21, 2018, entitled "SOD1 DUAL EXPRESSION VECTORS AND USES THEREOF", which claims the benefit under 35 U.S.C. § 119(e) of the filing date of U.S. Provisional Application Ser. No. 62/561,932, filed on Sep. 22, 2017, the entire contents of each of which are incorporated herein by reference.

BACKGROUND

Amyotrophic lateral sclerosis (ALS) is a progressive, generally fatal motor neuron disorder that sometimes develops concurrently with frontotemporal dementia (FTD). ALS is encountered in both sporadic (SALS) and familial (FALS) forms. About 10% of cases are transmitted as autosomal dominant traits. An FDA-approved therapy for ALS is riluzole, a compound that prolongs survival by about 10%.

Generally, studies showing benefit of SOD1 silencing in ALS cells and transgenic animals have not described silencing only the mutant allele. Rather, in most studies the silencing reduces levels of both the mutant, toxic SOD1 protein and also the wildtype SOD1 protein. However, excessive silencing of SOD1 from both the mutant and the wild-type alleles might relate to undesirable biological consequences as a result of reducing activity or function of wild-type SOD1 protein.

SUMMARY

Aspects of the disclosure relate to compositions and methods for modulating cytosolic Cu/Zn superoxide dismutase (SOD1) expression in cells. Accordingly, in some embodiments, methods are provided that are useful for treating ALS. In some embodiments, the disclosure provides synthetic nucleic acids (e.g., a synthetic microRNA) engineered to inhibit expression of endogenous SOD1 in cells or a subject. In some embodiments, the disclosure provides a nucleic acid engineered to express exogenous SOD1 in cells or a subject. In some embodiments, such exogenous SOD1 is resistant to targeting by a synthetic nucleic acid (e.g., a synthetic microRNA) that targets endogenous SOD1. Accordingly, in some embodiments, the disclosure provides compositions and methods for coupling the delivery of (1) a synthetic microRNA to silence expression of endogenous cytosolic Cu/Zn superoxide dismutase (SOD1) activity, with (2) a second construct to express exogenous SOD1 resistant to the synthetic microRNA (miRNA).

The disclosure is based, in part, on compositions and methods described here that address the challenge of loss of neuroprotective activity from SOD1 dismutation by including in series with an anti-SOD1 miRNA, a cDNA for SOD1 expressed from an RNA engineered to be resistant to the anti-SOD1 miRNA. In some embodiments, constructs described by the disclosure, allow for normal levels of SOD1 dismutation activity (e.g., in a cell or subject that has been administered the construct) even with total silencing of both WT and mutant endogenous SOD1 alleles.

Accordingly, in some aspects, the disclosure provides an isolated nucleic acid comprising: a first region that encodes one or more first miRNAs comprising a nucleic acid having sufficient sequence complementary with an endogenous mRNA of a subject to hybridize with and inhibit expression of the endogenous mRNA, wherein the endogenous mRNA encodes a SOD1 protein; and a second region encoding an exogenous mRNA that encodes a wild-type SOD1 protein, wherein the one or more first miRNAs do not comprise a nucleic acid having sufficient sequence complementary to hybridize with and inhibit expression of the exogenous mRNA.

In some embodiments, an exogenous mRNA lacks a 5' untranslated region (5' UTR), lacks a 3' untranslated region (3' UTR), or lacks both a 5' UTR and a 3'UTR.

In some embodiments, an exogenous mRNA encoding the SOD1 protein has one or more silent base pair mutations relative to the endogenous mRNA. In some embodiments, an exogenous mRNA comprises a nucleic acid sequence that is at least 95% identical to the endogenous mRNA.

In some embodiments, the wild-type SOD1 is encoded by a nucleic acid sequence set forth in SEQ ID NO: 7 (Hardened SOD1 sequence).

In some embodiments, one or more first miRNAs targets an untranslated region (e.g. 5' UTR or 3'UTR) of a nucleic acid encoding an endogenous mRNA. In some embodiments, one or more first miRNAs targets a coding sequence of a nucleic acid encoding an endogenous mRNA.

In some embodiments, one or more first miRNAs hybridizes to a nucleic acid comprising 5, 6, 7, 8, 9, 10, 11, 12, 13, 14, 15, 16, 17, 18, 19, 20 or 21 consecutive nucleotides of a RNA encoded by the sequence as set forth in SEQ ID NO: 3. In some embodiments, one or more first miRNAs hybridizes to a nucleic acid comprising 5, 6, 7, 8, 9, 10, 11, 12, 13, 14, 15, 16, 17, 18, 19, 20 or 21 consecutive nucleotides of a RNA encoded by the sequence as set forth in SEQ ID NO: 2.

In some embodiments, one or more first miRNAs comprises or is encoded by 5, 6, 7, 8, 9, 10, 11, 12, 13, 14, 15, 16, 17, 18, 19, 20 or 21 consecutive nucleotides of a sequence as set forth in SEQ ID NO: 4. In some embodiments, one or more first miRNAs comprises or is encoded by 5, 6, 7, 8, 9, 10, 11, 12, 13, 14, 15, 16, 17, 18, 19, 20 or 21 consecutive nucleotides of a sequence as set forth in SEQ ID NO: 3. In some embodiments, an miRNA further comprises flanking regions of miR-155 or flanking regions of miR-30.

In some embodiments, an isolated nucleic acid further comprises a first promoter. In some embodiments, a first promoter is operably linked to a first region of an isolated nucleic acid as described by the disclosure.

In some embodiments, a first promoter is a RNA polymerase III (pol III) promoter, such as an H1 promoter or a U6 promoter.

In some embodiments, a first promoter is a RNA polymerase II (pol II) promoter, such as a chicken beta actin (CBA) promoter, or an endogenous SOD1 promoter (e.g., SEQ ID NO: 16).

In some embodiments, an isolated nucleic acid further comprises a second promoter. In some embodiments, a second promoter is operably linked to a second region of an isolated nucleic acid as described by the disclosure.

In some embodiments, a second promoter is a pol II promoter, such as a chicken beta actin (CBA) promoter, or an endogenous SOD1 promoter.

In some embodiments, an isolated nucleic acid further comprises an enhancer sequence, such as a cytomegalovirus (CMV) enhancer.

In some embodiments, a first region is positioned within an untranslated region (e.g., UTR) of a second region. In some embodiments, a first region is positioned within an intron of an isolated nucleic acid. In some embodiments, a first region is positioned 5' with respect to a second region.

In some embodiments, an isolated nucleic acid further comprises at least one adeno-associated virus (AAV) inverted terminal repeat (ITR). In some embodiments, an isolated nucleic acid comprises a full-length ITR and a mutant ITR. In some embodiments, ITRs flank the first and second regions of an isolated nucleic acid as described by the disclosure.

In some embodiments, the disclosure provides a recombinant adeno-associated virus (rAAV) comprising an isolated nucleic acid as described by the disclosure and an AAV capsid protein.

In some embodiments, a rAAV targets CNS tissue. In some embodiments, a rAAV targets neurons.

In some embodiments, a capsid protein is AAV9 capsid protein or AAVrh.10 capsid protein.

In some aspects, the disclosure provides a composition comprising an isolated nucleic as described by the disclosure, or an rAAV as described by the disclosure, and a pharmaceutically acceptable excipient.

In some aspects, the disclosure provides a method for inhibiting SOD1 expression in a cell, the method comprising delivering to a cell an isolated nucleic acid as described by the disclosure, or an rAAV as described by the disclosure.

In some embodiments, a cell comprises a nucleic acid sequence encoding a mutant SOD1 protein.

In some aspects, the disclosure provides a method for treating a subject having or suspected of having ALS, the method comprising administering to the subject an effective amount of an isolated nucleic acid as described by the disclosure, or an effective amount of an rAAV as described by the disclosure.

In some embodiments, a subject comprises a nucleic acid sequence encoding a mutant SOD1 protein. In some embodiments, a subject is a mammalian subject, such as a human subject.

BRIEF DESCRIPTION OF DRAWINGS

FIG. 9 shows a nucleic acid sequence alignment of wild-type SOD1 coding sequence (SEQ ID NO: 1) with an example of a "hardened" SOD1 coding sequence (SEQ ID NO: 7).

DETAILED DESCRIPTION

Figure 4:
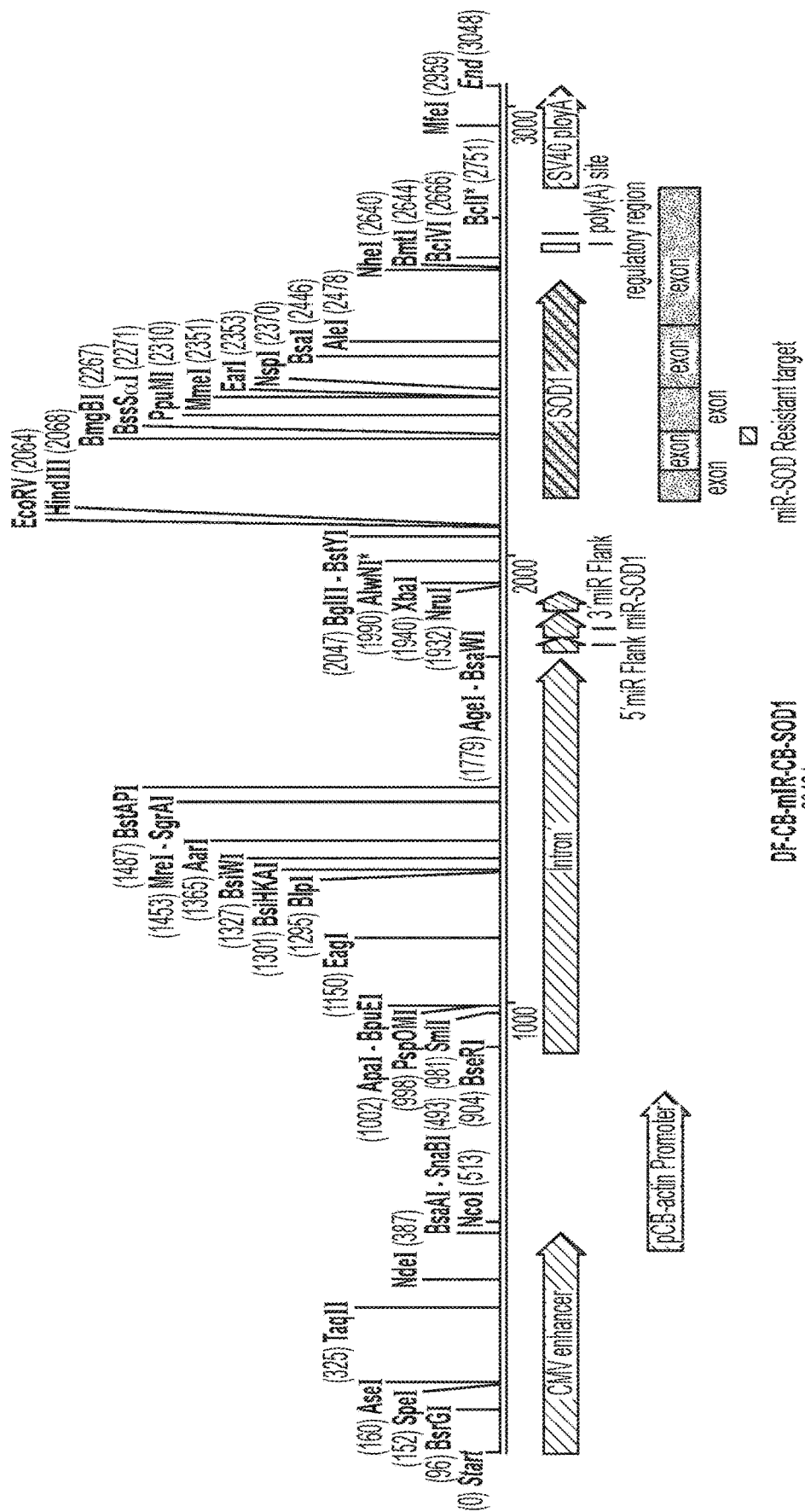
FIG. 4 shows a schematic overview of construct design for a single promoter dual function vector. The anti-Sod1 miRNA and miRNA-resistant SOD1 cDNA are both expressed by a chicken beta actin promoter and CMV enhancer (e.g., CAG promoter). The locus of the SOD1 cDNA containing a silent mutation relative to wild-type SOD1 is shown ("miR-SOD Resistant Target"). The anti-Sod1 miR is located in an intron.

In some aspects, the disclosure relates to compositions and methods for modulating expression and/or activity of genes associated with amyotrophic lateral sclerosis (ALS) in cells (e.g., cells of a subject). For example, in some aspects, the disclosure provides compositions (e.g., dual function vectors) that simultaneously express in cells or a subject (i) one or more synthetic nucleic acids (e.g., inhibitory RNAs, such as miRNAs, siRNAs, shRNAs, etc.) that inhibits a gene associated with ALS and (ii) an exogenous gene associated with ALS that encodes a protein that is resistant to the synthetic nucleic acid. Examples of genes associated with ALS include but are not limited to C9Orf72, SOD1, FUS, TARDBP, SQSTM1, VCP, OPTN, PFN1, UBQLN2, DCTN1, ALS2, CHMP2B, FIG4, HNRNAP1, ATXN2, ANG, SPG11, VAPB, NEFH, CHCHD10, ERBB4, PRPH, MATR3, SETX, SIGMAR1, TBK1, TRPM7, TUBA4A, ANXA11, NEK1, SARM1, UN13A, MOBP, SCFD1, C21Orf2, and others described, for example by Renton et al. (2014) *Nature Neuroscience* 17(1):17-23. In some embodiments, the gene associated with ALS is a dominant negative gene associated with ALS (e.g., a gene encoding a dominant negative gene product, such as a protein, that is associated with ALS).

Aspects of the disclosure relate to compositions and methods for modulating cytosolic Cu/Zn superoxide dismutase (SOD1) expression in cells. Accordingly, in some embodiments, methods are provided that are useful for treating ALS. In some embodiments, the disclosure provides synthetic nucleic acids (e.g., a synthetic microRNA) engineered to inhibit expression of endogenous SOD1 in cells or a subject. In some embodiments, the disclosure provides a nucleic acid engineered to express exogenous SOD1 in cells or a subject. In some embodiments, such exogenous SOD1 is resistant to targeting by a synthetic nucleic acid (e.g., a synthetic microRNA) that targets endogenous SOD1.

Aspects of the disclosure relate to improved gene therapy compositions and related methods for treating ALS using the recombinant adeno-associated viral (rAAV) vectors. In particular, rAAVs are provided that harbor nucleic acids engineered to express inhibitory nucleic acids that silence genes, such as SOD1, which are associated with ALS. In some embodiments, the disclosure utilizes a recombinant AAV (e.g., rAAV9, rAAV.Rh10, etc.) to deliver a microRNA to the CNS and thereby silence an ALS gene, such as SOD1. In some aspects, the disclosure relates to the discovery of dual function vectors that are capable of knocking-down endogenous SOD1 expression (e.g., wild-type SOD1 and mutant SOD1 expression) in a subject while expressing wild-type SOD1. Accordingly, constructs described by the disclosure, in some embodiments, allow for normal levels of SOD1 dismutation activity (e.g., in a cell or subject that has been administered the construct) even with total silencing of both WT and mutant endogenous SOD1 alleles.

In some aspects, the disclosure provides an isolated nucleic acid comprising: a first region that encodes one or more first miRNAs comprising a nucleic acid having sufficient sequence complementary with an endogenous mRNA of a subject to hybridize with and inhibit expression of the endogenous mRNA, wherein the endogenous mRNA encodes a SOD1 protein; and a second region encoding an exogenous mRNA that encodes a wild-type SOD1 protein, wherein the one or more first miRNAs do not comprise a nucleic acid having sufficient sequence complementary to hybridize with and inhibit expression of the exogenous mRNA.

SOD1

As used herein, "SOD1" refers to Superoxide dismutase (SOD1), which is an enzyme encoded in humans by the SOD1 gene. Typically, SOD1 functions to catalyze disproportionation of superoxide to hydrogen peroxide and dioxygen, and remove free radicals in the body. "Wild-type SOD1" refers to a gene product (e.g., protein) encoded by a SOD1 gene that does not cause gain of function toxicity in a cell or subject (e.g., that does not or will not result in the development of ALS). In some embodiments, a wild-type SOD1 gene encodes an mRNA transcript (e.g., a mature mRNA transcript) having a sequence set forth in NCBI Accession No. NM_000454.4.

"Mutant SOD1" refers to a gene product (e.g., protein) comprising one or more mutations (e.g., missense mutations, nonsense mutations, frameshift mutations, insertions, deletions, etc.) that result in the gene product (e.g., protein) having an altered function, such as a toxic gain of function. Generally, a nucleic acid encoding a mutant SOD1 gene product does not comprise any silent mutations relative to a nucleic acid encoding a wild-type SOD1 gene product.

Mutations in the gene encoding Superoxide dismutase (SOD1), located on chromosome 21, have been linked to familial amyotrophic lateral sclerosis. Superoxide dismutase (SOD1) is an enzyme encoded by the SOD1 gene. SOD1 binds copper and zinc ions and is one of three superoxide dismutases responsible for destroying free superoxide radicals in the body. The encoded isozyme is a soluble cytoplasmic and mitochondrial intermembrane space protein, acting as a homodimer to convert naturally occurring, but harmful, superoxide radicals to molecular oxygen and hydrogen peroxide. Frequent SOD1 mutations that occur and cause ALS include A4V, H46R and G93A. Additional SOD1 mutations are described, for example by Banci et al. (2008) *PLoS ONE* 3(2): e1677.

The disclosure is based, in part, on the discovery that nucleic acid constructs that simultaneously inhibit endogenous SOD1 expression in a non-allele-specific manner (e.g. silence endogenous wild-type and endogenous mutant SOD1) and express an exogenous SOD1 protein (e.g., express an exogenous wild-type SOD1 or an exogenous hardened SOD1 protein) allow for normal levels of SOD1 dismutation activity even with total silencing of both WT and mutant endogenous SOD1 alleles. As used herein, "endogenous" refers to a gene (e.g., a SOD1 gene) or a gene product (e.g., a SOD1 protein) that is encoded by the native DNA of a cell. "Exogenous" refers to a gene (e.g., a nucleic acid encoding a SOD1 protein, such as SOD1 cDNA) or a gene product (e.g. a SOD1 protein, such as a hardened SOD1 protein) that originates from a source other than the native DNA of a cell (e.g., has been introduced to a cell non-naturally).

In some embodiments, an exogenous SOD1 nucleic acid sequence encodes a hardened SOD1 protein. As used herein, "hardened SOD1" refers to a nucleic acid sequence encoding a SOD1 protein that comprises one or more silent mutations such that it encodes the same protein as an endogenous wild-type SOD1 protein but has a different primary nucleic acid (e.g., DNA) sequence. Without wishing to be bound by any particular theory, a "hardened SOD1" mRNA transcript is not inhibited by certain inhibitory RNAs (e.g., miRNAs) that target endogenous SOD1 RNA transcripts (e.g., wild-type SOD1 and mutant SOD1 transcripts).

The number of silent mutations in a hardened SOD1 nucleic acid sequence can vary. In some embodiments, a nucleic acid sequence encoding a hardened SOD1 comprises between about 1 and about 50 (e.g., any integer between 1 and 50, inclusive) silent mutations relative to a wild-type SOD1 nucleic acid sequence (e.g., SEQ ID NO: 1; SOD1 coding sequence). In some embodiments, a nucleic acid sequence encoding a hardened SOD1 comprises at least 1, at least 2, at least 3, at least 4, at least 5, at least 6, at least 7, at least 8, at least 9, at least 10, at least 11, at least 12, at least 13, at least 14, or at least 15 silent mutations relative to a wild-type SOD1 nucleic acid sequence (e.g., SEQ ID NO: 1; SOD1 coding sequence). In some embodiments, one or more silent mutations of a nucleic acid sequence encoding a hardened SOD1 are located in a seed region targeted by an inhibitory nucleic acid. In some embodiments, a seed region ranges from about 3 to about 25 continuous nucleotides in length (e.g., any integer between 3 and 25, inclusive).

The nucleic acid (e.g., DNA) sequence identity between a nucleic acid encoding an exogenous (e.g., hardened) SOD1 protein and an endogenous wild-type SOD1 protein can vary. In some embodiments, a nucleic acid sequence encoding an exogenous SOD1 protein is between about 99.9% and about 85% identical to an endogenous wild-type SOD1 nucleic acid sequence (e.g., SEQ ID NO: 1; SOD1

DNA coding sequence). In some embodiments, a nucleic acid sequence encoding an exogenous SOD1 protein is about 99.9%, about 99%, about 98%, about 97%, about 96%, about 95%, about 94%, about 93%, about 92%, about 91%, about 90%, about 89%, about 88%, about 87%, about 86%, or about 85% identical to an endogenous wild-type SOD1 nucleic acid sequence (e.g., SEQ ID NO: 1; SOD1 DNA coding sequence). In some embodiments, a nucleic acid sequence encodes an exogenous SOD1 protein having an amino acid sequence that is between about 99.9% and about 90% (e.g., about 99.9%, about 99%, about 98%, about 97%, about 96%, about 95%, about 94%, about 93%, about 92%, about 91%, or about 90%) identical to an endogenous wild-type SOD1 amino acid sequence (e.g., SEQ ID NO: 17).

Inhibitory Nucleic Acids

Aspects of the disclosure relate to inhibitory nucleic acids targeting SOD1 (e.g., endogenous SOD1). In some embodiments, the inhibitory nucleic acid is a nucleic acid that hybridizes to at least a portion of the target nucleic acid, such as an RNA, pre-mRNA, mRNA, and inhibits its function or expression. In some embodiments, the inhibitory nucleic acid is single stranded or double stranded. In some embodiments, the inhibitory nucleic acid comprises or is encoded by of a sequence as set forth as SEQ ID NO: 4: CTGCATG-GATTCCATGTTCAT (miR-SOD-127). In some embodiments, the inhibitory nucleic acid comprises or is encoded by of a sequence as set forth as SEQ ID NO: 3: CTGCATG-GATTCCATGTTCAT (miR-SOD-127). In some embodiments, the inhibitory nucleic acid is a mature miRNA that comprises SEQ ID NO: 3 and SEQ ID NO: 4. In some embodiments, SEQ ID NO: 3 is the guide strand of the mature miRNA and SEQ ID NO: 4 is the passenger strand (e.g., miRNA*) of the mature miRNA.

In some embodiments, the inhibitory nucleic acid is 5 to 30 bases in length (e.g., 10-30, 15-25, 19-22). The inhibitory nucleic acid may also be 10-50, or 5-50 bases length. For example, the inhibitory nucleic acid may be one of any of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 bases in length. In some embodiments, the inhibitory nucleic acid comprises or consists of a sequence of bases at least 80% or 90% complementary to, e.g., at least 5, 10, 15, 20, 25 or 30 bases of, or up to 30 or 40 bases of, the target nucleic acid, or comprises a sequence of bases with up to 6 mismatches over 10, 15, 20, 25 or 30 bases of the target nucleic acid.

In some embodiments, any one or more thymidine (T) nucleotides or uridine (U) nucleotides in a sequence provided herein may be replaced with any other nucleotide suitable for base pairing (e.g., via a Watson-Crick base pair) with an adenosine nucleotide. For example, T may be replaced with U, and U may be replaced with T. In some embodiments, inhibitory nucleic acids are provided that inhibit expression of genes in a cell of the central nervous system. In some embodiments, the cell is a neuron, astrocyte, or oligodendrocyte.

In some embodiments, an inhibitory nucleic acid is an miRNA. A "microRNA" or "miRNA" is a small non-coding RNA molecule capable of mediating transcriptional or post-translational gene silencing. Typically, miRNA is transcribed as a hairpin or stem-loop (e.g., having a self-complementarity, single-stranded backbone) duplex structure, referred to as a primary miRNA (pri-miRNA), which is enzymatically processed (e.g., by Drosha, DGCR8, Pasha, etc.) into a pre-miRNA. The length of a pri-miRNA can vary. In some embodiments, a pri-miRNA ranges from about 100 to about 5000 base pairs (e.g., about 100, about 200, about 500, about 1000, about 1200, about 1500, about 1800, or about 2000 base pairs) in length. In some embodiments, a pri-miRNA is greater than 200 base pairs in length (e.g., 2500, 5000, 7000, 9000, or more base pairs in length.

Pre-miRNA, which is also characterized by a hairpin or stem-loop duplex structure, can also vary in length. In some embodiments, pre-miRNA ranges in size from about 40 base pairs in length to about 500 base pairs in length. In some embodiments, pre-miRNA ranges in size from about 50 to 100 base pairs in length. In some embodiments, pre-miRNA ranges in size from about 50 to about 90 base pairs in length (e.g., about 50, about 52, about 54, about 56, about 58, about 60, about 62, about 64, about 66, about 68, about 70, about 72, about 74, about 76, about 78, about 80, about 82, about 84, about 86, about 88, or about 90 base pairs in length).

Generally, pre-miRNA is exported into the cytoplasm, and enzymatically processed by Dicer to first produce an imperfect miRNA/miRNA* duplex and then a single-stranded mature miRNA molecule, which is subsequently loaded into the RNA-induced silencing complex (RISC). Typically, a mature miRNA molecule ranges in size from about 19 to about 30 base pairs in length. In some embodiments, a mature miRNA molecule is about 19, about 20, about 21, about 22, about 23, about 24, about 25, about 26, about 27, about 28, about 29, or 30 base pairs in length. In some embodiments, an isolated nucleic acid of the disclosure comprises a sequence encoding a pri-miRNA, a pre-miRNA, or a mature miRNA comprising or encoded by a sequence set forth in SEQ ID NO: 4 (miR-SOD-127) and/or SEQ ID NO: 3.

In some aspects, the disclosure provides isolated nucleic acids and vectors (e.g., rAAV vectors) that encode one or more artificial miRNAs. As used herein "artificial miRNA" or "amiRNA" refers to an endogenous pri-miRNA or pre-miRNA (e.g., a miRNA backbone, which is a precursor miRNA capable of producing a functional mature miRNA), in which the miRNA and miRNA* (e.g., passenger strand of the miRNA duplex) sequences have been replaced with corresponding amiRNA/amiRNA* sequences that direct highly efficient RNA silencing of the targeted gene, for example as described by Eamens et al. (2014), Methods Mol. Biol. 1062:211-224. For example, in some embodiments an artificial miRNA comprises a miR-155 pri-miRNA backbone into which a sequence encoding a mature SOD1-specific miRNA (e.g., SEQ ID NO: 3 and/or 4; miR-SOD-127) has been inserted in place of the endogenous miR-155 mature miRNA-encoding sequence. In some embodiments, miRNA (e.g., an artificial miRNA) as described by the disclosure comprises a miR-155 backbone sequence, a miR-30 backbone sequence, a mir-64 backbone sequence, a miR-106 backbone, a miR-21 backbone, a miR-1 backbone, a miR-451 backbone, a miR-126 backbone, or a miR-122 backbone sequence. In some embodiments, the inhibitory nucleic acid is a microRNA comprising a targeting sequence having flanking regions of miR-155 or miR-30.

It should be appreciated that an isolated nucleic acid or vector (e.g., rAAV vector), in some embodiments comprises a nucleic acid sequence encoding more than one (e.g., a plurality, such as 2, 3, 4, 5, 10, or more) miRNAs. In some embodiments, each of the more than one miRNAs targets (e.g., hybridizes or binds specifically to) the same target gene (e.g., an isolated nucleic acid encoding three unique miRNAs, where each miRNA targets the SOD1 gene). In some embodiments, each of the more than one miRNAs targets (e.g., hybridizes or binds specifically to) a different target gene.

Isolated Nucleic Acids

In some aspects, the disclosure relates to isolated nucleic acids comprising a first expression construct encoding a synthetic microRNA for inhibiting expression of endogenous SOD1 and a second expression construct to express exogenous SOD1 resistant to the synthetic microRNA (miRNA).

A "nucleic acid" sequence refers to a DNA or RNA sequence. In some embodiments, proteins and nucleic acids of the disclosure are isolated. As used herein, the term "isolated" means artificially produced. As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. As used herein with respect to proteins or peptides, the term "isolated" refers to a protein or peptide that has been isolated from its natural environment or artificially produced (e.g., by chemical synthesis, by recombinant DNA technology, etc.).

Isolated nucleic acids of the disclosure typically comprise one or more regions that encode one or more inhibitory RNAs that target an endogenous mRNA (e.g., mRNA encoding endogenous wild-type SOD1 and/or endogenous mutant SOD1) of a subject. The isolated nucleic acids also typically comprise one or more regions that encode one or more exogenous mRNAs. The protein(s) encoded by the one or more exogenous mRNAs may or may not be different in sequence composition than the protein(s) encoded by the one or more endogenous mRNAs. For example, the one or more endogenous mRNAs may encode a wild-type and mutant version of a particular protein, such as may be the case when a subject is heterozygous for a particular mutation, and the exogenous mRNA may encode a wild-type mRNA of the same particular protein. In this case, typically the sequence of the exogenous mRNA and endogenous mRNA encoding the wild-type protein are sufficiently different such that the exogenous mRNA is not targeted by the one or more inhibitory RNAs. This may be accomplished, for example, by introducing one or more silent mutations into the exogenous mRNA such that it encodes the same protein as the endogenous mRNA but has a different nucleic acid sequence. In this case, the exogenous mRNA may be referred to as "hardened." Alternatively, the inhibitory RNA (e.g., miRNA) can target the 5' and/or 3' untranslated regions of the endogenous mRNA. These 5' and/or 3' regions can then be removed or replaced in the exogenous mRNA such that the exogenous mRNA is not targeted by the one or more inhibitory RNAs.

In another example, the one or more endogenous mRNAs may encode only mutant versions of a particular protein, such as may be the case when a subject is homozygous for a particular mutation, and the exogenous mRNA may encode a wild-type mRNA of the same particular protein. In this case, the sequence of the exogenous mRNA may be hardened as described above, or the one or more inhibitory RNAs may be designed to discriminate the mutated endogenous mRNA from the exogenous mRNA.

In some embodiments, the isolated nucleic acids typically comprise a first region that encodes one or more first inhibitory RNAs (e.g., miRNAs) comprising a nucleic acid having sufficient sequence complementary with an endogenous mRNA of a subject to hybridize with and inhibit expression of the endogenous mRNA (e.g., endogenous SOD1 mRNA). The isolated nucleic acids also typically include a second region encoding an exogenous mRNA (e.g., exogenous SOD1), in which the protein encoded by the exogenous mRNA has an amino acid sequence that is at least 95% identical to the first protein, in which the one or more first inhibitory RNAs do not comprise a nucleic acid having sufficient sequence complementary to hybridize with and inhibit expression of the exogenous mRNA. For example, the first region may be positioned at any suitable location. The first region may be positioned within an untranslated portion of the second region. The first region may be positioned in any untranslated portion of the nucleic acid, including, for example, an intron, a 5' or 3' untranslated region, etc.

A region comprising an inhibitory nucleic acid (e.g., a first region) may be positioned at any suitable location of the isolated nucleic acid. The region may be positioned in any untranslated portion of the nucleic acid, including, for example, an intron, a 5' or 3' untranslated region, etc.

In some cases, it may be desirable to position the region (e.g., the first region) upstream of the first codon of a nucleic acid sequence encoding a protein (such as a second region encoding an exogenous SOD1 protein coding sequence). For example, the region may be positioned between the first codon of a protein coding sequence and 2000 nucleotides upstream of the first codon. The region may be positioned between the first codon of a protein coding sequence and 1000 nucleotides upstream of the first codon. The region may be positioned between the first codon of a protein coding sequence and 500 nucleotides upstream of the first codon. The region may be positioned between the first codon of a protein coding sequence and 250 nucleotides upstream of the first codon. The region may be positioned between the first codon of a protein coding sequence and 150 nucleotides upstream of the first codon.

In some cases, it may be desirable to position the region (e.g., region encoding an inhibitory nucleic acid, such as a first region) upstream of the poly-A tail of a region encoding an exogenous SOD1 protein. For example, the region may be positioned between the first base of the poly-A tail and 2000 nucleotides upstream of the first base. The region may be positioned between the first base of the poly-A tail and 1000 nucleotides upstream of the first base. The region may be positioned between the first base of the poly-A tail and 500 nucleotides upstream of the first base. The region may be positioned between the first base of the poly-A tail and 250 nucleotides upstream of the first base. The region may be positioned between the first base of the poly-A tail and 150 nucleotides upstream of the first base. The region may be positioned between the first base of the poly-A tail and 100 nucleotides upstream of the first base. The region may be positioned between the first base of the poly-A tail and 50 nucleotides upstream of the first base. The region may be positioned between the first base of the poly-A tail and 20 nucleotides upstream of the first base. In some embodiments, the region is positioned between the last nucleotide base of a promoter sequence and the first nucleotide base of a poly-A tail sequence.

In some cases, a region encoding an inhibitory nucleic acid (e.g., a first region) may be positioned downstream of the last base of the poly-A tail of a region encoding an exogenous SOD1 protein. The region may be between the last base of the poly-A tail and a position 2000 nucleotides downstream of the last base. The region may be between the last base of the poly-A tail and a position 1000 nucleotides downstream of the last base. The region may be between the last base of the poly-A tail and a position 500 nucleotides downstream of the last base. The region may be between the last base of the poly-A tail and a position 250 nucleotides downstream of the last base. The region may be between the last base of the poly-A tail and a position 150 nucleotides downstream of the last base.

It should be appreciated that in cases where an isolated nucleic acid encodes more than one miRNA, each miRNA may be positioned in any suitable location within the construct. For example, a nucleic acid encoding a first miRNA may be positioned in an intron of the region encoding an exogenous SOD1 protein and a nucleic acid sequence encoding a second miRNA may be positioned in another region (e.g., between the last codon of a protein coding sequence and the first base of the poly-A tail of the transgene).

In some embodiments, an isolated nucleic acid further comprises a nucleic acid sequence encoding one or more expression control sequences (e.g., a promoter, etc.). Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

A "promoter" refers to a DNA sequence recognized by the synthetic machinery of the cell, or introduced synthetic machinery, required to initiate the specific transcription of a gene. The phrases "operatively positioned," "under control" or "under transcriptional control" means that the promoter is in the correct location and orientation in relation to the nucleic acid to control RNA polymerase initiation and expression of the gene.

For nucleic acids encoding proteins, a polyadenylation sequence generally is inserted following the transgene sequences and before the 3' AAV ITR sequence. A rAAV construct useful in the present disclosure may also contain an intron, desirably located between the promoter/enhancer sequence and the transgene. One possible intron sequence is derived from SV-40, and is referred to as the SV-40 T intron sequence. Another vector element that may be used is an internal ribosome entry site (IRES). An IRES sequence is used to produce more than one polypeptide from a single gene transcript. An IRES sequence would be used to produce a protein that contain more than one polypeptide chains. Selection of these and other common vector elements are conventional and many such sequences are available [see, e.g., Sambrook et al., and references cited therein at, for example, pages 3.18 3.26 and 16.17 16.27 and Ausubel et al., Current Protocols in Molecular Biology, John Wiley & Sons, New York, 1989]. In some embodiments, a Foot and Mouth Disease Virus 2A sequence is included in polyprotein; this is a small peptide (approximately 18 amino acids in length) that has been shown to mediate the cleavage of polyproteins (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459). The cleavage activity of the 2A sequence has previously been demonstrated in artificial systems including plasmids and gene therapy vectors (AAV and retroviruses) (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459; de Felipe, P et al., Gene Therapy, 1999; 6: 198-208; de Felipe, P et al., Human Gene Therapy, 2000; 11: 1921-1931.; and Klump, H et al., Gene Therapy, 2001; 8: 811-817).

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al., Cell, 41:521-530 (1985)], the SV40 promoter, the dihydrofolate reductase promoter, the β-actin promoter (e.g., CBA promoter), the phosphoglycerol kinase (PGK) promoter, and the EF1α promoter [Invitrogen]. In some embodiments, a promoter is an enhanced chicken β-actin promoter (CAG promoter). In some embodiments, a promoter is a H1 promoter or a U6 promoter.

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al., Proc. Natl. Acad. Sci. USA, 93:3346-3351 (1996)), the tetracycline-repressible system (Gossen et al., Proc. Natl. Acad. Sci. USA, 89:5547-5551 (1992)), the tetracycline-inducible system (Gossen et al., Science, 268:1766-1769 (1995), see also Harvey et al., Curr. Opin. Chem. Biol., 2:512-518 (1998)), the RU486-inducible system (Wang et al., Nat. Biotech., 15:239-243 (1997) and Wang et al., Gene Ther., 4:432-441 (1997)) and the rapamycin-inducible system (Magari et al., J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

In another embodiment, the native promoter for SOD1 (e.g., SEQ ID NO: 16) will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. Exemplary tissue-specific regulatory sequences include, but are not limited to the following tissue specific promoters: a liver-specific thyroxin binding globulin (TBG) promoter, an insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, a α-myosin heavy chain (a-MHC) promoter, or a cardiac Troponin T (cTnT) promoter. Other exemplary promoters include Beta-actin promoter, hepatitis B virus core promoter, Sandig et al., Gene Ther., 3:1002-9 (1996); alpha-fetoprotein (AFP) promoter, Arbuthnot et al., Hum. Gene Ther., 7:1503-14 (1996)), bone osteocalcin promoter (Stein et al., Mol. Biol. Rep., 24:185-96 (1997)); bone sialoprotein promoter (Chen et al., J. Bone Miner. Res., 11:654-64 (1996)), CD2 promoter (Hansal et al., J. Immunol., 161:1063-8 (1998); immunoglobulin heavy chain promoter; T cell receptor α-chain promoter, neuronal such as neuron-specific enolase (NSE) promoter (Andersen et al., Cell. Mol. Neurobiol., 13:503-15 (1993)), neurofilament light-chain gene promoter (Piccioli et al., Proc. Natl. Acad. Sci. USA, 88:5611-5 (1991)), and the neuron-specific vgf gene promoter (Piccioli et al., Neuron, 15:373-84 (1995)), among others which will be apparent to the skilled artisan.

Aspects of the disclosure relate to an isolated nucleic acid comprising more than one promoter (e.g., 2, 3, 4, 5, or more promoters). For example, in the context of a construct having a transgene comprising a first region encoding an inhibitory RNA (e.g., miRNA) and a second region encoding an exogenous SOD1 protein, it may be desirable to drive expression of the inhibitory RNA encoding region using a first promoter sequence (e.g., a first promoter sequence operably linked to the inhibitory nucleic acid encoding region), and to drive expression of the exogenous SOD1-encoding region with a second promoter sequence (e.g., a second promoter sequence operably linked to the exogenous SOD1-encoding region). Generally, the first promoter sequence and the second promoter sequence can be the same promoter sequence or different promoter sequences. In some embodiments, the first promoter sequence (e.g., the promoter driving expression of the protein coding region) is a RNA polymerase III (polIII) promoter sequence. Non-limiting examples of polIII promoter sequences include U6 and H1 promoter sequences. In some embodiments, the second promoter sequence (e.g., the promoter sequence driving expression of the exogenous SOD1 RNA) is a RNA polymerase II (polII) promoter sequence. Non-limiting examples of polII promoter sequences include chicken beta actin promoter (CBA), T7, T3, SP6, RSV, and cytomegalovirus promoter sequences. In some embodiments, a polIII promoter sequence drives expression of an inhibitory RNA (e.g., miRNA) encoding region. In some embodiments, a polII promoter sequence drives expression of a protein coding region.

As described further below, the isolated nucleic acids may comprise inverted terminal repeats (ITR) of an AAV serotypes selected from the group consisting of: AAV1, AAV2, AAV5, AAV6, AAV6.2, AAV7, AAV8, AAV9, AAV10, AAV11 and variants thereof.

Multicistronic Constructs

Some aspects of this invention provide multicistronic (e.g., bicistronic) expression constructs comprising two or more expression cassettes in various configurations.

In different embodiments, multicistronic (e.g., bicistronic) expression constructs are provided in which the expression cassettes are positioned in different ways. For example, in some embodiments, a multicistronic expression construct is provided in which a first expression cassette is positioned adjacent to a second expression cassette. In some embodiments, a multicistronic expression construct is provided in which a first expression cassette comprises an intron, and a second expression cassette is positioned within the intron of the first expression cassette. In some embodiments, the second expression cassette, positioned within an intron of the first expression cassette, comprises a promoter and a nucleic acid sequence encoding a gene product operatively linked to the promoter.

In different embodiments, multicistronic (e.g., bicistronic) expression constructs are provided in which the expression cassettes are oriented in different ways. For example, in some embodiments, a multicistronic expression construct is provided in which a first expression cassette is in the same orientation as a second expression cassette. In some embodiments, a multicistronic expression construct is provided comprising a first and a second expression cassette in opposite orientations.

The term "orientation" as used herein in connection with expression cassettes, refers to the directional characteristic of a given cassette or structure. In some embodiments, an expression cassette harbors a promoter 5' of the encoding nucleic acid sequence, and transcription of the encoding nucleic acid sequence runs from the 5' terminus to the 3' terminus of the sense strand, making it a directional cassette (e.g. 5'-promoter/(intron)/encoding sequence-3'). Since virtually all expression cassettes are directional in this sense, those of skill in the art can easily determine the orientation of a given expression cassette in relation to a second nucleic acid structure, for example, a second expression cassette, a viral genome, or, if the cassette is comprised in an AAV construct, in relation to an AAV ITR.

For example, if a given nucleic acid construct comprises two expression cassettes in the configuration 5'-promoter 1/encoding sequence 1 - - - promoter 2/encoding sequence 2-3',

>>>>>>>>>>>>>>>>>>>>>>>>
>>>>>>>>>>>>>>>>>>>>>>>> the expression cassettes are in the same orientation, the arrows indicate the direction of transcription of each of the cassettes. For another example, if a given nucleic acid construct comprises a sense strand comprising two expression cassettes in the configuration 5'-promoter 1/encoding sequence 1 - - - encoding sequence 2/promoter 2-3',

>>>>>>>>>>>>>>>>>>>>>>>>
<<<<<<<<<<<<<<<<<<<<<<<< the expression cassettes are in opposite orientation to each other and, as indicated by the arrows, the direction of transcription of the expression cassettes, are opposed. In this example, the strand shown comprises the antisense strand of promoter 2 and encoding sequence 2.

Figure 5:
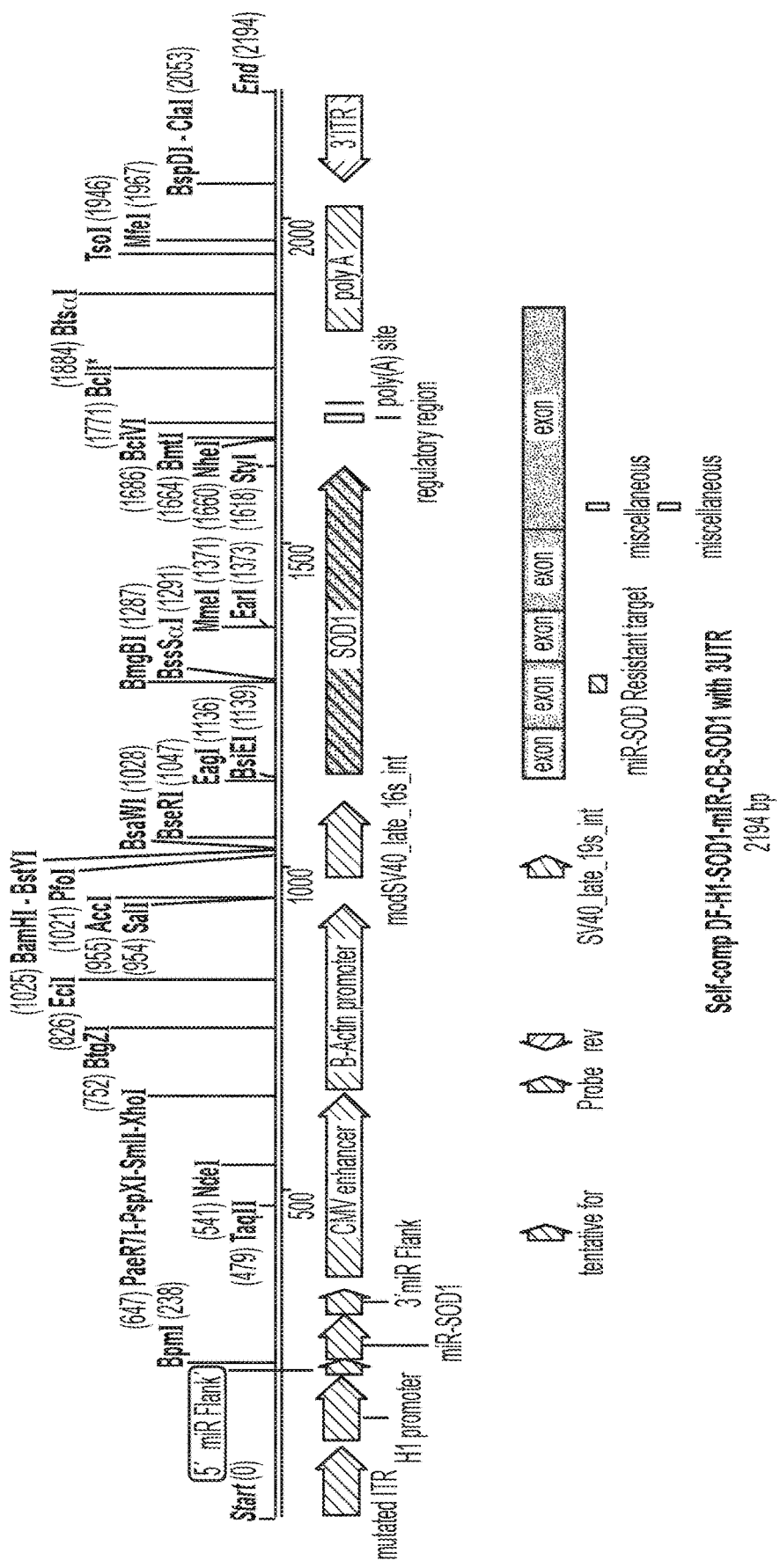
FIG. 5 shows a schematic overview of construct design for a bicistronic dual function self-complementary AAV vector. The anti-Sod1 miRNA is expressed by an H1 promoter and the miRNA-resistant SOD1 cDNA is expressed by a chicken beta actin promoter and CMV enhancer (e.g., CAG promoter). The locus of the SOD1 cDNA containing a silent mutation relative to wild-type SOD1 is shown ("miR-SOD Resistant Target"). A mutant AAV inverted terminal repeat (ITR) is present on the 5' end of the construct and a full-length AAV ITR is located at the 3' end.
Figure 6:
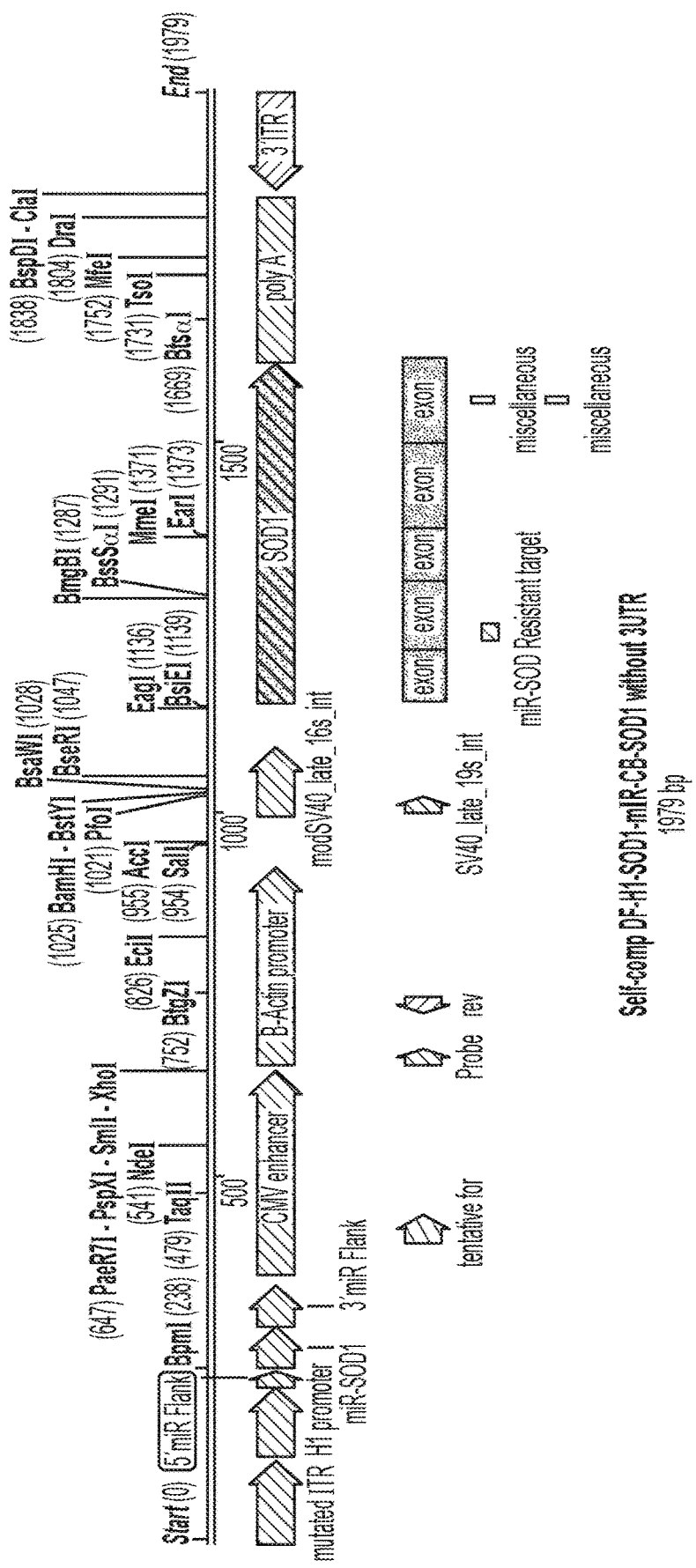
FIG. 6 shows a schematic overview of construct design for a bicistronic dual function self-complementary AAV vector. The anti-Sod1 miRNA is expressed by an H1 promoter and the miRNA-resistant SOD1 cDNA is expressed by a chicken beta actin promoter and CMV enhancer (e.g., CAG promoter). The locus of the SOD1 cDNA containing a silent mutation relative to wild-type SOD1 is shown ("miR-SOD Resistant Target"). The SOD1 expression construct lacks a 3'UTR. A mutant AAV inverted terminal repeat (ITR) is present on the 5' end of the construct and a full-length AAV ITR is located at the 3' end.
Figure 7:
FIG. 7 shows a schematic overview of construct design for a single promoter dual function AAV vector. The anti-Sod1 miRNA and miRNA-resistant SOD1 cDNA are both expressed by a chicken beta actin promoter and CMV enhancer (e.g., CAG promoter). The locus of the SOD1 cDNA containing a silent mutation relative to wild-type SOD1 is shown ("miR-SOD Resistant Target"). The anti-Sod1 miR is located in an intron. AAV ITRs are located at the 5' and 3' ends of the construct.
Figure 8:
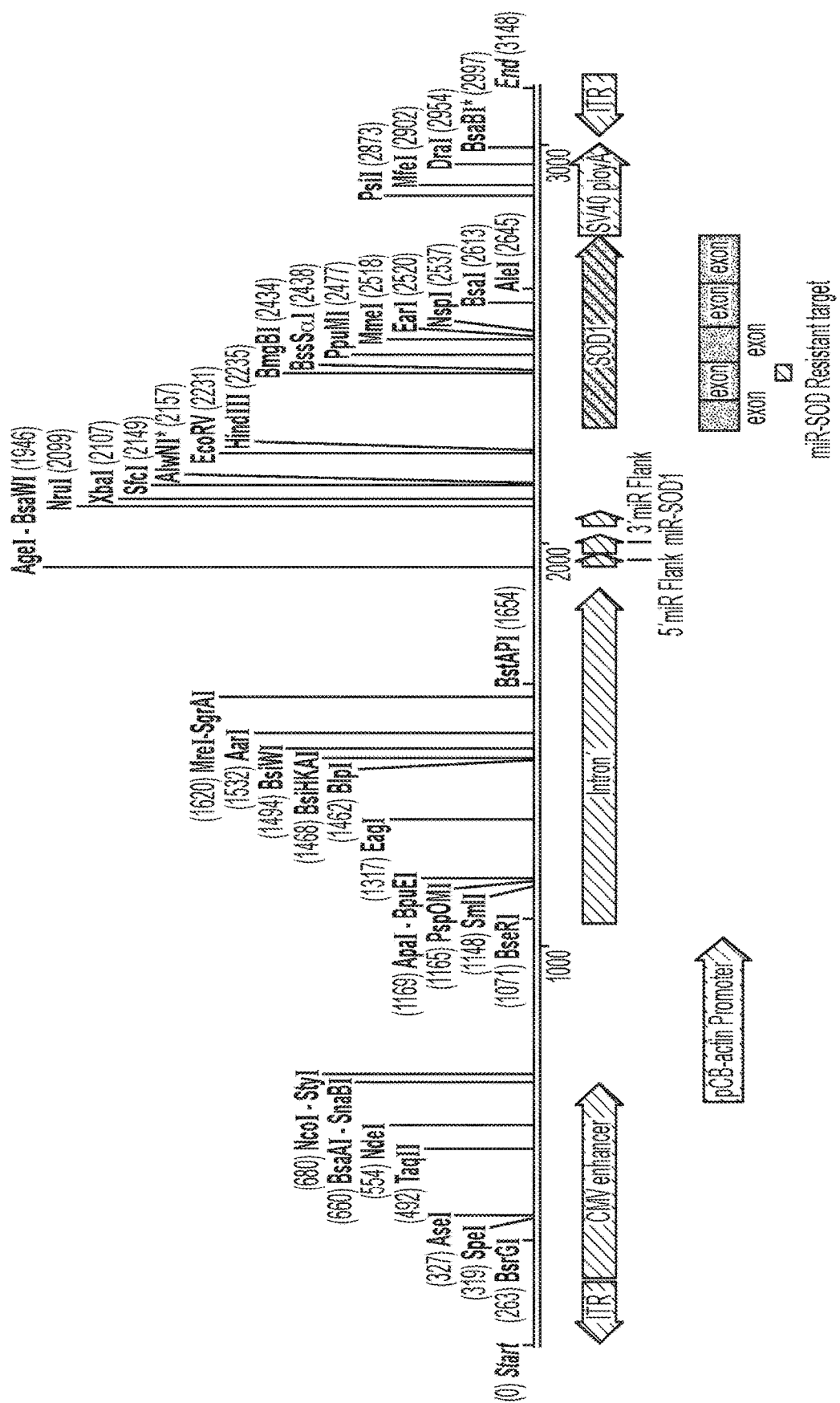
FIG. 8 shows a schematic overview of construct design for a single promoter dual function AAV vector. The anti-Sod1 miRNA and miRNA-resistant SOD1 cDNA are both expressed by a chicken beta actin promoter and CMV enhancer (e.g., CAG promoter). The locus of the SOD1 cDNA containing a silent mutation relative to wild-type SOD1 is shown ("miR-SOD Resistant Target"). The SOD1 expression construct lacks a 3'UTR. The anti-Sod1 miR is located in an intron. AAV ITRs are located at the 5' and 3' ends of the construct.

For another example, if an expression cassette is comprised in an AAV construct, the cassette can either be in the same orientation as an AAV ITR (e.g. the structures depicted in FIG. 5, etc.), or in opposite orientation. AAV ITRs are directional. For example, the mutated 5'ITR exemplified in FIG. 5 would be in the same orientation as the H1 promoter/inhibitory RNA-encoding expression cassette, but in opposite orientation to the 3'ITR, if both ITRs and the expression cassette would be on the same nucleic acid strand.

rAAV Vectors

The isolated nucleic acids of the invention may be recombinant adeno-associated virus (AAV) vectors (rAAV vectors). In some embodiments, an isolated nucleic acid as described by the disclosure comprises a region (e.g., a first region) comprising a first adeno-associated virus (AAV) inverted terminal repeat (ITR), or a variant thereof. The isolated nucleic acid (e.g., the recombinant AAV vector) may be packaged into a capsid protein and administered to a subject and/or delivered to a selected target cell. "Recombinant AAV (rAAV) vectors" are typically composed of, at a minimum, a transgene and its regulatory sequences, and 5' and 3' AAV inverted terminal repeats (ITRs). The transgene may comprise, as disclosed elsewhere herein, one or more regions that encode one or more inhibitory RNAs (e.g., miRNAs) comprising a nucleic acid that targets an endogenous mRNA of a subject. The transgene may also comprise a region encoding, for example, a protein and/or an expression control sequence (e.g., a poly-A tail), as described elsewhere in the disclosure.

Generally, ITR sequences are about 145 base pairs (bp) in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al., "Molecular Cloning. A Laboratory Manual", 2d ed., Cold Spring Harbor Laboratory, New York (1989); and K. Fisher et al., J Virol., 70:520 532 (1996)). An example of such a molecule employed in the present invention is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types. In some embodiments, the isolated nucleic acid (e.g., the rAAV vector) comprises at least one ITR having a serotype selected from AAV1, AAV2, AAV5, AAV6, AAV6.2, AAV7, AAV8, AAV9, AAV10, AAV11, and variants thereof. In some embodiments, the isolated nucleic acid comprises a region (e.g., a first region) encoding an AAV2 ITR.

In some embodiments, the isolated nucleic acid further comprises a region (e.g., a second region, a third region, a fourth region, etc.) comprising a second AAV ITR. In some embodiments, the second AAV ITR has a serotype selected from AAV1, AAV2, AAV5, AAV6, AAV6.2, AAV7, AAV8, AAV9, AAV10, AAV11, and variants thereof. In some embodiments, the second ITR is a mutant ITR that lacks a functional terminal resolution site (TRS). The term "lacking a terminal resolution site" can refer to an AAV ITR that comprises a mutation (e.g., a sense mutation such as a non-synonymous mutation, or missense mutation) that abrogates the function of the terminal resolution site (TRS) of the ITR, or to a truncated AAV ITR that lacks a nucleic acid sequence encoding a functional TRS (e.g., a ΔTRS ITR). Without wishing to be bound by any particular theory, a rAAV vector comprising an ITR lacking a functional TRS produces a self-complementary rAAV vector, for example as described by McCarthy (2008) Molecular Therapy 16(10): 1648-1656.

In addition to the major elements identified above for the recombinant AAV vector, the vector also includes conventional control elements which are operably linked with elements of the transgene in a manner that permits its transcription, translation and/or expression in a cell transfected with the vector or infected with the virus produced by the invention. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A number of expression control sequences, including promoters which are native, constitutive, inducible and/or tissue-specific, are known in the art and may be utilized.

As used herein, a nucleic acid sequence (e.g., coding sequence) and regulatory sequences are said to be operably linked when they are covalently linked in such a way as to place the expression or transcription of the nucleic acid sequence under the influence or control of the regulatory sequences. If it is desired that the nucleic acid sequences be translated into a functional protein, two DNA sequences are said to be operably linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly two or more coding regions are operably linked when they are linked in such a way that their transcription from a common promoter results in the expression of two or more proteins having been translated in frame. In some embodiments, operably linked coding sequences yield a fusion protein.

Recombinant Adeno-Associated Viruses (rAAVs)

In some aspects, the disclosure provides isolated AAVs. As used herein with respect to AAVs, the term "isolated" refers to an AAV that has been artificially produced or obtained. Isolated AAVs may be produced using recombinant methods. Such AAVs are referred to herein as "recombinant AAVs". Recombinant AAVs (rAAVs) preferably have tissue-specific targeting capabilities, such that a nuclease and/or transgene of the rAAV will be delivered specifically to one or more predetermined tissue(s). The AAV capsid is an important element in determining these tissue-specific targeting capabilities. Thus, an rAAV having a capsid appropriate for the tissue being targeted can be selected.

Methods for obtaining recombinant AAVs having a desired capsid protein are well known in the art. (See, for example, US 2003/0138772), the contents of which are incorporated herein by reference in their entirety). Typically the methods involve culturing a host cell which contains a nucleic acid sequence encoding an AAV capsid protein; a functional rep gene; a recombinant AAV vector composed of, AAV inverted terminal repeats (ITRs) and a transgene; and sufficient helper functions to permit packaging of the recombinant AAV vector into the AAV capsid proteins. In some embodiments, capsid proteins are structural proteins encoded by the cap gene of an AAV. AAVs comprise three capsid proteins, virion proteins 1 to 3 (named VP1, VP2 and VP3), all of which are transcribed from a single cap gene via alternative splicing. In some embodiments, the molecular weights of VP1, VP2 and VP3 are respectively about 87 kDa, about 72 kDa and about 62 kDa. In some embodiments, upon translation, capsid proteins form a spherical 60-mer protein shell around the viral genome. In some embodiments, the functions of the capsid proteins are to protect the viral genome, deliver the genome and interact with the host. In some aspects, capsid proteins deliver the viral genome to a host in a tissue specific manner.

In some embodiments, an AAV capsid protein is of an AAV serotype selected from the group consisting of AAV2, AAV3, AAV4, AAV5, AAV6, AAV8, AAVrh8, AAV9, AAV10, AAVrh.10, AAV AAV.PHB, and variants of any of the foregoing. In some embodiments, an AAV capsid protein is of a serotype derived from a non-human primate, for example AAVrh10 serotype. In some embodiments, an AAV capsid protein is of an AAV9 serotype.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

In some embodiments, the instant disclosure relates to a host cell containing a nucleic acid that comprises sequence encoding an inhibitory nucleic acid targeting endogenous SOD1 and a sequence encoding an exogenous protein (e.g., exogenous SOD1 protein, optionally "hardened" exogenous SOD1 protein). In some embodiments, the instant disclosure relates to a composition comprising the host cell described above. In some embodiments, the composition comprising the host cell above further comprises a cryopreservative.

The recombinant AAV vector, rep sequences, cap sequences, and helper functions required for producing the rAAV of the disclosure may be delivered to the packaging host cell using any appropriate genetic element (vector). The selected genetic element may be delivered by any suitable method, including those described herein. The methods used to construct any embodiment of this disclosure are known to those with skill in nucleic acid manipulation and include genetic engineering, recombinant engineering, and synthetic techniques. See, e.g., Sambrook et al., Molecular Cloning: A Laboratory Manual, Cold Spring Harbor Press, Cold Spring Harbor, N.Y. Similarly, methods of generating rAAV virions are well known and the selection of a suitable method is not a limitation on the present disclosure. See, e.g., K. Fisher et al., J. Virol., 70:520-532 (1993) and U.S. Pat. No. 5,478,745.

In some embodiments, recombinant AAVs may be produced using the triple transfection method (described in detail in U.S. Pat. No. 6,001,650). Typically, the recombinant AAVs are produced by transfecting a host cell with an recombinant AAV vector (comprising a transgene) to be packaged into AAV particles, an AAV helper function vector, and an accessory function vector. An AAV helper function vector encodes the "AAV helper function" sequences (i.e., rep and cap), which function in trans for productive AAV replication and encapsidation. Preferably, the AAV helper function vector supports efficient AAV vector production without generating any detectable wild-type AAV virions (i.e., AAV virions containing functional rep and cap genes). Non-limiting examples of vectors suitable for use with the present disclosure include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus.

In some aspects, the disclosure provides transfected host cells. The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells.

A "host cell" refers to any cell that harbors, or is capable of harboring, a substance of interest. Often a host cell is a mammalian cell. A host cell may be used as a recipient of an AAV helper construct, an AAV minigene plasmid, an accessory function vector, or other transfer DNA associated with the production of recombinant AAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors. In some embodiments, useful vectors are contemplated to be those vectors in which the nucleic acid segment to be transcribed is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned," "under control" or "under transcriptional control" means that the promoter is in the correct location and orientation in relation to the nucleic acid to control RNA polymerase initiation and expression of the gene. The term "expression vector or construct" means any type of genetic construct containing a nucleic acid in which part or all of the nucleic acid encoding sequence is capable of being transcribed. In some embodiments, expression includes transcription of the nucleic acid, for example, to generate a biologically-active polypeptide product or functional RNA (e.g., guide RNA) from a transcribed gene.

The foregoing methods for packaging recombinant vectors in desired AAV capsids to produce the rAAVs of the disclosure are not meant to be limiting and other suitable methods will be apparent to the skilled artisan.

Modes of Administration

Isolated nucleic acids and rAAVs of the disclosure may be delivered to a cell or subject in compositions according to any appropriate methods known in the art. For example, an rAAV, preferably suspended in a physiologically compatible carrier (i.e., in a composition), may be administered to a subject, i.e. host animal, such as a human, mouse, rat, cat, dog, sheep, rabbit, horse, cow, goat, pig, guinea pig, hamster, chicken, turkey, or a non-human primate (e.g., Macaque). In some embodiments a host animal does not include a human.

Delivery of the rAAVs to a mammalian subject may be by, for example, intramuscular injection or by administration into the bloodstream of the mammalian subject. Administration into the bloodstream may be by injection into a vein, an artery, or any other vascular conduit. In some embodiments, the rAAVs are administered into the bloodstream by way of isolated limb perfusion, a technique well known in the surgical arts, the method essentially enabling the artisan to isolate a limb from the systemic circulation prior to administration of the rAAV virions. A variant of the isolated limb perfusion technique, described in U.S. Pat. No. 6,177,403, can also be employed by the skilled artisan to administer the virions into the vasculature of an isolated limb to potentially enhance transduction into muscle cells or tissue. Moreover, in certain instances, it may be desirable to deliver the virions to the CNS of a subject. By "CNS" is meant all cells and tissue of the brain and spinal cord of a vertebrate. Thus, the term includes, but is not limited to, neuronal cells, glial cells, astrocytes, cerebrospinal fluid (CSF), interstitial spaces, bone, cartilage and the like. Recombinant AAVs may be delivered directly to the CNS or brain by injection into, e.g., the ventricular region, as well as to the striatum (e.g., the caudate nucleus or putamen of the striatum), spinal cord and neuromuscular junction, or cerebellar lobule, with a needle, catheter or related device, using neurosurgical techniques known in the art, such as by stereotactic injection (see, e.g., Stein et al., J Virol 73:3424-3429, 1999; Davidson et al., PNAS 97:3428-3432, 2000; Davidson et al., Nat. Genet. 3:219-223, 1993; and Alisky and Davidson, Hum. Gene Ther. 11:2315-2329, 2000). In some embodiments, rAAV as described in the disclosure are administered by intravenous injection. In some embodiments, the rAAV are administered by intracerebral injection. In some embodiments, the rAAV are administered by intrathecal injection. In some embodiments, the rAAV are administered by intrastriatal injection. In some embodiments, the rAAV are delivered by intracranial injection. In some embodiments, the rAAV are delivered by cisterna magna injection. In some embodiments, the rAAV are delivered by cerebral lateral ventricle injection.

Aspects of the instant disclosure relate to compositions comprising a recombinant AAV comprising a capsid protein and a nucleic acid encoding a transgene, wherein the transgene comprises a nucleic acid sequence encoding one or more miRNAs. In some embodiments, each miRNA comprises or is encoded by a sequence set forth in SEQ ID NO: 3 and/or 4 (miR-SOD-127). In some embodiments, each miRNA comprises or is encoded by a sequence set forth in SEQ ID NO: 5 and/or 6. In some embodiments, the nucleic acid further comprises AAV ITRs. In some embodiments, the rAAV comprises an rAAV vector represented by the sequence set forth in any one of SEQ ID NO: 8-15 (AAV vector sequences), or a portion thereof. In some embodiments, a composition further comprises a pharmaceutically acceptable carrier.

The compositions of the disclosure may comprise an rAAV alone, or in combination with one or more other viruses (e.g., a second rAAV encoding having one or more different transgenes). In some embodiments, a composition comprises 1, 2, 3, 4, 5, 6, 7, 8, 9, 10, or more different rAAVs each having one or more different transgenes.

Suitable carriers may be readily selected by one of skill in the art in view of the indication for which the rAAV is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present disclosure.

Optionally, the compositions of the disclosure may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The rAAVs are administered in sufficient amounts to transfect the cells of a desired tissue and to provide sufficient levels of gene transfer and expression without undue adverse effects. Conventional and pharmaceutically acceptable routes of administration include, but are not limited to, direct delivery to the selected organ (e.g., intraportal delivery to the liver), oral, inhalation (including intranasal and intratracheal delivery), intraocular, intravenous, intramuscular, subcutaneous, intradermal, intratumoral, and other parental routes of administration. Routes of administration may be combined, if desired.

The dose of rAAV virions required to achieve a particular "therapeutic effect," e.g., the units of dose in genome copies/per kilogram of body weight (GC/kg), will vary based on several factors including, but not limited to: the route of rAAV virion administration, the level of gene or RNA expression required to achieve a therapeutic effect, the specific disease or disorder being treated, and the stability of the gene or RNA product. One of skill in the art can readily determine a rAAV virion dose range to treat a patient having a particular disease or disorder based on the aforementioned factors, as well as other factors that are well known in the art.

An effective amount of an rAAV is an amount sufficient to target infect an animal, target a desired tissue. In some embodiments, an effective amount of an rAAV is an amount sufficient to produce a stable somatic transgenic animal model. The effective amount will depend primarily on factors such as the species, age, weight, health of the subject, and the tissue to be targeted, and may thus vary among animal and tissue. For example, an effective amount of the rAAV is generally in the range of from about 1 ml to about 100 ml of solution containing from about $10^9$ to $10^{16}$ genome copies. In some cases, a dosage between about $10^{11}$ to $10^{13}$ rAAV genome copies is appropriate. In certain embodiments, $10^{12}$ or $10^{13}$ rAAV genome copies is effective to target CNS tissue. In some cases, stable transgenic animals are produced by multiple doses of an rAAV.

In some embodiments, a dose of rAAV is administered to a subject no more than once per calendar day (e.g., a 24-hour period). In some embodiments, a dose of rAAV is administered to a subject no more than once per 2, 3, 4, 5, 6, or 7 calendar days. In some embodiments, a dose of rAAV is administered to a subject no more than once per calendar week (e.g., 7 calendar days). In some embodiments, a dose of rAAV is administered to a subject no more than bi-weekly (e.g., once in a two calendar week period). In some embodiments, a dose of rAAV is administered to a subject no more than once per calendar month (e.g., once in 30 calendar days). In some embodiments, a dose of rAAV is administered to a subject no more than once per six calendar months. In some embodiments, a dose of rAAV is administered to a subject no more than once per calendar year (e.g., 365 days or 366 days in a leap year).

In some embodiments, rAAV compositions are formulated to reduce aggregation of AAV particles in the composition, particularly where high rAAV concentrations are present (e.g., ~$10^{13}$ GC/ml or more). Methods for reducing aggregation of rAAVs are well known in the art and, include, for example, addition of surfactants, pH adjustment, salt concentration adjustment, etc. (See, e.g., Wright F R, et al., Molecular Therapy (2005) 12, 171-178, the contents of which are incorporated herein by reference.)

Formulation of pharmaceutically-acceptable excipients and carrier solutions is well-known to those of skill in the art, as is the development of suitable dosing and treatment regimens for using the particular compositions described herein in a variety of treatment regimens.

Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In certain circumstances it will be desirable to deliver the rAAV-based therapeutic constructs in suitably formulated pharmaceutical compositions disclosed herein either subcutaneously, intraopancreatically, intranasally, parenterally, intravenously, intramuscularly, intrathecally, or orally, intraperitoneally, or by inhalation. In some embodiments, the administration modalities as described in U.S. Pat. Nos. 5,543,158; 5,641,515 and 5,399,363 (each specifically incorporated herein by reference in its entirety) may be used to deliver rAAVs. In some embodiments, a preferred mode of administration is by portal vein injection.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active rAAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The rAAV compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present disclosure into suitable host cells. In particular, the rAAV vector delivered transgenes may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the rAAV constructs disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 Å, containing an aqueous solution in the core.

Alternatively, nanocapsule formulations of the rAAV may be used. Nanocapsules can generally entrap substances in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use.

In addition to the methods of delivery described above, the following techniques are also contemplated as alternative methods of delivering the rAAV compositions to a host. Sonophoresis (i.e., ultrasound) has been used and described in U.S. Pat. No. 5,656,016 as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. Nos. 5,770,219 and 5,783,208) and feedback-controlled delivery (U.S. Pat. No. 5,697,899).

Methods of Use

Methods are provided herein for inhibiting the expression of genes that are associated with FTD and/or ALS, such as SOD1. In some embodiments, methods described by the disclosure are useful for treating a subject having or suspected of having ALS and/or FTD. As used herein "treat" or "treating" refers to (a) preventing or delaying onset of neurodegenerative disease (e.g., ALS/FTD, etc.); (b) reducing severity of ALS/FTD; (c) reducing or preventing development of symptoms characteristic of ALS/FTD; (d) and/or preventing worsening of symptoms characteristic of ALS/FTD.

In some embodiments, methods are provided for inhibiting endogenous SOD1 protein expression in a subject (e.g., the central nervous system (CNS) of a subject). In some embodiments, the methods involve administering to the subject (e.g., administering to the CNS of the subject) an isolated nucleic acid or rAAV engineered to express an inhibitory nucleic acid that targets endogenous SOD1 mRNA and an exogenous SOD1 mRNA transcript that is resistant to the inhibitory nucleic acid. In some embodiments, the subject has or is suspected of having FTD or ALS (e.g., has been identified, for example by diagnostic DNA testing, as having a SOD1 gene having one or more mutations leading to a toxic gain of function and/or exhibits one or more signs or symptoms of ALS). In some embodiments, the methods involve administering to the subject an effective amount of a recombinant adeno-associated virus (rAAV) harboring a nucleic acid that is engineered to express, in a cell of the subject, an inhibitory nucleic acid that targets endogenous SOD1 mRNA. In some embodiments, the inhibitory nucleic acid comprises or is encoded by a sequence as set forth in SEQ ID NO: 3 (GACGTACCTAAGGTACAAGTA) and/or 4 (miR-SOD-127). In some embodiments, the inhibitory nucleic acid comprises or is encoded by a sequence as set forth in SEQ ID NO: 5 and/or 6.

In some embodiments, methods are provided for inhibiting SOD1 expression in a cell. In some embodiments, the methods involve delivering to the cell an isolated nucleic acid or rAAV as described by the disclosure, wherein the inhibitory RNA is an miRNA that comprises or is encoded by 5, 6, 7, 8, 9, 10, 11, 12, 13, 14, 15, 16, 17, 18, 19, 20 or 21 consecutive nucleotides of a sequence set forth in SEQ ID NO: 3 (GACGTACCTAAGGTACAAGTA) and/or 4 (CTGCATGGATTCCATGTTCAT), or of a complementary sequence of that sequence.

In accordance with the foregoing, certain methods provided herein involve administering to a subject an effective amount of a recombinant Adeno-Associated Virus (rAAV) harboring any of the recombinant nucleic acids disclosed herein. In general, the "effective amount" of a rAAV refers to an amount sufficient to elicit the desired biological response. In some embodiments, the effective amount refers to the amount of rAAV effective for transducing a cell or tissue ex vivo. In other embodiments, the effective amount refers to the amount effective for direct administration of rAAV to a subject. As will be appreciated by those of ordinary skill in this art, the effective amount of the recombinant AAV of the invention varies depending on such factors as the desired biological endpoint, the pharmacokinetics of the expression products, the condition being treated, the mode of administration, and the subject. Typically, the rAAV is administered with a pharmaceutically acceptable carrier, as described elsewhere in this disclosure.

In some instances, after administration of the rAAV at least one clinical outcome parameter or biomarker (e.g., intranuclear G4C2 RNA foci, RAN-protein expression, etc.) associated with the FTD or ALS is evaluated in the subject. Typically, the clinical outcome parameter or biomarker evaluated after administration of the rAAV is compared with the clinical outcome parameter or biomarker determined at a time prior to administration of the rAAV to determine effectiveness of the rAAV. Often an improvement in the clinical outcome parameter or biomarker after administration of the rAAV indicates effectiveness of the rAAV. Any appropriate clinical outcome parameter or biomarker may be used. Typically, the clinical outcome parameter or biomarker is indicative of the one or more symptoms of an FTD or ALS. For example, in some embodiments, the clinical outcome parameter or biomarker may be endogenous SOD1 expression, memory loss, or presence or absence of movement disorders such as unsteadiness, rigidity, slowness, twitches, muscle weakness or difficulty swallowing, speech and language difficulties, twitching (fasciculation) and cramping of muscles, including those in the hands and feet.

Kits and Related Compositions

The recombinant nucleic acids, compositions, rAAV vectors, rAAVs, etc. described herein may, in some embodiments, be assembled into pharmaceutical or diagnostic or research kits to facilitate their use in therapeutic, diagnostic or research applications. A kit may include one or more containers housing the components of the invention and instructions for use. Specifically, such kits may include one or more agents described herein, along with instructions describing the intended application and the proper use of these agents. In certain embodiments agents in a kit may be in a pharmaceutical formulation and dosage suitable for a particular application and for a method of administration of the agents. Kits for research purposes may contain the components in appropriate concentrations or quantities for running various experiments.

The kit may be designed to facilitate use of the methods described herein by researchers and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for animal administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be in the form of a liquid, gel or solid (powder). The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container. The kit may have one or more or all of the components required to administer the agents to a subject, such as a syringe, topical application devices, or IV needle tubing and bag.

Exemplary embodiments of the invention will be described in more detail by the following examples. These embodiments are exemplary of the invention, which one skilled in the art will recognize is not limited to the exemplary embodiments.

EXAMPLES

Example 1

This example describes dual expression gene therapy vectors that couple delivery of (1) a first construct engineered to express synthetic microRNA to silence expression of endogenous cytosolic Cu/Zn superoxide dismutase (SOD1) activity with (2) a second construct engineered to express wildtype SOD1 resistant to the synthetic microRNA.

The rationale for coupling SOD1 silencing via AAVrh10-antiSOD1-miRNA with expression of WT SOD1 resistant to the synthetic microRNA is based on two factors. First, the dismutation activity of the SOD1 protein has neuroprotective properties. Second, the tissues (and specifically the motor neurons) of ALS cases in which SOD1 is silenced are not normal, precisely because they express both wild-type (WT) and mutant SOD1. Indeed, when SOD1 silencing studies are initiated after disease onset, the motor neurons (and some non-neuronal cells) are already observed to be manifestly pathological. In this situation, to eliminate the SOD1 dismutation activity conferred by the WT SOD1 molecule (and also dismutation activity that can arise from some mutant SOD1 proteins) is also to eliminate potentially neuroprotective influences conferred by that activity. The net effect on the cells therefore reflects a balance of two opposite factors: (a) silencing the mutant protein and its neurotoxicity versus (b) eliminating the neuroprotective influence of the SOD1 dismutation activity. In a sick motor neuron, it is conceivable that the net effect may be to further compromise the viability of the targeted cell, despite simultaneous reduction in levels of the mutant protein. Consistent with this observation, it is noted that while mice devoid of intrinsic SOD1 activity do not develop fulminant ALS during normal development, their motor neurons are highly susceptible to superimposed injury; facial nerves injury in those SOD1-negative mice leads to much more extensive loss of facial nerves than in WT mice. Moreover, late in life these SOD1- negative mice have been observed to develop a slowly progressive, late-onset motor neuronpathy.

The dual expression gene constructs described by the disclosure address the challenge of loss of neuroprotective activity from SOD1 dismutation. The arrangement of gene expression cassettes in constructs of the disclosure allows for normal levels of SOD1 dismutation activity (e.g., expression of WT SOD1) even with total silencing of both WT and mutant endogenous SOD1 alleles. Thus, the net effect of the constructs described herein is a reduction in levels of the mutant SOD1 protein (but not WT SOD1 protein), which is beneficial in SOD1-mediated ALS.

Figure 1:
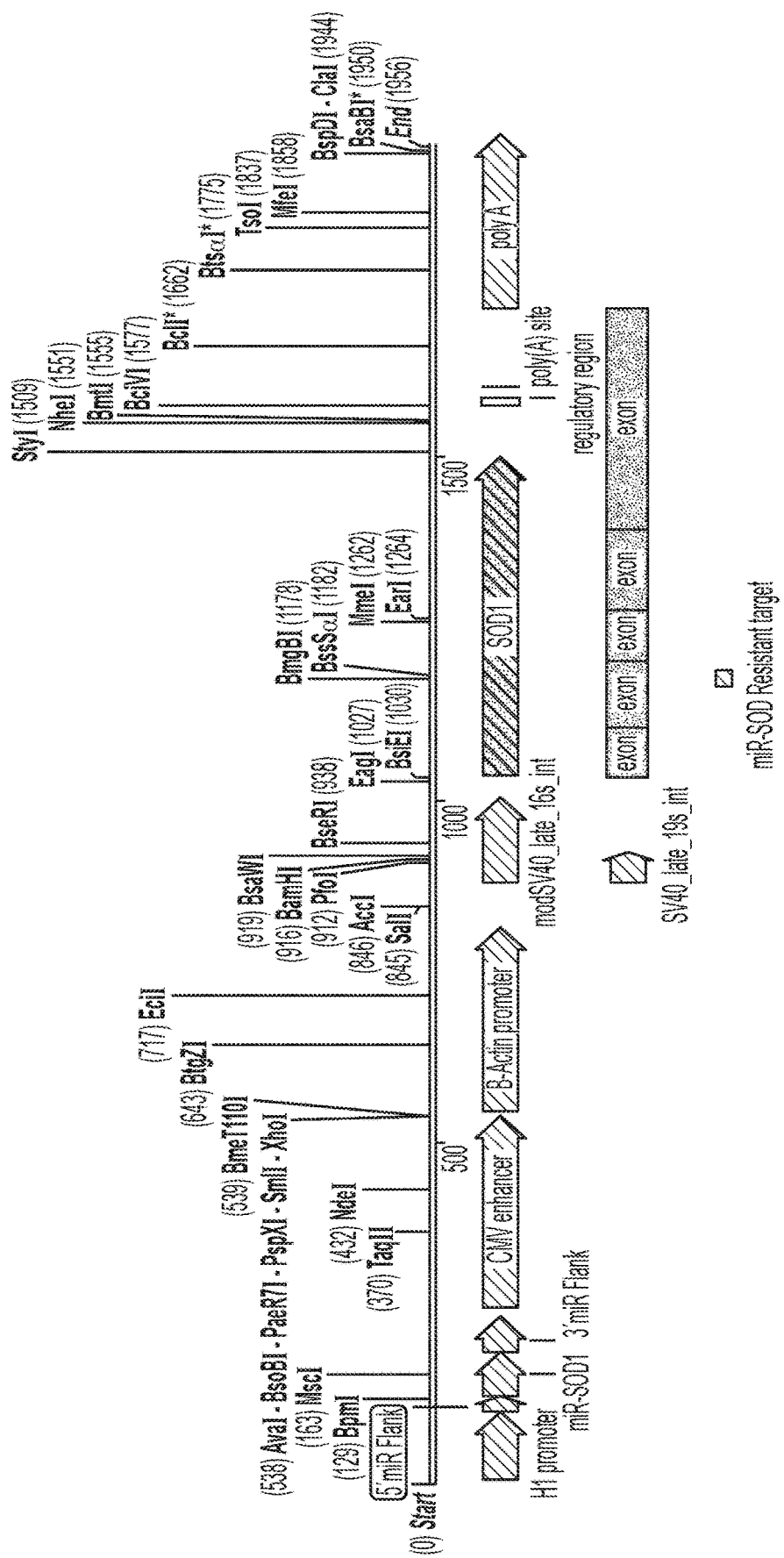
FIG. 1 shows a schematic overview of construct design for a bicistronic dual function vector. The anti-Sod1 miRNA is expressed by an H1 promoter and the miRNA-resistant SOD1 cDNA is expressed by a chicken beta actin promoter and CMV enhancer (e.g., CAG promoter).

Dual expression constructs of the disclosure are constructed as follows: an AAV construct that expresses both an artificial miRNAs that targets SOD1 and a SOD1 cDNA that has silent base pair modification that makes it resistant to the artificial miRNA is produced. This construct simultaneously allows silencing of mutant SOD1 and augmented expression of wildtype SOD1 from a single AAV vector. In some embodiments, the construct is bicistronic as shown in FIG. 1, where the construct has 2 promoters; for example, anti-SOD1 expression is driven by a H1 promoter and SOD1 cDNA expression is driven by a CBA promoter. The anti-SOD1-miR expression can also be driven by another Pol III promoter, such as U6 promoter, or a Pol II promoter to restrict expression of the miRNA to a specific cell or organ type. The second portion of the constructs typically has a Pol II promoter (e.g., CBA in FIG. 1) expressing the miRNA resistant SOD1 cDNA. This second promoter can also be the endogenous SOD1 promotor, or another promoter such as the synapsin promoter if restricted expression of the SOD1 cDNA to specific cell population is desired.

Figure 2:
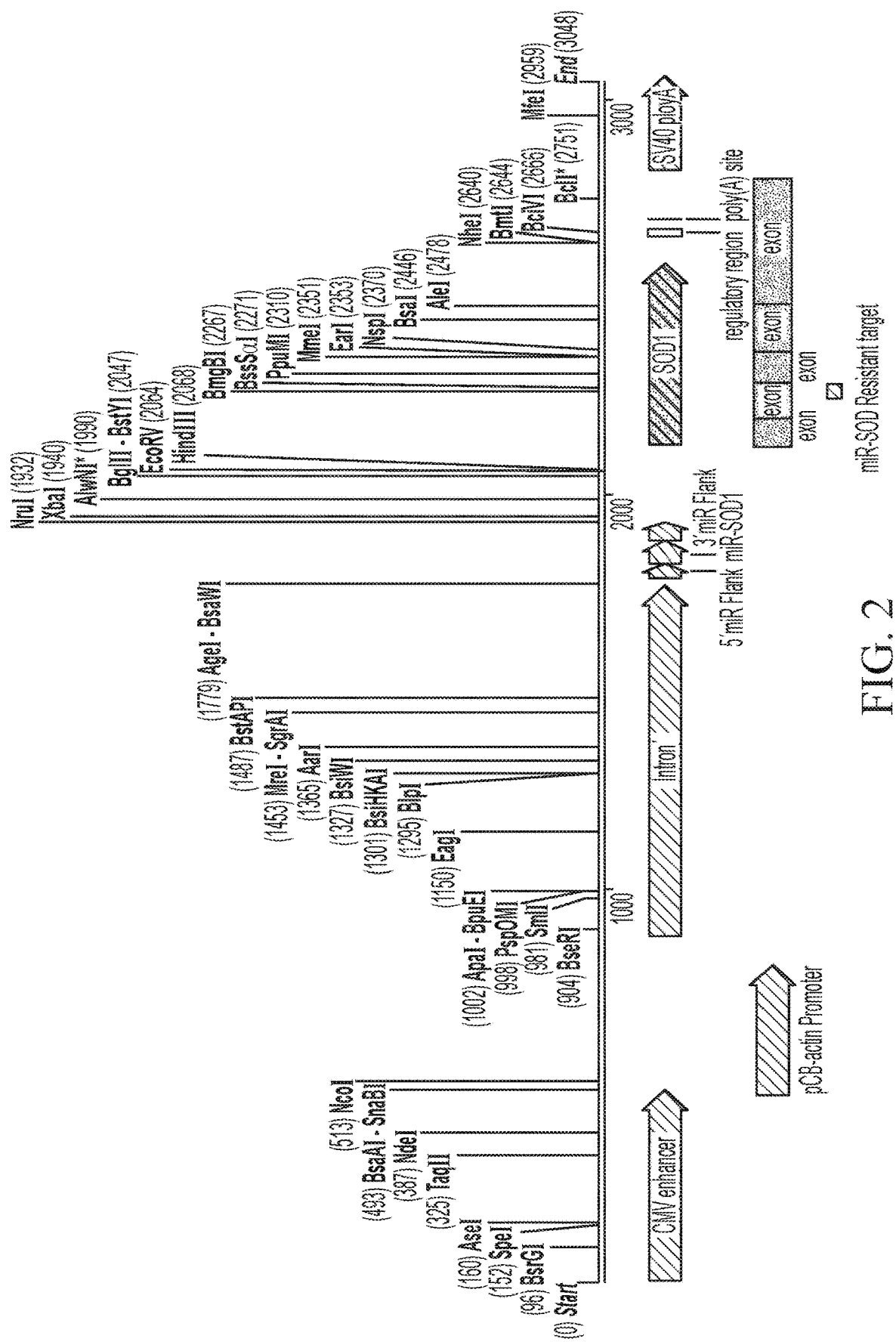
FIG. 2 shows a schematic overview of construct design for a single promoter dual function vector. The anti-Sod1 miRNA and miRNA-resistant SOD1 cDNA are both expressed by a chicken beta actin promoter and CMV enhancer (e.g., CAG promoter). The anti-Sod1 miR is located in an intron.
Figure 3:
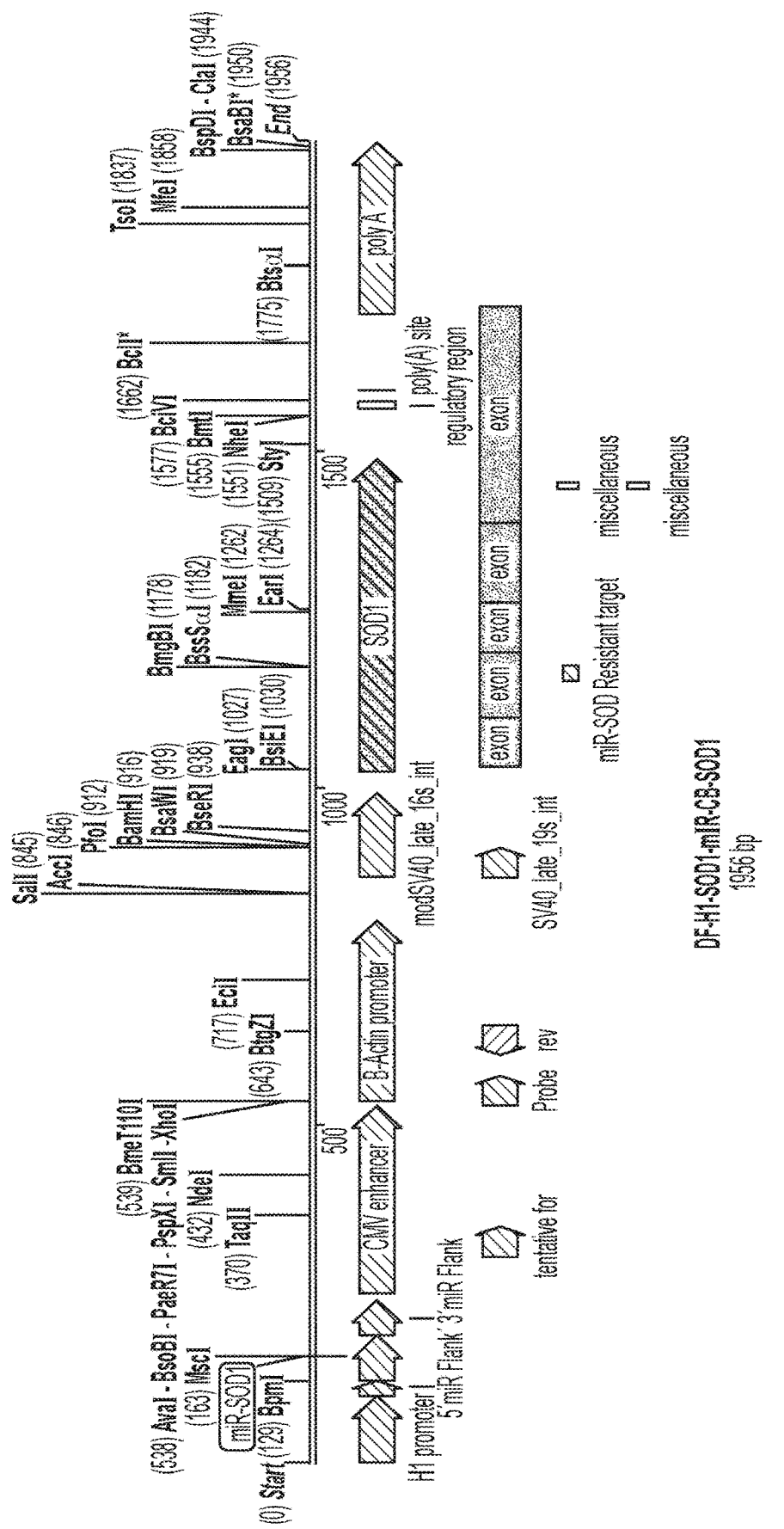
FIG. 3 shows a schematic overview of construct design for a bicistronic dual function vector. The anti-Sod1 miRNA is expressed by an H1 promoter and the miRNA-resistant SOD1 cDNA is expressed by a chicken beta actin promoter and CMV enhancer (e.g., CAG promoter). The locus of the SOD1 cDNA containing a silent mutation relative to wild-type SOD1 is shown ("miR-SOD Resistant Target").

In some embodiments, the dual function vector is a single pol II promoter (e.g., CBA) expressing both the artificial miR and the miR-resistant cDNA, as shown in FIG. 2. In this embodiment, the anti-SOD1-miR can be expressed from an intron within the SOD1 cDNA expression cassette, or alternatively as part of the 3'UTR (or 5' UTR) of the miR-resistant SOD1 cDNA expression cassette. Additional non-limiting examples of dual function vector constructs are shown in FIGS. 3-8 and described in SEQ ID NOs: 8-15. FIG. 9 shows a nucleic acid sequence alignment of wild-type SOD1 coding sequence (SEQ ID NO: 1) with an example of a "hardened" SOD1 coding sequence (SEQ ID NO: 7).

```
SEQUENCES
>Human SOD1 coding sequence (NCBI Ref. NM_000454.4)
                                                   (SEQ ID NO: 1)
ATGGCGACGAAGGCCGTGTGCGTGCTGAAGGGCGACGGCCCAGTGCAGGGCATC

ATCAATTTCGAGCAGAAGGAAAGTAATGGACCAGTGAAGGTGTGGGGAAGCATT

AAAGGACTGACTGAAGGCCTGCATGGATTCCATGTTCATGAGTTTGGAGATAATA

CAGCAGGCTGTACCAGTGCAGGTCCTCACTTTAATCCTCTATCCAGAAAACACGG

TGGGCCAAAGGATGAAGAGAGGCATGTTGGAGACTTGGGCAATGTGACTGCTGA

CAAAGATGGTGTGGCCGATGTGTCTATTGAAGATTCTGTGATCTCACTCTCAGGA

GACCATTGCATCATTGGCCGCACACTGGTGGTCCATGAAAAAGCAGATGACTTG

GGCAAAGGTGGAAATGAAGAAAGTACAAAGACAGGAAACGCTGGAAGTCGTTT

GGCTTGTGGTGTAATTGGGATCGCCCAATAA

>SOD1 miR target sequence 5'-3'; note in some embodiments,
"T" is replaced with "U"
                                                   (SEQ ID NO: 2)
CTGCATGGATTCCATGTTCAT >SOD1 miR mature miRNA 3'-5'; note in some embodiments,
"T" is replaced with "U"
                                                   (SEQ ID NO: 3)
GACGTACCTAAGGTACAAGTA >SOD-miR-127 mature miRNA 5'-3'; note in some embodiments,
"T" is replaced with "U"
                                                   (SEQ ID NO: 4)
CTGCATGGATTCCATGTTCAT >miR-SOD1 5'-3' strand; note in some embodiments,
"T" is replaced with "U"
                                                   (SEQ ID NO: 5)
TGCTGATGAACATGGAATCCATGCAGGTTTTGGCCACTGACTGACCTGCATGGTC

CATGTTCAT

>miR-SOD1 3'-5' strand; note in some embodiments,
"T" is replaced with "U"
                                                   (SEQ ID NO: 6)
ATGAACATGGACCATGCAGGTCAGTCAGTGGCCAAAACCTGCATGGATTCCATG

TTCATCAGCA
```

>Hardened SOD1 coding sequence;
silent base pair mutations relative to
wild-type SOD1 coding sequence in bold (SEQ ID NO: 7)
ATGGCGACGAAGGCCGTGTGCGTGCTGAAGGGCGACGGCCCAGTGCAGGGCATC

ATCAATTTCGAGCAGAAGGAAAGTAATGGACCAGTGAAGGTGTGGGGAAGCATT

AAAGGACTGACTGAAGGCCTGCACGGCTTTCACGTCCACGAGTTTGGAGATAAT

ACAGCAGGCTGTACCAGTGCAGGTCCTCACTTTAATCCTCTATCCAGAAAACACG

GTGGGCCAAAGGATGAAGAGAGGCATGTTGGAGACTTGGGCAATGTGACTGCTG

ACAAAGATGGTGTGGCCGATGTGTCTATTGAAGATTCTGTGATCTCACTCTCAGG

AGACCATTGCATCATTGGCCGCACACTGGTGGTCCATGAAAAAGCAGATGACTT

GGGCAAAGGTGGAAATGAAGAAAGTACAAAGACAGGAAACGCTGGAAGTCGTT

TGGCTTGTGGTGTAATTGGGATCGCCCAATAA

>Sequence for Bicistronic H1-miR and CB-Sod1
(SEQ ID NO: 8)
CTCTGGTCGTTACATAACTTACGGTAAATGGCCCGCCTGGCTGACCGCCCAACGA

CCCCCGCCCATTGACGTCAATAATGACGTATGTTCCCATAGTAACGCCAATAGGG

ACTTTCCATTGACGTCAATGGGTGGAGTATTTACGGTAAACTGCCCACTTGGCAG

TACATCAAGTGTATCATATGCCAAGTACGCCCCCTATTGACGTCAATGACGGTAA

ATGGCCCGCCTGGCATTATGCCCAGTACATGACCTTATGGGACTTTCCTACTTGG

CAGTACATCTACTCGAGGCCACGTTCTGCTTCACTCTCCCCATCTCCCCCCCCTCC

CCACCCCCAATTTTGTATTTATTTATTTTTTAATTATTTTGTGCAGCGATGGGGGC

GGGGGGGGGGGGGGCGCGCGCCAGGCGGGGCGGGGCGGGGCGAGGGGCGG

GGCGGGGCGAGGCGGAGAGGTGCGGCGGCAGCCAATCAGAGCGGCGCGCTCCG

AAAGTTTCCTTTTATGGCGAGGCGGCGGCGGCGGCGGCCCTATAAAAAGCGAAG

CGCGCGGCGGGCGGGAGCGGGATCAGCCACCGCGGTGGCGGCCTAGAGTCGAC

GAGGAACTGAAAAACCAGAAAGTTAACTGGTAAGTTTAGTCTTTTTGTCTTTTAT

TTCAGGTCCCGGATCCGGTGGTGGTGCAAATCAAAGAACTGCTCCTCAGTGGATG

TTGCCTTTACTTCTAGGCCTGTACGGAAGTGTTACTTCTGCTCTAAAAGCTGCGGA

ATTGTACCCGCGGCCGCGTTTAAACCCTGCAGGTCTAGAAAGCTTATCGATACCG

TCGACTAGAGCTCGCTGATCAGCCTCGACTGTGCCTTCTAGTTGCCAGCCATCTG

TTGTTTGCCCCTCCCCCGTGCCTTCCTTGACCCTGGAAGGTGCCACTCCCACTGTC

CTTTCCTAATAAAATGAGGAAATTGCATCGCATTGTCTGAGTAGGTGTCATTCTA

TTCTGGGGGGTGGGGTGGGGCAGGACAGCAAGGGGGAGGATTGGGAAGACAAT

AGCAGGGTACAAGTAAAGCGGCCCTAGCGTTTCCGGCGACGGTGCTAGACTCGA

GGACGGGGTGAACTACGCCTGAGGATCCGATCTTTTTCCCTCTGCCAAAAATTAT

GGGGACATCATGAAGCCCCTTGAGCATCTGACTTCTGGCTAATAAAGGAAATTTA

TTTTCATTGCAATAGTGTGTTGGAATTTTTTGTGTCTCTCACTCGGAAGCAATTCG

TTGATCTGAATTTCGACCACCCATAATACCCATTACCCTGGTAGATAAGTAGCAT

GGCGGGTTAATCATTAACTACAAGGAACCCCTAGTGATGGAGTTGGCCACTCCCT

CTCTGCGCGCTCGCTCGCTCACTGAGGCCGGGCGACCAAAGGTCGCCCGACGCC

CGGGCTTTGCCCGGCGGCCTCAGTGAGCGAGCGAGCGCGCAGCCTTAATTAAC

CTAATTCACTGGCCGTCGTTTTACAACGTCGTGACTGGGAAAACCCTGGCGTTAC

-continued

```
CCAACTTAATCGCCTTGCAGCACATCCCCCTTTCGCCAGCTGGCGTAATAGCGAA

GAGGCCCGCACCGATCGCCCTTCCCAACAGTTGCGCAGCCTGAATGGCGAATGG

GACGCGCCCTGTAGCGGCGCATTAAGCGCGGCGGGTGTGGTGGTTACGCGCAGC

GTGACCGCTACACTTGCCAGCGCCCTAGCGCCCGCTCCTTTCGCTTTCTTCCCTTC

CTTTCTCGCCACGTTCGCCGGCTTTCCCCGTCAAGCTCTAAATCGGGGGCTCCCTT

TAGGGTTCCGATTTAGTGCTTTACGGCACCTCGACCCCAAAAAACTTGATTAGGG

TGATGGTTCACGTAGTGGGCCATCGCCCTGATAGACGGTTTTTCGCCCTTTGACG

TTGGAGTCCACGTTCTTTAATAGTGGACTCTTGTTCCAAACTGGAACAACACTCA

ACCCTATCTCGGTCTATTCTTTTGATTTATAAGGGATTTTGCCGATTTCGGCCTAT

TGGTTAAAAAATGAGCTGATTTAACAAAAATTTAACGCGAATTTTAACAAAATAT

TAACGCTTACAATTTAGGTGGCACTTTTCGGGGAAATGTGCGCGGAACCCCTATT

TGTTTATTTTTCTAAATACATTCAAATATGTATCCGCTCATGAGACAATAACCCTG

ATAAATGCTTCAATAATATTGAAAAAGGAAGAGTATGAGTATTCAACATTTCCGT

GTCGCCCTTATTCCCTTTTTTGCGGCATTTTGCCTTCCTGTTTTTGCTCACCCAGAA

ACGCTGGTGAAAGTAAAAGATGCTGAAGATCAGTTGGGTGCACGAGTGGGTTAC

ATCGAACTGGATCTCAACAGCGGTAAGATCCTTGAGAGTTTTCGCCCCGAAGAAC

GTTTTCCAATGATGAGCACTTTTAAAGTTCTGCTATGTGGCGCGGTATTATCCCGT

ATTGACGCCGGGCAAGAGCAACTCGGTCGCCGCATACACTATTCTCAGAATGACT

TGGTTGAGTACTCACCAGTCACAGAAAAGCATCTTACGGATGGCATGACAGTAA

GAGAATTATGCAGTGCTGCCATAACCATGAGTGATAACACTGCGGCCAACTTACT

TCTGACAACGATCGGAGGACCGAAGGAGCTAACCGCTTTTTTGCACAACATGGG

GGATCATGTAACTCGCCTTGATCGTTGGGAACCGGAGCTGAATGAAGCCATACC

AAACGACGAGCGTGACACCACGATGCCTGTAGCAATGGCAACAACGTTGCGCAA

ACTATTAACTGGCGAACTACTTACTCTAGCTTCCCGGCAACAATTAATAGACTGG

ATGGAGGCGGATAAAGTTGCAGGACCACTTCTGCGCTCGGCCCTTCCGGCTGGCT

GGTTTATTGCTGATAAATCTGGAGCCGGTGAGCGTGGGTCTCGCGGTATCATTGC

AGCACTGGGGCCAGATGGTAAGCCCTCCCGTATCGTAGTTATCTACACGACGGG

GAGTCAGGCAACTATGGATGAACGAAATAGACAGATCGCTGAGATAGGTGCCTC

ACTGATTAAGCATTGGTAACTGTCAGACCAAGTTTACTCATATATACTTTAGATT

GATTTAAAACTTCATTTTTAATTTAAAAGGATCTAGGTGAAGATCCTTTTTGATAA

TCTCATGACCAAAATCCCTTAACGTGAGTTTTCGTTCCACTGAGCGTCAGACCCC

GTAGAAAAGATCAAAGGATCTTCTTGAGATCCTTTTTTTCTGCGCGTAATCTGCT

GCTTGCAAACAAAAAAACCACCGCTACCAGCGGTGGTTTGTTTGCCGGATCAAG

AGCTACCAACTCTTTTTCCGAAGGTAACTGGCTTCAGCAGAGCGCAGATACCAAA

TACTGTTCTTCTAGTGTAGCCGTAGTTAGGCCACCACTTCAAGAACTCTGTAGCA

CCGCCTACATACCTCGCTCTGCTAATCCTGTTACCAGTGGCTGCTGCCAGTGGCG

ATAAGTCGTGTCTTACCGGGTTGGACTCAAGACGATAGTTACCGGATAAGGCGC

AGCGGTCGGGCTGAACGGGGGGTTCGTGCACACAGCCCAGCTTGGAGCGAACGA

CCTACACCGAACTGAGATACCTACAGCGTGAGCTATGAGAAAGCGCCACGCTTC

CCGAAGGGAGAAAGGCGGACAGGTATCCGGTAAGCGGCAGGGTCGGAACAGGA

GAGCGCACGAGGGAGCTTCCAGGGGGAAACGCCTGGTATCTTTATAGTCCTGTC
```

-continued

```
GGGTTTCGCCACCTCTGACTTGAGCGTCGATTTTTGTGATGCTCGTCAGGGGGGC

GGAGCCTATGGAAAAACGCCAGCAACGCGGCCTTTTTACGGTTCCTGGCCTTTTG

CTGGCCTTTTGCTCACATGTTCTTTCCTGCGTTATCCCCTGATTCTGTGGATAACC

GTATTACCGCCTTTGAGTGAGCTGATACCGCTCGCCGCAGCCGAACGACCGAGC

GCAGCGAGTCAGTGAGCGAGGAAGCGGAAGAGCGCCCAATACGCAAACCGCCT

CTCCCCGCGCGTTGGCCGATTCATTAATGCAGCTGATTCTAACGAGGAAAGCACG

TTATACGTGCTCGTCAAAGCAACCATAGTACGCGCCCTGTAGCGGCGCATTAAGC

GCGGCGGGTGTGGTGGTTACGCGCAGCGTGACCGCTACACTTGCCAGCGCCCTA

GCGCCCGCTCCTTTCGCTTTCTTCCCTTCCTTTCTCGCCACGTTCGCCGGCTTTCCC

CGTCAAGCTCTAAATCGGGGGCTCCCTTTAGGGTTCCGATTTAGTGCTTTACGGC

ACCTCGACCCCAAAAAACTTGATTAGGGTGATGGTTCACGTAGTGGGCCATCGCC

CTGATAGACGGTTTTTCGCCCTTTGACGTTGGAGTCCACGTTCTTTAATAGTGGAC

TCTTGTTCCAAACTGGAACAACACTCAACCCTATCTCGGTCTATTCTTTTGATTTA

TAAGGGATTTTGCCGATTTCGGCCTATTGGTTAAAAAATGAGCTGATTTAACAAA

AATTTAACGCGAATTTTAACAAAATATTAACGCTTACAATTTAAATATTTGCTTAT

ACAATCTTCCTGTTTTTGGGGCTTTTCTGATTATCAACCGGGGTACATATGATTGA

CATGCTAGTTTTACGATTACCGTTCATCGCCCTGCGCGCTCGCTCGCTCACTGAGG

CCGCCCGGGCAAAGCCCGGGCGTCGGGCGACCTTTGGTCGCCCGGCCTCAGTGA

GCGAGCGAGCGCGCAGAGAGGGAGTGGAATTCTAAATTCATATTTGCATGTCGC

TATGTGTTCTGGGAAATCACCATAAACGTGAAATGTCTTTGGATTTGGGAATCTT

ATAAGTTCTGTATGAGACCACTCGCCTGGAGGCTTGCTGAAGGCTGTATGCTGAT

GAACATGGAATCCATGCAGGTTTTGGCCACTGACTGACCTGCATGGTCCATGTTC

ATCAGGACACAAGGCCTGTTACTAGCACTCACATGGAACAAATGGCCCTTTTTTC

TAGTGGTAC

>Sequence for CB-anti-Sod1 miR and miRNA resistant Sod1
                                              (SEQ ID NO: 9)
TCAATATTGGCCATTAGCCATATTATTCATTGGTTATATAGCATAAATCAATATTG

GCTATTGGCCATTGCATACGTTGTATCTATATCATAATATGTACATTTATATTGGC

TCATGTCCAATATGACCGCCATGTTGGCATTGATTATTGACTAGTTATTAATAGTA

ATCAATTACGGGGTCATTAGTTCATAGCCCATATATGGAGTTCCGCGTTACATAA

CTTACGGTAAATGGCCCGCCTGGCTGACCGCCCAACGACCCCCGCCCATTGACGT

CAATAATGACGTATGTTCCCATAGTAACGCCAATAGGGACTTTCCATTGACGTCA

ATGGGTGGAGTATTTACGGTAAACTGCCCACTTGGCAGTACATCAAGTGTATCAT

ATGCCAAGTCCGCCCCCTATTGACGTCAATGACGGTAAATGGCCCGCCTGGCATT

ATGCCCAGTACATGACCTTACGGGACTTTCCTACTTGGCAGTACATCTACGTATT

AGTCATCGCTATTACCATGGTCGAGGTGAGCCCCACGTTCTGCTTCACTCTCCCC

ATCTCCCCCCCCTCCCCACCCCCAATTTTGTATTTATTTATTTTTAATTATTTTGT

GCAGCGATGGGGGCGGGGGGGGGGGGGGCGCGCGCCAGGCGGGGCGGGGCG

GGGCGAGGGGCGGGGCGGGGCGAGGCGGAGAGGTGCGGCGGCAGCCAATCAGA

GCGGCGCGCTCCGAAAGTTTCCTTTTATGGCGAGGCGGCGGCGGCGGCGGCCCT

ATAAAAAGCGAAGCGCGCGGCGGGCGGGAGTCGCTGCGACGCTGCCTTCGCCCC
```

```
GTGCCCCGCTCCGCCGCCGCCTCGCGCCGCCCGCCCCGGCTCTGACTGACCGCGT

TACTCCCACAGGTGAGCGGGCGGGACGGCCCTTCTCCTCCGGGCTGTAATTAGCG

CTTGGTTTAATGACGGCTTGTTTCTTTTCTGTGGCTGCGTGAAAGCCTTGAGGGGC

TCCGGGAGGGCCCTTTGTGCGGGGGGGAGCGGCTCGGGGGGTGCGTGCGTGTGT

GTGTGCGTGGGGAGCGCCGCGTGCGGCCCGCGCTGCCCGGCGGCTGTGAGCGCT

GCGGGCGCGGCGCGGGCTTTGTGCGCTCCGCAGTGTGCGCGAGGGGAGCGCGG

CCGGGGGCGGTGCCCCGCGGTGCGGGGGGGCTGCGAGGGGAACAAAGGCTGC

GTGCGGGGTGTGTGCGTGGGGGGGTGAGCAGGGGGTGTGGGCGCGGCGGTCGGG

CTGTAACCCCCCCCTGCACCCCCCTCCCCGAGTTGCTGAGCACGGCCCGGCTTCG

GGTGCGGGGCTCCGTACGGGGCGTGGCGCGGGGCTCGCCGTGCCGGGCGGGGGG

TGGCGGCAGGTGGGGGTGCCGGGCGGGGCGGGGCCGCCTCGGGCCGGGGAGGG

CTCGGGGGAGGGGCGCGGCGGCCCCCGGAGCGCCGGCGGCTGTCGAGGCGCGG

CGAGCCGCAGCCATTGCCTTTTATGGTAATCGTGCGAGAGGGCGCAGGGACTTCC

TTTGTCCCAAATCTGTGCGGAGCCGAAATCTGGGAGGCGCCGCCGCACCCCCTCT

AGCGGGCGCGGGGCGAAGCGGTGCGGCGCCGGCAGGAAGGAAATGGGCGGGGA

GGGCCTTCGTGCGTCGCCGCGCCGCCGTCCCCTTCTCCCTCTCCAGCCTCGGGGC

TGTCCGCGGGGGGACGGCTGCCTTCGGGGGGGACGGGGCAGGGCGGGGTTCGGC

TTCTGGCGTGTGACCGGCGGCTCTAGCCGGCGACCGGTATGCATCCTGGAGGCTT

GCTGAAGGCTGTATGCTGATGAACATGGAATCCATGCAGGTTTTGGCCACTGACT

GACCTGCATGGTCCATGTTCATCAGGACACAAGGCCTGTTACTAGCACTCACATG

GAACAAATGGCCCCTAGCTCGCGATGCATCTAGAGCCTCTGCTAACCATGTTCAT

GCCTTCTTCTTTTTCCTACAGCTCCTGGGCAACGTGCTGGTTATTGTGCTGTCTCA

TCATTTTGGCAAAGAATTCCTCGAAGATCTAGGGAATTCGATATCAAGCTTGGGG

ATTTTCAGGCACCACCACTGACCTGGGACAGTGTTAACGACACGATCCAATGGCG

ACGAAGGCCGTGTGCGTGCTGAAGGGCGACGGCCCAGTGCAGGGCATCATCAAT

TTCGAGCAGAAGGAAAGTAATGGACCAGTGAAGGTGTGGGGAAGCATTAAAGG

ACTGACTGAAGGCCTGCACGGCTTTCACGTCCACGAGTTTGGAGATAATACAG

CAGGCTGTACCAGTGCAGGTCCTCACTTTAATCCTCTATCCAGAAAACACGGTGG

GCCAAAGGATGAAGAGAGGCATGTTGGAGACTTGGGCAATGTGACTGCTGACAA

AGATGGTGTGGCCGATGTGTCTATTGAAGATTCTGTGATCTCACTCTCAGGAGAC

CATTGCATCATTGGCCGCACACTGGTGGTCCATGAAAAAGCAGATGACTTGGGC

AAAGGTGGAAATGAAGAAAGTACAAAGACAGGAAACGCTGGAAGTCGTTTGGC

TTGTGGTGTAATTGGGATCGCCCAATAAACATTCCCTTGGATGTAGTCTGAGGCC

CCTTAACTCATCTGTTATCCTGCTAGCTGTAGAAATGTATCCTGATAAACATTAA

ACACTGTAATCTTAAAAGTGTAATTGTGTGACTTTTTCAGAGTTGCTTTAAAGTAC

CTGTAGTGAGAAACTGATTTATGATCACTTGGAAGATTTGTATAGTTTTATAAAA

CTCAGTTAAAATGTCTGTTTCAAGGCCGCTTCGAGCAGACATGATAAGATACATT

GATGAGTTTGGACAAACCACAACTAGAATGCAGTGAAAAAAATGCTTTATTTGT

GAAATTTGTGATGCTATTGCTTTATTTGTAACCATTATAAGCTGCAATAAACAAG

TTAACAACAACAATTGCATTCATTTTATGTTTCAGGTTCAGGGGAGATGTGGGA

GGTTTTTTAAAGCAAGTAAAACCTCTACAAATGTGGTAAAATCGA
```

-continued

>Sequence for bicistronic H1-SOD1-miR-CB-SOD1;
miR Resistant SOD1 target is in bold;
SOD1 coding sequence in lowercase (SEQ ID NO: 10)

AATTCTAAATTCATATTTGCATGTCGCTATGTGTTCTGGGAAATCACCATAAACG

TGAAATGTCTTTGGATTTGGGAATCTTATAAGTTCTGTATGAGACCACTCGCCTG

GAGGCTTGCTGAAGGCTGTATGCTGATGAACATGGAATCCATGCAGGTTTTGGCC

ACTGACTGACCTGCATGGTCCATGTTCATCAGGACACAAGGCCTGTTACTAGCAC

TCACATGGAACAAATGGCCCTTTTTTCTAGTGGTACGTCGTTACATAACTTACGG

TAAATGGCCCGCCTGGCTGACCGCCCAACGACCCCCGCCCATTGACGTCAATAAT

GACGTATGTTCCCATAGTAACGCCAATAGGGACTTTCCATTGACGTCAATGGGTG

GAGTATTTACGGTAAACTGCCCACTTGGCAGTACATCAAGTGTATCATATGCCAA

GTACGCCCCCTATTGACGTCAATGACGGTAAATGGCCCGCCTGGCATTATGCCCA

GTACATGACCTTATGGGACTTTCCTACTTGGCAGTACATCTACTCGAGGCCACGT

TCTGCTTCACTCTCCCCATCTCCCCCCCCTCCCCACCCCCAATTTTGTATTTATTTA

TTTTTTAATTATTTTGTGCAGCGATGGGGGCGGGGGGGGGGGGGGCGCGCGC

CAGGCGGGGCGGGGCGGGGCGAGGGGCGGGGCGGGGCGAGGCGGAGAGGTGCG

GCGGCAGCCAATCAGAGCGGCGCGCTCCGAAAGTTTCCTTTTATGGCGAGGCGG

CGGCGGCGGCGGCCCTATAAAAAGCGAAGCGCGCGGCGGGCGGGAGCGGGATC

AGCCACCGCGGTGGCGGCCTAGAGTCGACGAGGAACTGAAAAACCAGAAAGTTA

ACTGGTAAGTTTAGTCTTTTTGTCTTTTATTTCAGGTCCCGGATCCGGTGGTGGTG

CAAATCAAAGAACTGCTCCTCAGTGGATGTTGCCTTTACTTCTAGGCCTGTACGG

AAGTGTTACTTCTGCTCTAAAAGCTGCGGAATTGTACCCGCGGCCGATCCAatggcg acgaaggccgtgtgcgtgctgaagggcgacggcccagtgcagggcatcatcaatt tcgagcagaaggaaagtaatggaccagtgaaggtgtggggaagcattaaaggactg actgaaggcctgcacggctttcacgtccacgagtttggagataatacagcaggct gtaccagtgcaggtcctcactttaatcctctatccagaaaacacggtgggccaaa ggatgaagagaggcatgttggagacttgggcaatgtgactgctgacaaagatggtg tggccgatgtgtctattgaagattctgtgatctcactctcaggagaccattgcat cattggccgcacactggtggtccatgaaaaagcagatgacttgggcaaaggtggaa atgaagaaagtacaaagacaggaaacgctggaagtcgtttggcttgtggtgtaatt gggatcgcccaataaacattcccttggatgtagtctgaggccccttaactcatct gttatcctgctagctgtagaaatgtatcctgataaacattaaacactgtaatctta aaagtgtaattgtgtgacttttcagagttgctttaaagtacctgtagtgagaaac tgatttatgatcacttggaagatttgtatagttttataaaactcagttaaaa tgtctgtttcaaCAGACATGATAAGATACATTGATGAGT

TTGGACAAACCACAACTAGAATGCAGTGAAAAAAATGCTTTATTTGTGAAATTTG

TGATGCTATTGCTTTATTTGTAACCATTATAAGCTGCAATAAACAAGTTAACAAC

AACAATTGCATTCATTTTATGTTTCAGGTTCAGGGGAGATGTGGGAGGTTTTTT

AAAGCAAGTAAAACCTCTACAAATGTGGTAAAATCGATAAGGATCT

>Sequence for CB-miR-CB-SOD1;
miR Resistant SOD1 target is in bold;
SOD1 coding sequence in lowercase (SEQ ID NO: 11)

TCAATATTGGCCATTAGCCATATTATTCATTGGTTATATAGCATAAATCAATATTG

GCTATTGGCCATTGCATACGTTGTATCTATATCATAATATGTACATTTATATTGGC

TCATGTCCAATATGACCGCCATGTTGGCATTGATTATTGACTAGTTATTAATAGTA

ATCAATTACGGGGTCATTAGTTCATAGCCCATATATGGAGTTCCGCGTTACATAA

CTTACGGTAAATGGCCCGCCTGGCTGACCGCCCAACGACCCCCGCCCATTGACGT

CAATAATGACGTATGTTCCCATAGTAACGCCAATAGGGACTTTCCATTGACGTCA

ATGGGTGGAGTATTTACGGTAAACTGCCCACTTGGCAGTACATCAAGTGTATCAT

ATGCCAAGTCCGCCCCCTATTGACGTCAATGACGGTAAATGGCCCGCCTGGCATT

ATGCCCAGTACATGACCTTACGGGACTTTCCTACTTGGCAGTACATCTACGTATT

AGTCATCGCTATTACCATGGTCGAGGTGAGCCCCACGTTCTGCTTCACTCTCCCC

ATCTCCCCCCCCTCCCCACCCCCAATTTTGTATTTATTTATTTTTAATTATTTTGT

GCAGCGATGGGGCGGGGGGGGGGGGGGCGCGCGCCAGGCGGGGCGGGGCG

GGGCGAGGGGCGGGGCGGGGCGAGGCGGAGAGGTGCGGCGGCAGCCAATCAGA

GCGGCGCGCTCCGAAAGTTTCCTTTTATGGCGAGGCGGCGGCGGCGGCGGCCCT

ATAAAAAGCGAAGCGCGCGGCGGGCGGGAGTCGCTGCGACGCTGCCTTCGCCCC

GTGCCCCGCTCCGCCGCCGCCTCGCGCCGCCCGCCCCGGCTCTGACTGACCGCGT

TACTCCCACAGGTGAGCGGGCGGGACGGCCCTTCTCCTCCGGGCTGTAATTAGCG

CTTGGTTTAATGACGGCTTGTTTCTTTTCTGTGGCTGCGTGAAAGCCTTGAGGGGC

TCCGGGAGGGCCCTTTGTGCGGGGGGGAGCGGCTCGGGGGGTGCGTGCGTGTGT

GTGTGCGTGGGGAGCGCCGCGTGCGGCCCGCGCTGCCCGGCGGCTGTGAGCGCT

GCGGGCGCGGCGCGGGGCTTTGTGCGCTCCGCAGTGTGCGCGAGGGGAGCGCGG

CCGGGGGCGGTGCCCCGCGGTGCGGGGGGGGCTGCGAGGGGAACAAAGGCTGC

GTGCGGGGTGTGTGCGTGGGGGGGTGAGCAGGGGGTGTGGGCGCGGCGGTCGGG

CTGTAACCCCCCCCTGCACCCCCCTCCCCGAGTTGCTGAGCACGGCCCGGCTTCG

GGTGCGGGGCTCCGTACGGGGCGTGGCGCGGGGCTCGCCGTGCCGGGCGGGGGG

TGGCGGCAGGTGGGGGTGCCGGGCGGGGCGGGGCCGCCTCGGGCCGGGGAGGG

CTCGGGGGAGGGGCGCGGCGGCCCCCGGAGCGCCGGCGGCTGTCGAGGCGCGG

CGAGCCGCAGCCATTGCCTTTTATGGTAATCGTGCGAGAGGGCGCAGGGACTTCC

TTTGTCCCAAATCTGTGCGGAGCCGAAATCTGGGAGGCGCCGCCGCACCCCCTCT

AGCGGGCGCGGGGCGAAGCGGTGCGGCGCCGGCAGGAAGGAAATGGGCGGGGA

GGGCCTTCGTGCGTCGCCGCGCCGCCGTCCCCTTCTCCCTCTCCAGCCTCGGGGC

TGTCCGCGGGGGGACGGCTGCCTTCGGGGGGGACGGGGCAGGGCGGGGTTCGGC

TTCTGGCGTGTGACCGGCGGCTCTAGCCGGCGACCGGTATGCATCCTGGAGGCTT

GCTGAAGGCTGTATGCTGATGAACATGGAATCCATGCAGGTTTTGGCCACTGACT

GACCTGCATGGTCCATGTTCATCAGGACACAAGGCCTGTTACTAGCACTCACATG

GAACAAATGGCCCCTAGCTCGCGATGCATCTAGAGCCTCTGCTAACCATGTTCAT

GCCTTCTTCTTTTTCCTACAGCTCCTGGGCAACGTGCTGGTTATTGTGCTGTCTCA

TCATTTTGGCAAAGAATTCCTCGAAGATCTAGGGAATTCGATATCAAGCTTGGGG

-continued

```
ATTTTCAGGCACCACCACTGACCTGGGACAGTGTTAACGACACGATCCAatggcgacg aaggccgtgtgcgtgctgaagggcgacggcccagtgcagggcatcatcaattt cgagcagaaggaaagtaatggaccagtgaaggtgtgggaagcattaaaggact gactgaaggcctgcacggctttcacgtccacgagtttggagataatacagcaggc tgtaccagtgcaggtcctcactttaatcctctatccagaaaacacggtgggcc aaaggatgaagagaggcatgttggagacttgggcaatgtgactgctgacaaag atggtgtggccgatgtgtctattgaagattctgtgatctcactctcaggagacc attgcatcattggccgcacactggtggtccatgaaaaagcagatgacttgggc aaaggtggaaatgaagaaagtacaaagacaggaaacgctggaagtcgtttggct tgtggtgtaattgggatcgcccaataaacattcccttggatgtagtctgaggccc cttaactcatctgttatcctgctagctgtagaaatgtatcctgataaacatta aacactgtaatcttaaaagtgtaattgtgtgactttttcagagttgctttaaag tacctgtagtgagaaactgatttatgatcacttggaagatttgtatagtttat aaaactcagttaaaatgtctgtttcaaGGCCGCTTCGAGCAGACATGATAAGATAC

ATTGATGAGTTTGGACAAACCACAACTAGAATGCAGTGAAAAAAATGCTTTATTT

GTGAAATTTGTGATGCTATTGCTTTATTTGTAACCATTATAAGCTGCAATAAACA

AGTTAACAACAACAATTGCATTCATTTTATGTTTCAGGTCAGGGGAGATGTGG

GAGGTTTTTTAAAGCAAGTAAAACCTCTACAAATGTGGTAAAATCGA

>Sequence for self-complementary H1-SOD1-miR-CB-SOD1
(w/ 3' UTR); AAV ITRs in bold
                                        (SEQ ID NO: 12)
CCCTGCGCGCTCGCTCGCTCACTGAGGCCGCCCGGGCAAAGCCCGGGCGTC

GGGCGACCTTTGGTCGCCCGGCCTCAGTGAGCGAGCGAGCGCGCAGAGAG

GGAGTGGAAATTCTAAATTCATATTTGCATGTCGCTATGTGTTCTGGGAAATCAC

CATAAACGTGAAATGTCTTTGGATTTGGGAATCTTATAAGTTCTGTATGAGACCA

CTCGCCTGGAGGCTTGCTGAAGGCTGTATGCTGATGAACATGGAATCCATGCAGG

TTTTGGCCACTGACTGACCTGCATGGTCCATGTTCATCAGGACACAAGGCCTGTT

ACTAGCACTCACATGGAACAAATGGCCCTTTTTTCTAGTGGTACGTCGTTACATA

ACTTACGGTAAATGGCCCGCCTGGCTGACCGCCCAACGACCCCCGCCCATTGACG

TCAATAATGACGTATGTTCCCATAGTAACGCCAATAGGGACTTTCCATTGACGTC

AATGGGTGGAGTATTTACGGTAAACTGCCCACTTGGCAGTACATCAAGTGTATCA

TATGCCAAGTACGCCCCCTATTGACGTCAATGACGGTAAATGGCCCGCCTGGCAT

TATGCCCAGTACATGACCTTATGGGACTTTCCTACTTGGCAGTACATCTACTCGA

GGCCACGTTCTGCTTCACTCTCCCCATCTCCCCCCCCTCCCACCCCCAATTTTGT

ATTTATTTATTTTTAATTATTTTGTGCAGCGATGGGGGCGGGGGGGGGGGGGGG

GCGCGCGCCAGGCGGGGCGGGGCGGGGCGAGGGGCGGGGCGGGGCGAGGCGGA

GAGGTGCGGCGGCAGCCAATCAGAGCGGCGCGCTCCGAAAGTTTCCTTTTATGG

CGAGGCGGCGGCGGCGGCGGCCCTATAAAAAGCGAAGCGCGCGGCGGGCGGGA

GCGGGATCAGCCACCGCGGTGGCGGCCTAGAGTCGACGAGGAACTGAAAAACC

AGAAAGTTAACTGGTAAGTTTAGTCTTTTTGTCTTTTATTTCAGGTCCCGGATCCG

GTGGTGGTGCAAATCAAAGAACTGCTCCTCAGTGGATGTTGCCTTTACTTCTAGG

CCTGTACGGAAGTGTTACTTCTGCTCTAAAAGCTGCGGAATTGTACCCGCGGCCG
```

ATCCAatggcgacgaaggccgtgtgcgtgctgaagggcgacggcccagtgcag ggcatcatcaatttcgagcagaaggaaagtaatggaccagtgaaggtgtgggga agcattaaaggactgactgaaggcctgcacggctttcacgtccacgagtttgga gataatacagcaggctgtaccagtgcaggtcctcactttaatcctctatccaga aaacacggtgggccaaaggatgaagagaggcatgttggagacttgggcaatgtga ctgctgacaaagatggtgtggccgatgtgtctattgaagattctgtgatctc actctcaggagaccattgcatcattggccgcacactggtggtccatgaaaaagc agatgacttgggcaaaggtggaaatgaagaaagtacaaagacaggaaacgctgga agtcgtttggcttgtggtgtaattgggatcgcccaataaacattcccttggat gtagtctgaggcccttaactcatctgttatcctgctagctgtagaaatgtatc ctgataaacattaaacactgtaatcttaaaagtgtaattgtgtgacttttcag agttgctttaaagtacctgtagtgagaaactgatttatgatcacttggaagattt gtatagttttataaaactcagttaaaatgtctgtttcaaCAGACATGATAAGATACA

TTGATGAGTTTGGACAAACCACAACTAGAATGCAGTGAAAAAAATGCTTTATTTG

TGAAATTTGTGATGCTATTGCTTTATTTGTAACCATTATAAGCTGCAATAAACAA

GTTAACAACAACAATTGCATTCATTTTATGTTTCAGGTTCAGGGGAGATGTGGG

AGGTTTTTTAAAGCAAGTAAAACCTCTACAAATGTGGTAAAATCGATAAGAAGG

AACCCCTAGTGATGGAGTTGGCCACTCCCTCTCTGCGCGCTCGCTCGCTCAC

TGAGGCCGGGCGACCAAAGGTCGCCCGACGCCCGGGCTTTGCCCGGGCGG

CCTCAGTGAGCGAGCGAGCGCGCAGCCT

>Sequence for self-complementary H1-SOD1-miR-CB-SOD1
(w/o 3' UTR); AAV ITRs in bold (SEQ ID NO: 13)

CCCTGCGCGCTCGCTCGCTCACTGAGGCCGCCCGGGCAAAGCCCGGGCGTC

GGGCGACCTTTGGTCGCCCGGCCTCAGTGAGCGAGCGAGCGCGCAGAGAG

GGAGTGGAAATTCTAAATTCATATTTGCATGTCGCTATGTGTTCTGGGAAATCAC

CATAAACGTGAAATGTCTTTGGATTTGGGAATCTTATAAGTTCTGTATGAGACCA

CTCGCCTGGAGGCTTGCTGAAGGCTGTATGCTGATGAACATGGAATCCATGCAGG

TTTTGGCCACTGACTGACCTGCATGGTCCATGTTCATCAGGACACAAGGCCTGTT

ACTAGCACTCACATGGAACAAATGGCCCTTTTTTCTAGTGGTACGTCGTTACATA

ACTTACGGTAAATGGCCCGCCTGGCTGACCGCCCAACGACCCCCGCCCATTGACG

TCAATAATGACGTATGTTCCCATAGTAACGCCAATAGGGACTTTCCATTGACGTC

AATGGGTGGAGTATTTACGGTAAACTGCCCACTTGGCAGTACATCAAGTGTATCA

TATGCCAAGTACGCCCCCTATTGACGTCAATGACGGTAAATGGCCCGCCTGGCAT

TATGCCCAGTACATGACCTTATGGGACTTTCCTACTTGGCAGTACATCTACTCGA

GGCCACGTTCTGCTTCACTCTCCCCATCTCCCCCCCCTCCCACCCCCAATTTTGT

ATTTATTTATTTTTAATTATTTTGTGCAGCGATGGGGGCGGGGGGGGGGGGGGG

GCGCGCGCCAGGCGGGGCGGGGCGGGGCGAGGGGCGGGGCGGGGCGAGGCGGA

GAGGTGCGGCGGCAGCCAATCAGAGCGGCGCGCTCCGAAAGTTTCCTTTTATGG

CGAGGCGGCGGCGGCGGCGGCCCTATAAAAAGCGAAGCGCGCGGCGGGCGGGA

GCGGGATCAGCCACCGCGGTGGCGGCCTAGAGTCGACGAGGAACTGAAAAACC

AGAAAGTTAACTGGTAAGTTTAGTCTTTTTGTCTTTTATTTCAGGTCCCGGATCCG

-continued

```
GTGGTGGTGCAAATCAAAGAACTGCTCCTCAGTGGATGTTGCCTTTACTTCTAGG

CCTGTACGGAAGTGTTACTTCTGCTCTAAAAGCTGCGGAATTGTACCCGCGGCCG

ATCCAatggcgacgaaggccgtgtgcgtgctgaagggcgacggcccagtgcagg gcatcatcaatttcgagcagaaggaaagtaatggaccagtgaaggtgtggggaag cattaaaggactgactgaaggcctgcacggctttcacgtccacgagtttggaga taatacagcaggctgtaccagtgcaggtcctcactttaatcctctatccagaaaa cacggtgggccaaaggatgaagagaggcatgttggagacttgggcaatgtgact gctgacaaagatggtgtggccgatgtgtctattgaagattctgtgatctcactct caggagaccattgcatcattggccgcacactggtggtccatgaaaaagcagatg acttgggcaaaggtggaaatgaagaaagtacaaagacaggaaacgctggaagtcgtttg gcttgtggtgtaattgggatcgcccaataaaCAGACATGATAAGATACATTGATGAGT

TTGGACAAACCACAACTAGAATGCAGTGAAAAAAATGCTTTATTTGTGAAATTTGTGATG

CTATTGCTTTATTTGTAACCATTATAAGCTGCAATAAACAAGTTAACAACAACAA

TTGCATTCATTTTATGTTTCAGGTTCAGGGGGAGATGTGGGAGGTTTTTTAAAGC

AAGTAAAACCTCTACAAATGTGGTAAAATCGATAAGAAGGAACCCCTAGTGAT

GGAGTTGGCCACTCCCTCTCTGCGCGCTCGCTCGCTCACTGAGGCCGGGCG

ACCAAAGGTCGCCCGACGCCCGGGCTTTGCCCGGGCGGCCTCAGTGAGCGA

GCGAGCGCGCAGCCT
```

>Sequence for single stranded CB-miR-CB-SOD1 (w/ 3' UTR); AAV ITRs in bold (SEQ ID NO: 14)

```
GGGGGGGGGGGGGGGGGTTGGCCACTCCCTCTCTGCGCGCTCGCTCGCTCAC

TGAGGCCGGGCGACCAAAGGTCGCCCGACGCCCGGGCTTTGCCCGGGCGG

CCTCAGTGAGCGAGCGAGCGCGCAGAGAGGGAGTGGCCAACTCCATCACTA

GGGGTTCCTAGATCTCAATATTGGCCATTAGCCATATTATTCATTGGTTATATAG

CATAAATCAATATTGGCTATTGGCCATTGCATACGTTGTATCTATATCATAATATG

TACATTTATATTGGCTCATGTCCAATATGACCGCCATGTTGGCATTGATTATTGAC

TAGTTATTAATAGTAATCAATTACGGGGTCATTAGTTCATAGCCCATATATGGAG

TTCCGCGTTACATAACTTACGGTAAATGGCCCGCCTGGCTGACCGCCCAACGACC

CCCGCCCATTGACGTCAATAATGACGTATGTTCCCATAGTAACGCCAATAGGGAC

TTTCCATTGACGTCAATGGGTGGAGTATTTACGGTAAACTGCCCACTTGGCAGTA

CATCAAGTGTATCATATGCCAAGTCCGCCCCCTATTGACGTCAATGACGGTAAAT

GGCCCGCCTGGCATTATGCCCAGTACATGACCTTACGGGACTTTCCTACTTGGCA

GTACATCTACGTATTAGTCATCGCTATTACCATGGTCGAGGTGAGCCCCACGTTC

TGCTTCACTCTCCCCATCTCCCCCCCCTCCCCACCCCCAATTTTGTATTTATTTATT

TTTTAATTATTTTGTGCAGCGATGGGGGCGGGGGGGGGGGGGGCGCGCGCCA

GGCGGGGCGGGGCGGGGCGAGGGGCGGGGCGGGGCGAGGCGGAGAGGTGCGGC

GGCAGCCAATCAGAGCGGCGCGCTCCGAAAGTTTCCTTTTATGGCGAGGCGGCG

GCGGCGGCGGCCCTATAAAAAGCGAAGCGCGCGGCGGGCGGGAGTCGCTGCGA

CGCTGCCTTCGCCCCGTGCCCCGCTCCGCCGCCGCCTCGCGCCGCCCGCCCCGGC

TCTGACTGACCGCGTTACTCCCACAGGTGAGCGGGCGGGACGGCCCTTCTCCTCC

GGGCTGTAATTAGCGCTTGGTTTAATGACGGCTTGTTTCTTTTCTGTGGCTGCGTG
```

-continued

```
AAAGCCTTGAGGGGCTCCGGGAGGGCCCTTTGTGCGGGGGGGAGCGGCTCGGGG

GGTGCGTGCGTGTGTGTGCGTGGGGAGCGCCGCGTGCGGCCCGCGCTGCCCG

GCGGCTGTGAGCGCTGCGGGCGCGGCGCGGGGCTTTGTGCGCTCCGCAGTGTGC

GCGAGGGGAGCGCGGCCGGGGGCGGTGCCCCGCGGTGCGGGGGGGGCTGCGAG

GGGAACAAAGGCTGCGTGCGGGGTGTGTGCGTGGGGGGGTGAGCAGGGGGTGT

GGGCGCGGCGGTCGGGCTGTAACCCCCCCCTGCACCCCCCTCCCCGAGTTGCTGA

GCACGGCCCGGCTTCGGGTGCGGGGCTCCGTACGGGGCGTGGCGCGGGGCTCGC

CGTGCCGGGCGGGGGTGGCGGCAGGTGGGGGTGCCGGGCGGGGCGGGGCCGC

CTCGGGCCGGGGAGGGCTCGGGGGAGGGGCGCGGCGGCCCCCGGAGCGCCGGC

GGCTGTCGAGGCGCGGCGAGCCGCAGCCATTGCCTTTTATGGTAATCGTGCGAGA

GGGCGCAGGGACTTCCTTTGTCCCAAATCTGTGCGGAGCCGAAATCTGGGAGGC

GCCGCCGCACCCCCTCTAGCGGGCGCGGGGCGAAGCGGTGCGGCGCCGGCAGGA

AGGAAATGGGCGGGGAGGGCCTTCGTGCGTCGCCGCGCCGCCGTCCCCTTCTCCC

TCTCCAGCCTCGGGGCTGTCCGCGGGGGGACGGCTGCCTTCGGGGGGACGGGG

CAGGGCGGGGTTCGGCTTCTGGCGTGTGACCGGCGGCTCTAGCCGGCGACCGGT

ATGCATCCTGGAGGCTTGCTGAAGGCTGTATGCTGATGAACATGGAATCCATGCA

GGTTTTGGCCACTGACTGACCTGCATGGTCCATGTTCATCAGGACACAAGGCCTG

TTACTAGCACTCACATGGAACAAATGGCCCCTAGCTCGCGATGCATCTAGAGCCT

CTGCTAACCATGTTCATGCCTTCTTCTTTTTCCTACAGCTCCTGGGCAACGTGCTG

GTTATTGTGCTGTCTCATCATTTTGGCAAAGAATTCCTCGAAGATCTAGGGAATT

CGATATCAAGCTTGGGGATTTTCAGGCACCACCACTGACCTGGGACAGTGTTAAC

GACACGATCCAatggcgacgaaggccgtgtgcgtgctgaagggcgacggcccagtg cagggcatcatcaatttcgagcagaaggaaagtaatggaccagtgaaggtgtggg gaagcattaaaggactgactgaaggcctgcacggctttcacgtccacgagtttgga gataatacagcaggctgtaccagtgcaggtcctcactttaatcctctatccagaaa acacggtgggccaaaggatgaagagaggcatgttggagacttgggcaatgtgactg ctgacaaagatggtgtggccgatgtgtctattgaagattctgtgatctcactct caggagaccattgcatcattggccgcacactggtggtccatgaaaaagcagatga cttgggcaaaggtggaaatgaagaaagtacaaagacaggaaacgctggaagtcgt ttggcttgtggtgtaattgggatcgcccaataaacattcccttggatgtagtctga ggccccttaactcatctgttatcctgctagctgtagaaatgtatcctgataaaca ttaaacactgtaatcttaaaagtgtaattgtgtgactttttcagagttgctttaaa gtacctgtagtgagaaactgatttatgatcacttggaagatttgtatagtttta taaaactcagttaaaatgtctgtttcaaGGCCGCTTCGAGCAGACATGATAAGATA

CATTGATGAGTTTGGACAAACCACAACTAGAATGCAGTGAAAAAAATGCTTTAT

TTGTGAAATTTGTGATGCTATTGCTTTATTTGTAACCATTATAAGCTGCAATAAA

CAAGTTAACAACAACAATTGCATTCATTTTATGTTTCAGGTTCAGGGGGAGAT

GTGGGAGGTTTTTTAAAGCAAGTAAAACCTCTACAAATGTGGTAAAATCGACGA

TAAGGATCTAGGAACCCCTAGTGATGGAGTTGGCCACTCCCTCTCTGCGCGCT

CGCTCGCTCACTGAGGCCGCCCGGGCAAAGCCCGGGCGTCGGGCGACCTTTGGT

CGCCCGGCCTCAGTGAGCGAGCGAGCGCGCAGAGAGGGAGTGGCCAA
```

>Sequence for single stranded CB-miR-CB-SOD1 (w/ 3' UTR);
AAV ITRs in bold (SEQ ID NO: 15)

GGGGGGGGGGGGGGGGTTGGCCACTCCCTCTCTGCGCGCTCGCTCGCTCAC

TGAGGCCGGGCGACCAAAGGTCGCCCGACGCCCGGGCTTTGCCCGGGCGG

CCTCAGTGAGCGAGCGAGCGCGCAGAGAGGGAGTGGCCAACTCCATCACTA

GGGGTTCCTAGATCTCAATATTGGCCATTAGCCATATTATTCATTGGTTATATAG

CATAAATCAATATTGGCTATTGGCCATTGCATACGTTGTATCTATATCATAATATG

TACATTTATATTGGCTCATGTCCAATATGACCGCCATGTTGGCATTGATTATTGAC

TAGTTATTAATAGTAATCAATTACGGGGTCATTAGTTCATAGCCCATATATGGAG

TTCCGCGTTACATAACTTACGGTAAATGGCCCGCCTGGCTGACCGCCCAACGACC

CCCGCCCATTGACGTCAATAATGACGTATGTTCCCATAGTAACGCCAATAGGGAC

TTTCCATTGACGTCAATGGGTGGAGTATTTACGGTAAACTGCCCACTTGGCAGTA

CATCAAGTGTATCATATGCCAAGTCCGCCCCCTATTGACGTCAATGACGGTAAAT

GGCCCGCCTGGCATTATGCCCAGTACATGACCTTACGGGACTTTCCTACTTGGCA

GTACATCTACGTATTAGTCATCGCTATTACCATGGTCGAGGTGAGCCCCACGTTC

TGCTTCACTCTCCCCATCTCCCCCCCCTCCCCACCCCCAATTTTGTATTTATTTATT

TTTTAATTATTTTGTGCAGCGATGGGGGCGGGGGGGGGGGGGGCGCGCGCCA

GGCGGGCGGGCGGGCGAGGGGCGGGGCGGGGCGAGGCGGAGAGGTGCGGC

GGCAGCCAATCAGAGCGGCGCGCTCCGAAAGTTTCCTTTTATGGCGAGGCGGCG

GCGGCGGCGGCCCTATAAAAAGCGAAGCGCGCGGCGGGCGGGAGTCGCTGCGA

CGCTGCCTTCGCCCCGTGCCCCGCTCCGCCGCCGCCTCGCGCCGCCCGCCCCGGC

TCTGACTGACCGCGTTACTCCCACAGGTGAGCGGGCGGGACGGCCCTTCTCCTCC

GGGCTGTAATTAGCGCTTGGTTTAATGACGGCTTGTTTCTTTTCTGTGGCTGCGTG

AAAGCCTTGAGGGGCTCCGGGAGGGCCCTTTGTGCGGGGGGGAGCGGCTCGGGG

GGTGCGTGCGTGTGTGTGCGTGGGGAGCGCCGCGTGCGGCCCGCGCTGCCCG

GCGGCTGTGAGCGCTGCGGGCGCGGCGCGGGGCTTTGTGCGCTCCGCAGTGTGC

GCGAGGGGAGCGCGGCCGGGGCGGTGCCCCGCGGTGCGGGGGGGCTGCGAG

GGGAACAAAGGCTGCGTGCGGGGTGTGTGCGTGGGGGGGTGAGCAGGGGGTGT

GGGCGCGGCGGTCGGGCTGTAACCCCCCCCTGCACCCCCCTCCCCGAGTTGCTGA

GCACGGCCCGGCTTCGGGTGCGGGGCTCCGTACGGGGCGTGGCGCGGGGCTCGC

CGTGCCGGGCGGGGGTGGCGGCAGGTGGGGGTGCCGGGCGGGGCGGGGCCGC

CTCGGGCCGGGAGGGCTCGGGGAGGGGCGCGGCGGCCCCCGGAGCGCCGGC

GGCTGTCGAGGCGCGGCGAGCCGCAGCCATTGCCTTTTATGGTAATCGTGCGAGA

GGGCGCAGGGACTTCCTTTGTCCCAAATCTGTGCGGAGCCGAAATCTGGGAGGC

GCCGCCGCACCCCCTCTAGCGGGCGCGGGGCGAAGCGGTGCGGCGCCGGCAGGA

AGGAAATGGGCGGGAGGGCCTTCGTGCGTCGCCGCGCCGCCGTCCCCTTCTCCC

TCTCCAGCCTCGGGGCTGTCCGCGGGGGGACGGCTGCCTTCGGGGGGGACGGGG

CAGGGCGGGGTTCGGCTTCTGGCGTGTGACCGGCGGCTCTAGCCGGCGACCGGT

ATGCATCCTGGAGGCTTGCTGAAGGCTGTATGCTGATGAACATGGAATCCATGCA

GGTTTTGGCCACTGACTGACCTGCATGGTCCATGTTCATCAGGACACAAGGCCTG

TTACTAGCACTCACATGGAACAAATGGCCCCTAGCTCGCGATGCATCTAGAGCCT

-continued

CTGCTAACCATGTTCATGCCTTCTTCTTTTTCCTACAGCTCCTGGGCAACGTGCTG

GTTATTGTGCTGTCTCATCATTTTGGCAAAGAATTCCTCGAAGATCTAGGGAATT

CGATATCAAGCTTGGGGATTTTCAGGCACCACCACTGACCTGGGACAGTGTTAAC

GACACGATCCAatggcgacgaaggccgtgtgcgtgctgaagggcgacggcccagtg cagggcatcatcaatttcgagcagaaggaaagtaatggaccagtgaaggtgtggg gaagcattaaaggactgactgaaggcctgcacggctttcacgtccacgagtttgga gataatacagcaggctgtaccagtgcaggtcctcactttaatcctctatccagaaa acacggtgggccaaaggatgaagagaggcatgttggagacttgggcaatgtgac tgctgacaaagatggtgtggccgatgtgtctattgaagattctgtgatctcactc tcaggagaccattgcatcattggccgcacactggtggtccatgaaaaagcagat gacttgggcaaaggtggaaatgaagaaagtacaaagacaggaaacgctggaagtc gtttggcttgtggtgtaattgggatcgcccaataaaGAGCAGACATGATAAGATA

CATTGATGAGTTTGGACAAACCACAACTAGAATGCAGTGAAAAAAATGCTTTATTT

GTGAAATTTGTGATGCTATTGCTTTATTTGTAACCATTATAAGCTGCAATAAACAA

GTTAACAACAACAATTGCATTCATTTTATGTTTCAGGTTCAGGGGGAGATGTGGGA

GGTTTTTTAAAGCAAGTAAAACCTCTACAAATGTGGTAAAATCGACGATAAGGAT

CTAGGAACCCCTAGTGATGGAGTTGGCCACTCCCTCTCTGCGCGCTCGCTCGCTC

ACTGAGGCCGCCCGGGCAAAGCCCGGGCGTCGGGCGACCTTTGGTCGCCC

GGCCTCAGTGAGCGAGCGAGCGCGCAGAGAGGGAGTGGCCAA

>SOD1 Promoter insert sequence
(SEQ ID NO: 16)

GTGAGCTGAGATTGCACCACTGCACTCCAGCCTGGTGACAGAGTGAGACTCCAT

ATCAAAATAAATACATAAATAAATAAAAACAGTGATTCTTAACTGGGAGTGATT

TGGCAACGTCTGGAATTATTTTTGGTTATCCCAGCCTGGCAGGGAGGGACAGGGT

ATTACTGGCATCTAGTGAGTAGGGGCTAGGGATTCTACTGAACATCCTACAGTGT

ACAGGACAGCCTCCACAGCAAAGAACTGTCTGGCCCAAAATGTCCATAGTGCCC

ACATTCGATGCCCTGCATTAGGAAGATATAAATACTCTTAAATATCACAGAGTTA

AATTCCTTACCCCTGTTCTAGCAGAGATGATATTCTTGCGGGGGAGCATCTTCTT

GGCTTCAACACATTCTTTTCTCCATGGGAGATGATGCCAGAAGAGGGACAGAAC

AGGGCCCAGTAAAGCATGGGGCCTGGGGCAGGGACCCCCTTGTTCAGGTGTGA

CGACCATCCTACGAAGGCACCACCCAGGCATCATTAGACCGTCTCAAAAGAAGA

GTAATTCACTGTCCCAAAGCAGCTCTCTCGTGTCTGTGGGCGGATCCCTTGGCAA

GTTTACAATGAACTGAAATCTGCCGAACTTCCTGGAACCCAAAGAAACTTTAGCC

TTGGGCAAAGGCCCTTTGGCCAGCATTTGCACTGTTTATGCAACCGTTTAGAATA

TACGAATTATCTGGAGACTACTACCAAATACAACAGGCAAAACTGCAAATATGT

ATACTTCCTAGAGGATGATAAAAAAATGTGAATTGTATTTCTCTGATAGAGGATG

CATTAGAGTCTGAGGGTCTAAATAGCGTAAATAATAAATAAGTAAATAAATCGA

TAGTAGTGTACTCCAAACGAGGCTGGAATAGCTTCTATTGTTGTTTCACACTGGA

CTTCAATTAAGTCTCAGTATTTTGCCATACTCAATATTAAGTACTAGGCTGGACGT

GGTGGCTCATGTCTGTAATCCCAGCACTTTGGGAGGCCGAGGTGGGTAGATGGCT

GGCTTGAGCTCAGGAGTTTGAAACCAGCCTGGGCAACATGGTAAAACCCCATCT

```
GTACCCAAAATACAAAAATCAGCCAGGTGTGGTGGCACATGCCTGTGGTCCCAG

GTACTTGGGAGGCTGAGGCAGGAGGATGGCTTGAACCCAGGAGGTGGAGGCTGC

AGTGAGCTATGATGGCGCCACTGCACTCCAGCCTGGGTGACAGAGCGAGACCCT

GTCTCAAAAATCAAACAAACAACCCCCTCGCCCCGGACAAAAGTAGTTTGCACT

ATTTTCTCATTTCACAATATGTTTTTGAAATATTTCCCTTGAAAGGTAAGTCATAT

TTATCATTCCTGTTGTATGGAGGCATCATAAATTATTTCACCATTCTACCCTCCTT

GAGTGTTGTGGCCTTTAGGCCAGACAAAAACGCAGGTGATGCCTAGAAGCCAAC

TAGTTGCCGTTTGGTTATCTGTAGGGTTGTGGCCTTGCCAAACAGGAAAAATATA

AAAAGAATACCGAATTCTGCCAACCAAATAAGAAACTCTATACTAAGGACTAAG

AAAATTGCAGGGGAAGAAAAGGTAAGTCCCGGGATTGAGGTGTAGCGACTTTCT

ATACCCTCAGAAAACTAAAAAACAAGACAAAAAAATGAAAACTACAAAAGCAT

CCATCTTGGGGCGTCCCAATTGCTGAGTAACAAATGAGACGCTGTGGCCAAACTC

AGTCATAACTAATGACATTTCTAGACAAAGTGACTTCAGATTTTCAAAGCGTACC

CTGTTTACATCATTTTGCCAATTTCGCGTACTGCAACCGGCGGGCCACGCCCCCG

TGAAAAGAAGGTTGTTTTCTCCACATTTCGGGGTTCTGGACGTTTCCCGGCTGCG

GGGCGGGGGAGTCTCCGGCGCACGCGGCCCCTTGGCCCCGCCCCCAGTCATTC

CCGGCCACTCGCGACCCGAGGCTGCCGCAGGGGCGGGCTGAGCGCGTGCGAGG

CGATTGGTTTGGGGCCAGAGTGGGCGAGGCGCGGAGGTCTGGCCTATAAAGTAG

TCGCGGAGACGGGGTGCTGGTTTGCGTCGTAGTCTCCTGCAGCGTCTGGGGTTTC

CGTTGCAGTCCTCGGAACCAGGACCTCGGCGTGGCCTAGCGAGTT

>Wild-type SOD1 amino acid sequence; NCBI Reference
Sequence NP_000445.1
                                            (SEQ ID NO: 17)
MATKAVCVLKGDGPVQGIINFEQKESNGPVKVWGSIKGLTEGLHGFHVHEFGDNTA

GCTSAGPHFNPLSRKHGGPKDEERHVGDLGNVTADKDGVADVSIEDSVISLSGDHCII

GRTLVVHEKADDLGKGGNEESTKTGNAGSRLACGVIGIAQ
```

---

What is claimed is:

1. An isolated nucleic acid comprising:
   (a) a first region that encodes one or more first miRNAs comprising a nucleic acid having sufficient sequence complementary with an endogenous mRNA of a subject to hybridize with and inhibit expression of the endogenous mRNA, wherein the endogenous mRNA encodes a SOD1 protein; and
   (b) a second region encoding an exogenous mRNA that encodes a wild-type SOD1 protein,
   wherein the one or more first miRNAs do not comprise a nucleic acid having sufficient sequence complementary to hybridize with and inhibit expression of the exogenous mRNA,
   wherein the wild-type SOD1 protein is encoded by a sequence comprising the sequence set forth in SEQ ID NO: 7.

2. The isolated nucleic acid claim 1, wherein the one or more first miRNAs:
   (a) targets an untranslated region of the nucleic acid encoding the endogenous mRNA;
   (b) targets a coding sequence of the nucleic acid encoding the endogenous mRNA;
   (c) hybridizes to a nucleic acid comprising 5, 6, 7, 8, 9, 10, 11, 12, 13, 14, 15, 16, 17, 18, 19, 20, or 21 consecutive nucleotides of a RNA encoded by a sequence as set forth in SEQ ID NO: 2; and/or (d) is encoded by 5, 6, 7, 8, 9, 10, 11, 12, 13, 14, 15, 16, 17, 18, 19, 20, or 21 consecutive nucleotides of a sequence comprising the sequence as set forth in SEQ ID NO: 3 and/or 4.

3. The isolated nucleic acid of claim 2, wherein the one or more first miRNAs further comprise flanking regions of miR-155 or miR-30.

4. The isolated nucleic acid of claim 1, further comprising a first promoter operably linked to the first region.

5. The isolated nucleic acid of claim 1, further comprising a second promoter, wherein the second promoter is operably linked to the second region.

6. The isolated nucleic acid of claim 1, further comprising an enhancer sequence.

7. The isolated nucleic acid of claim 1, wherein the first region is positioned within an untranslated region of the second region.

8. The isolated nucleic acid of claim 7, wherein the first region is positioned within an intron of the second acid.

9. The isolated nucleic acid of claim 1, wherein the first region is positioned 5' with respect to the second region.

10. The isolated nucleic acid of claim 1, further comprising at least one adeno-associated virus (AAV) inverted terminal repeat (ITR).

11. The isolated nucleic acid of claim 10, comprising a full-length ITR and a mutant ITR, wherein the ITRs flank the first and second regions.

12. A recombinant adeno-associated virus (rAAV) comprising:
(i) the isolated nucleic acid of claim 1; and
(ii) an AAV capsid protein.

13. The rAAV of claim 12, wherein the rAAV targets tissue of the central nervous system (CNS).

14. The rAAV of claim 12, wherein the capsid protein is AAV9 capsid protein or AAVrh.10 capsid protein.

15. A composition comprising the isolated nucleic acid of claim 1, and a pharmaceutically acceptable excipient.

16. The isolated nucleic acid of claim 1, wherein the exogenous mRNA lacks a 5' untranslated region (5' UTR), lacks a 3' untranslated region (3' UTR), or lacks both a 5' UTR and a 3'UTR.

17. The isolated nucleic acid of claim 1, wherein the exogenous mRNA encoding the SOD1 protein has one or more silent base pair mutations relative to the endogenous mRNA.

18. The isolated nucleic acid of claim 17, wherein the exogenous mRNA comprises a nucleic acid sequence that is at least 95% identical to the endogenous mRNA.

* * * * *

UNITED STATES PATENT AND TRADEMARK OFFICE
CERTIFICATE OF CORRECTION

PATENT NO. : 11,739,330 B2
APPLICATION NO. : 16/649164
DATED : August 29, 2023
INVENTOR(S) : Christian Mueller et al.

It is certified that error appears in the above-identified patent and that said Letters Patent is hereby corrected as shown below:

In the Claims

In Claim 8, Column 83, beginning at Line 20, the text:
"region is positioned within an intron of the second acid."
Should read:
--region is positioned within an intron of the second region.--

Signed and Sealed this
Seventeenth Day of October, 2023

Katherine Kelly Vidal
*Director of the United States Patent and Trademark Office*